United States Patent
Renner et al.

(10) Patent No.: US 11,872,239 B2
(45) Date of Patent: Jan. 16, 2024

(54) MODIFIED OLIGOMERIC COMPOUNDS COMPRISING TRICYCLO-DNA NUCLEOSIDES AND USES THEREOF

(71) Applicant: Synthena AG, Bern (CH)

(72) Inventors: Wolfgang Andreas Renner, Zurich (CH); Branislav Dugovic, Bern (CH); Reto Bertolini, Liebefeld (CH)

(73) Assignee: Synthena AG, Bern (CH)

( * ) Notice: Subject to any disclaimer, the term of this patent is extended or adjusted under 35 U.S.C. 154(b) by 0 days.

(21) Appl. No.: 16/604,764

(22) PCT Filed: Apr. 20, 2018

(86) PCT No.: PCT/IB2018/052781
§ 371 (c)(1),
(2) Date: Oct. 11, 2019

(87) PCT Pub. No.: WO2018/193428
PCT Pub. Date: Oct. 25, 2018

(65) Prior Publication Data
US 2020/0390792 A1   Dec. 17, 2020

Related U.S. Application Data

(60) Provisional application No. 62/562,124, filed on Sep. 22, 2017.

(30) Foreign Application Priority Data

Apr. 20, 2017   (EP) .................................... 17167427

(51) Int. Cl.
*A61K 31/7028*   (2006.01)
*A61K 47/54*   (2017.01)
*A61P 21/00*   (2006.01)
*C12N 15/113*   (2010.01)

(52) U.S. Cl.
CPC ........ *A61K 31/7028* (2013.01); *A61K 47/544* (2017.08); *A61P 21/00* (2018.01); *C12N 15/113* (2013.01)

(58) Field of Classification Search
CPC . A61K 31/712; A61K 31/7125; C12N 15/113
USPC ..................... 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 2005/0113325 A1 | 5/2005 | Gryaznov et al. | |
| 2011/0092570 A1* | 4/2011 | Swayze ................. | C07H 21/04 536/24.5 |
| 2012/0149756 A1 | 6/2012 | Schumperli et al. | |
| 2014/0296323 A1 | 10/2014 | Leumann et al. | |
| 2015/0141637 A1 | 5/2015 | Leumann et al. | |
| 2015/0376624 A1* | 12/2015 | Gryaznov ............ | C12N 15/113 536/25.31 |
| 2016/0002280 A1* | 1/2016 | Leumann ............... | C07H 19/10 536/23.1 |

FOREIGN PATENT DOCUMENTS

| | | |
|---|---|---|
| WO | 2005/023994 A2 | 3/2005 |
| WO | 2016161388 A1 | 10/2016 |

OTHER PUBLICATIONS

Communication from European Patent Office dated Oct. 22, 2020 for European Patent Application No. 18721490.3, 5 pages.
Lietard, Jory et al., "Synthesis, Pairing, and Cellular Uptake Properties of C(6')-Functionalized Tricyclo-DNA," Journal of Organic Chemistry, Jan. 1, 2012 (Jan. 1, 2012), pp. 4566-4577.
International Search Report and Written Opinion dated Jun. 21, 2018 for International Patent Application No. PCT/IB2018/052781, 8 pages.
1 Extended European Search Report foe EP 21214936.3 dated May 17, 2022, 13 pages.
Official Action from Japanese Patent Office dated Jan. 21, 2022 for Japanese Patent Application No. 2019-556616, 5 pages.
Office Action issued in corresponding Japanese Application No. 2022-116326, dated May 26, 2023, 4 pages, with English translation.
Notice of Final Office Action dated Nov. 21, 2022 for related Japanese Patent Application No. 2019-556616, 6 pages.
First Office Action dated Oct. 8, 2022 for related Chinese Patent Application No. 201880041193.1, 36 pages.

* cited by examiner

Primary Examiner — Jane J Zara
(74) Attorney, Agent, or Firm — Morgan, Lewis & Bockius LLP

(57) ABSTRACT

The present invention relates to a composition comprising an oligomeric compound comprising one or more tricyclo-deoxyribonucleic acid (tc-DNA) nucleosides and one or more lipid moiety, wherein said one or more lipid moiety is covalently linked to said oligomeric compound either directly or via a spacer, and wherein preferably said oligomeric compound comprises from 5 to 40 monomer subunits, as well as pharmaceutical compositions thereof and their uses in the prevention or treatment of neuromuscular or musculoskeletal diseases such as Duchenne muscular dystrophy or Steinert disease.

12 Claims, 23 Drawing Sheets

Specification includes a Sequence Listing.

MODIFIED OLIGOMERIC COMPOUNDS COMPRISING TRICYCLO-DNA NUCLEOSIDES AND USES THEREOF

STATEMENT OF RELATED APPLICATIONS

This application is a 371 U.S. National Stage application of International Patent Application No. PCT/IB2018/052781, filed Apr. 20, 2018, which claims priority to European Patent Application No. 17167427.8, filed Apr. 20, 2017 and to U.S. Provisional Application No. 62/562,124, filed Sep. 22, 2017, each of which are herein incorporated by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name of "Sequence_Listing (12)", creation date of Oct. 11, 2019 and having a size of 27.2 KB. The sequence listing submitted via EFS-Web is part of the specification and is herein incorporated by reference in its entirety.

The present invention relates to compositions comprising an oligomeric compound comprising one or more tricyclo-deoxyribonucleic acid (tc-DNA) nucleosides and one or more lipid moiety covalently linked to said oligomeric compound either directly or via a spacer. As well as to methods for the treatment of a number of diseases including Duchenne muscular dystrophy (DMD), spinal muscular atrophy (SMA), Pompe disease and Myotonic dystrophy type I (DM1) by using said compositions of the present invention.

BACKGROUND OF THE INVENTION

Antisense technology is an effective means for reducing the expression of specific gene products and can therefore be useful in therapeutic, diagnostic, and research applications. Generally, the principle behind antisense technology is that an antisense compound (a sequence of nucleotides or analogues thereof) hybridizes to a target nucleic acid and modulates gene expression activities or function, such as transcription and/or translation. Regardless of the specific mechanism, its sequence-specificity makes antisense compounds attractive as tools for target validation and gene functionalization, as well as therapeutics to selectively modulate the expression of genes involved in the pathogenesis of diseases.

Chemically modified nucleosides are typically incorporated into antisense compounds to enhance its properties, such as nuclease resistance, pharmacokinetics or affinity for a target RNA. These chemically-modified antisense oligonucleotides (AONs) include structural modifications of natural RNA such as 2'-OH modifications, locked nucleic acids (LNAs), peptide nucleic acids (PNAs), hexitol nucleic acids (HNAs) as well as tricyclo-DNAs (tcDNA) and many others (reviews: Bennett C F and Swayze E E, Annu. Rev. Pharmacol. Toxicol. 2010, 50:259-293; Deleavey G F and Damha M, Chemistry & Biology 2012, 19, 937-954; Sharma V. K. et al., Med. Chem. Commun. 2014, 5, 1454-1471; Siva, et al., Nucleic Acid Therapeutics 2014, 24:69-86; Goyenvalle A. et al., Journal of Neuromuscular Diseases 2016 3:157-167; the disclosures of which are incorporated by reference herein). Moreover, modifications of the backbone such as the phosphorothioate (PS) linkage, where one of the non-bridging oxygen atoms of a phosphodiester linkage is replaced with a sulfur atom is one of the most widely investigated nucleic acid chemical modifications in oligonucleotide therapeutics.

Duchenne muscular dystrophy (DMD) is an X-linked recessive disorder that affects one in every 3500 live male births (Emery. Neuromuscul. Disord. 1991). It is caused by mutations in the gene that encodes dystrophin, a large protein (427 kDa) found in a variety of tissues, especially in striated muscle fibers and neurons in particular regions of the central nervous system (Kunkel et al., PNAS. 1985; Muntoni F et al., Lancet Neurol. 2003). Dystrophin is located close to the inner surface of the plasma membrane, connecting the actin cytoskeleton to the extracellular matrix through a membrane dystrophin-associated glycoprotein complex (Culligan et al., 1988). Lack of dystrophin makes that muscle fibers are particularly vulnerable to mechanical stress and undergo recurrent cycles of necrosis. As a result, patients display progressive weakness of skeletal muscles, which are with time replaced by adipofibrotic tissue, leading to loss of ambulation by the age of twelve, whereupon premature death is caused by either respiratory failure or cardiomyopathy. In addition, about one third of DMD patients also display cognitive impairment suggesting a noteworthy disruption of neuronal and brain function (Bresolin et al., Neuromuscul. Disord. 1994).

The full-length dystrophin, translated from a major 14-kb mRNA transcript made of 79 exons, is a modular protein that can fortunately support the deletion of multiple exons provided the open reading frame is preserved (Koenig et al., Cell. 1987). This phenomenon occurs in the clinically milder disease Becker muscular dystrophy (BMD), where deletions that maintain the open reading frame lead to the synthesis of truncated semi-functional forms of dystrophin (Monaco et al. Genomics. 1988). Human DMD is caused by a heterogeneous group of mutations that occur across 79 exons, although two regions of highest incidence are observed in the exon 3-7 and exon 45-55 regions. Muntoni, Neuromuscul. Disord. 2009, 20, 355-362. DMD results from out-of-frame deletions in the dystrophin mRNA or are caused by an improper stop codon. This results in an out-of-frame truncated mRNA, unstable and incomplete dystrophin, and ultimately the clinical appearance of DMD. In-frame truncated mRNA is known to result from a different mutation that leads to semifunctional dystrophin and to said much milder form myopathy known as Becker muscular dystrophy (BMD). Hence, it was proposed, fifteen years ago, that interfering with the splicing process of selected exons by using antisense oligonucleotides (AON) might be a suitable therapeutic approach for DMD (Matsuo M. Brain Dev. 1996). The goal of oligonucleotide therapies against DMD is generally to cause exon skipping (e.g., of exon 23 or exon 51, or any other exon), restore dystrophin production, and transform DMD into BMD, resulting in reduced mortality and potentially cognitive improvement. Besides DMD, numerous other diseases can also be potentially treated by oligonucleotide-mediated exon skipping approaches, including those diseases described hereinafter.

Two types of compounds have been extensively tested for antisense-induced exon skipping, the 2'-O-methyl-modified ribose oligomers with a full-length phosphorothioate backbone (2'OMe-PS) and the phosphorodiamidate morpholino oligomers (PMO). Both types of antisense molecules have been shown to rescue dystrophin in skeletal muscle after systemic delivery in animal models of DMD and in clinical trials (van Deutekom et al., New. Engl. J. Med. 2007; Kinali et al., Lancet Neurol. 2009; Goemans et al., New. Engl. J.

Med. 2011; Cirak et al., Lancet. 2011). However, recent studies using 2'OMe-PS and PMO AONs targeting exon 51 in DMD patients have failed to show marked clinical benefit likely due to insufficient levels of dystrophin rescue (Lu et al., Mol. Ther. Nucleic Acids. 2014). Moreover, it was known from preclinical studies in mice that these two chemistries were not appropriate for addressing cardiac and cognitive defects, which still represent a key challenge for success in many neuromuscular disorders. More recent studies in the mdx mouse model of DMD have demonstrated that tcDNA AONs with full PS backbone induced effective skipping of exon 23 to levels 5-6-fold higher than that achieved with 2'OMe-PS and PMO AONs (Goyenvalle et al., Nat. Med. 2015).

Importantly, this translated into a greater rescue of dystrophin protein levels, particularly in the diaphragm and heart, where levels reached 50% and 40% respectively, compared to wild-type mice after 12 weeks of treatment. However, the substitution of sulfur for oxygen in the phosphate ester backbone, while significantly improving biodistribution, has also been shown to be involved in unspecific protein binding as well as activation of the innate immune system, particularly complement activation, which may possibly result in the worst in acute toxicity, at best in long-term toxicity (Dirin and Winkler, Expert Opin. Biol. Ther. 2013).

This major hurdle compromising or at least restraining the therapeutic potential of this class of molecules has prompted us to search for novel entities with higher efficiency and potentially lower toxicity.

SUMMARY OF THE INVENTION

It has been surprisingly found that the inventive compositions comprising an oligomeric compound and one or more lipid moiety covalently linked to said oligomeric compound are much more efficient and active in penetrating skeletal muscles, cardiac tissue and CNS after systemic delivery than their tcDNA counterparts not comprising said one or more lipid moiety. The latter was the case irrespective of the nature of the internucleosidic linkages present in the corresponding oligomeric counterparts, and thus irrespective whether the counterparts had a full PS backbone. Moreover, the inventors were able to show the unexpected property of the inventive compositions to penetrate efficiently the cardiac tissue and cross the blood-brain barrier avoiding the need of PS internucleosidic linkages therefore, which potentially markedly improves safety profiles and lowers toxicity while remaining high efficacy. This allows increasing the dosage of the applied inventive pharmaceutical compositions to tailor and satisfy the medical needs.

Furthermore, the inventive compositions have been shown to be transported in the blood stream after intravenous systemic application to all skeletal muscles, to the cardiac muscle and to the CNS and to be taken up by these tissues. Thus, the inventive compositions are particularly useful as antisense oligonucleotides (AONs), in particular for obtaining an antisense effect in muscles and in cardiac cells, or in the CNS, after systemic delivery. The present invention therefore also provides compositions for a number of diseases caused by abnormal gene expression in a tissue or cell of a subject. It is believed, without being bound by this theory, that the inventive compositions are forming aggregates with blood albumin and thereby ensuring not only the transport of the inventive compositions within the blood stream, but further increasing the circulation half-life and thus the exposure time of the tissues to the inventive compositions, and, moreover, enhancing degradation resistance in plasma.

Moreover, preferred inventive compositions comprising said one or more lipid moiety covalently linked to said oligomeric compound remain high efficacy even if the number of phosphorothioate internucleosidic linkage groups within said oligomeric compounds are reduced in favour of phosphorodiester internucleosidic linkage groups. Thus, it has been found that preferred inventive compositions, in particular the compositions comprising fatty acid or fatty diacid moieties such as palmitoyl moieties and comprising a high number of phosphorodiester internucleosidic linkage groups, induce significantly higher levels of exon skipping in a plurality of tissues compared to their corresponding tc-DNA analogues not having said lipid moieties linked thereto.

Thus, in a first aspect, the present invention provides for a composition comprising an oligomeric compound comprising one or more tricyclo-deoxyribonucleic acid (tc-DNA) nucleosides and one or more lipid moiety, preferably exactly one lipid moiety, wherein said one or more lipid moiety is covalently linked to said oligomeric compound either directly or via a spacer, and wherein preferably said oligomeric compound comprises from 5 to 40 monomer subunits.

In a further aspect, the present invention provides for a pharmaceutical composition comprising the inventive composition and further comprising a pharmaceutically acceptable carrier, wherein preferably said pharmaceutical composition is for use in the prevention, treatment or diagnosis of a neuromuscular or musculoskeletal disease, wherein further preferably said neuromuscular or said musculoskeletal disease is selected from Duchenne muscular dystrophy, familial dysautonomia, spinal muscular atrophy, ataxia telangiectasia, congenital disorder of glycosylation, frontotemporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In another aspect, the present invention provides for the inventive pharmaceutical composition comprising the inventive composition and further comprising a pharmaceutically acceptable carrier, wherein preferably said pharmaceutical composition is for use in the treatment of a neuromuscular or musculoskeletal disease, wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In again a further aspect, the present invention provides for the inventive composition for use as a medicament in the prevention, treatment or diagnosis of a disease, wherein preferably said disease is a neuromuscular or musculoskeletal disease, and wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In a further aspect, the present invention provides for the inventive composition for use as a medicament in the treatment of a disease, wherein preferably said disease is a neuromuscular or musculoskeletal disease, and wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In a further aspect, the present invention provides for the inventive composition for use in a method of treating a disease, wherein preferably said disease is a neuromuscular or musculoskeletal disease, and wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In a further aspect, the present invention provides for the inventive composition for use in a method of preventing, treating or diagnosing a disease, wherein preferably said disease is a neuromuscular or musculoskeletal disease, and wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

In again a further aspect, the present invention provides for a method for treating a neuromuscular or musculoskeletal disease comprising the step of administering to a patient a therapeutically effective dose of the inventive composition or the inventive pharmaceutical composition. In a preferred embodiment thereof, said neuromuscular or musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and wherein preferably the neuromuscular or musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

Further aspects and embodiments of the present invention will become apparent as this description continues.

DETAILED DESCRIPTION OF THE INVENTION

Figure 1:
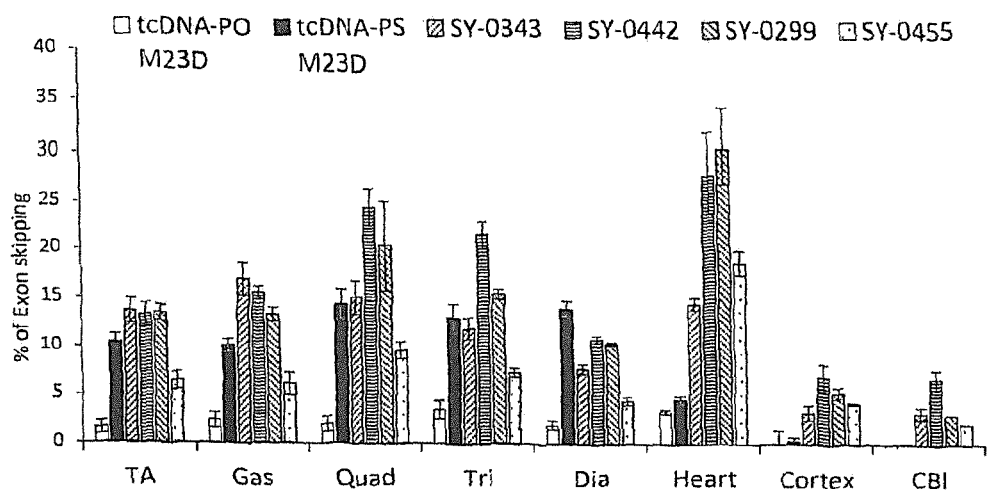
FIG. 1: Detection of exon 23-skipped dystrophin mRNA in mdx muscles and CNS, including tibialis anterior (TA), gastrocnemius (Gas), quadriceps (Quad), triceps (Tri), biceps (Bi), diaphragm (Dia), heart, cortex and cerebellum (Cbl) after 4 weeks of treatment with a dosage of 200 mg/kg/wk for tcDNA-PO M23D (SY-0308), tcDNA-PS M23D (SY-0210), SY-0299, SY-0442 and SY-0455, and 178 mg/kg/wk for SY-0343. Exon 23 skipping is quantified by Taqman qPCR and expressed as a percentage of total dystrophin, measured by the exon 4-5 expression level, after normalization with an endogenous control. N=4 mice per group; error bars are mean±SEM.
Figure 2A:
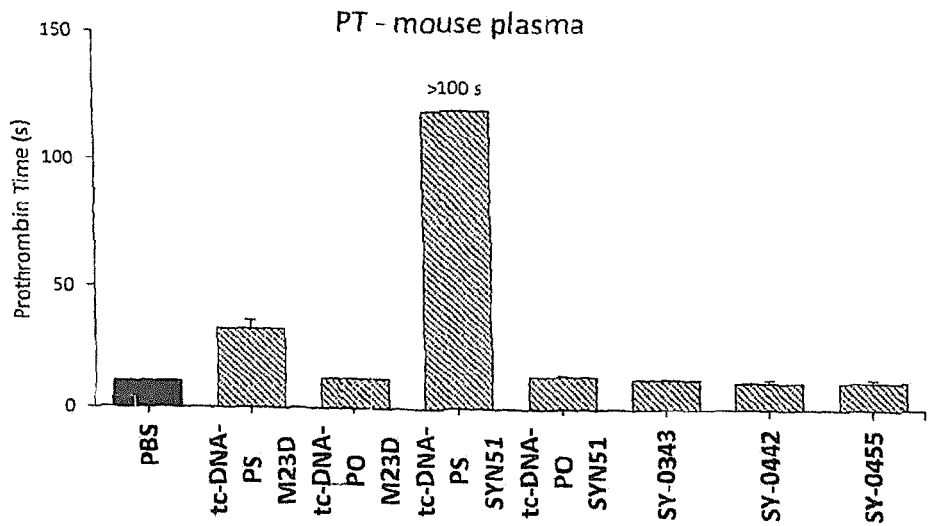
FIG. 2: The Prothrombin Time and the Partial Thromboplastin Time are two blood-tests that measure how long it takes for blood to clot, given to anticipate bleeding problems. Two mg/ml of following sequences: tcDNA-PO M23D (SY-0308, SEQ ID NO: 1) or tcDNA-PS M23D (SY-0210, SEQ ID NO: 23) or tcDNA-PS SYN51 (SEQ ID NO:19 with all nucleotides being tc-DNAs and all internucleosidic linkage groups being PS linkage groups) or tcDNA-PO SYN51 (SEQ ID NO:19 with all nucleotides being tc-DNAs and all internucleosidic linkage groups being PO linkage groups) or SY-0343 or SY-0442 or SY-0455, were incubated with 50 µl of citrated plasma C for 30 min at 37°, then the prothrombin time (PT) and the activated partial thromboplastin time (PTT) assays were performed on a semi-automated START max coagulometer (Stago) following manufacturer's instructions (A mouse plasma, B human plasma). PBS (phosphate buffer saline) was used as negative control and the (tcDNA-PS SYN51) with full PS backbone that was highly toxic in mouse as positive control.
Figure 2B:
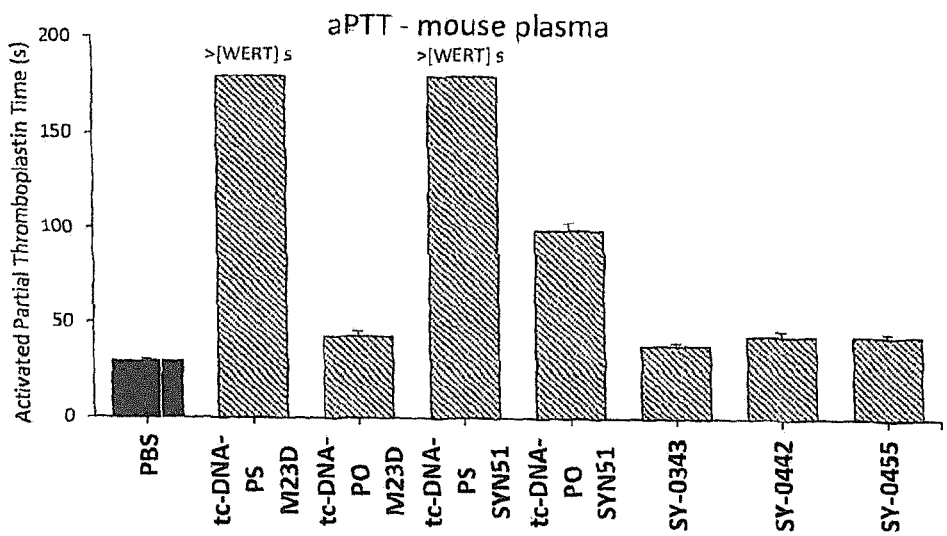
Figure 2C:
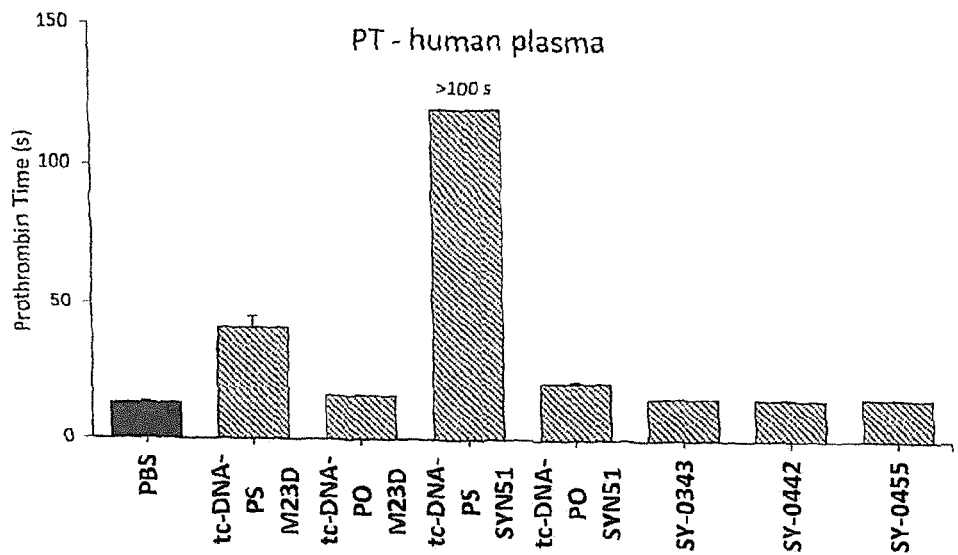
Figure 2D:
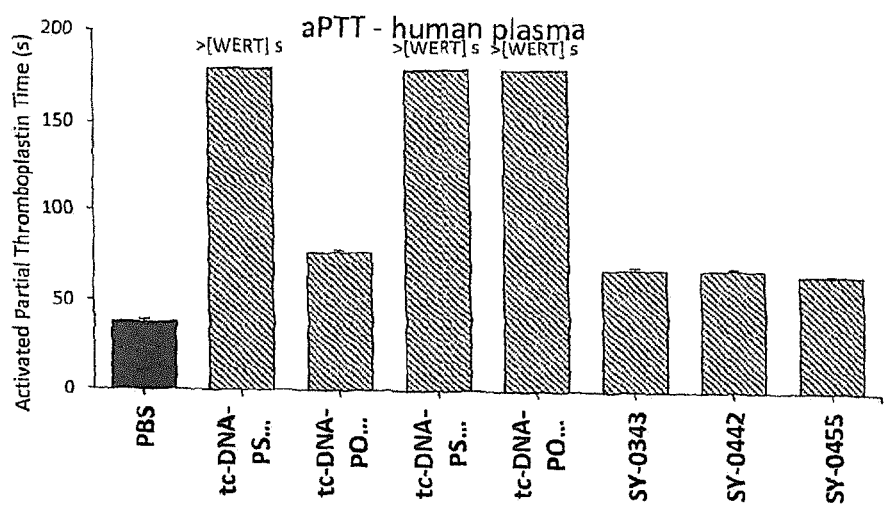

Unless defined otherwise, all technical and scientific terms used herein have the same meanings as commonly understood by one of ordinary skill in the art to which this invention belongs. The headings used herein are solely for convenience reasons and should not be construed as limiting for the disclosure of any of the aspects and embodiments of the present invention.

Definitions

The term "oligomeric compound", as used herein, refers to a compound comprising preferably eight or more monomer subunits linked by internucleosidic linkage groups, wherein at least two of said eight or more monomer subunits are tricyclo-deoxyribonucleic acid (tc-DNA) nucleosides.

The term "monomer subunit", as used herein, is meant to include all manner of monomer units that are amenable to oligomer synthesis including, and typically and preferably referring to, monomer subunits such as α-D-ribonucleosides, β-D-ribonucleosides, α-D-2'-deoxyribonucleosides, β-D-2'-deoxyribonucleosides, naturally occurring nucleosides, modified nucleosides, and hereby in particular tricyclo-deoxyribonucleic acid (tc-DNA) nucleosides and 2'-modified ribonucleic acid (2'-modified-RNA) nucleosides, locked nucleic acid (LNA) nucleosides, peptide nucleic acids (PNAs) nucleosides, 2'-deoxy 2'-fluoro-arabino nucleosides, hexitol nucleic acids (HNAs) nucleosides; and phosphorodiamidate morpholino (PMO) nucleosides, mimetics of nucleosides, naturally occurring nucleotides, modified nucleotides, and hereby in particular tricyclo-deoxyribonucleic acid (tc-DNA) nucleotides and 2'-modified ribonucleic acid (2'-modified-RNA) nucleotides, and mimetics of nucleotides. Typically and preferably, the term "monomer subunit", as used herein, refers to naturally occurring nucleosides and modified nucleosides, and hereby in particular to ribonucleosides, deoxyribonucleosides, tricyclo-deoxyribonucleic acid (tc-DNA) nucleosides, 2'-modified ribonucleic acid (2'-modified-RNA) nucleosides, locked nucleic acid (LNA) nucleosides, peptide nucleic acids (PNAs) nucleosides, 2'-deoxy 2'-fluoro-arabino nucleosides, hexitol nucleic acids (HNAs) nucleosides and phosphorodiamidate morpholino (PMO) nucleosides, and to naturally occurring nucleotides and modified nucleotides, and hereby in particular to ribonucleotides, deoxyribonucleotides, tricyclo-deoxyribonucleic acid (tc-DNA) nucleotides, 2'-modified ribonucleic acid (2'-modified-RNA) nucleotides, locked nucleic acid (LNA) nucleotides, peptide nucleic acids (PNAs) nucleotides, 2'-deoxy 2'-fluoro-arabino nucleotides, hexitol nucleic acids (HNAs) nucleotides and phosphorodiamidate morpholino (PMO) nucleotides. Further preferably, the term "monomer subunit", as used herein, refers to modified nucleotides, and hereby in particular tricyclo-deoxyribonucleic acid (tc-DNA) nucleotides and 2'-modified ribonucleic acid (2'-modified-RNA) nucleotides.

The term "lipid moiety" as used herein refers to moieties that are derived from, typically and preferably, hydrocarbons, oils, fats (such as fatty acids, glycerides), sterols, steroids, and derivative forms of these compounds. Suitable lipid moieties include moieties derived from fatty acids and their derivatives, hydrocarbons and their derivatives, and sterols, such as cholesterol. As used herein, the term lipid moiety also includes amphipathic compound moieties, which contain both lipid and hydrophilic moieties.

The term "hydrocarbon", as used herein, encompasses compounds that consist only of hydrogen and carbon, joined by covalent bonds. The term encompasses open chain (aliphatic) hydrocarbons, including straight (unbranched) chain and branched hydrocarbons, and saturated as well as mono- and polyunsaturated hydrocarbons. The term also encompasses hydrocarbons containing one or more aromatic ring, preferably the term excludes hydrocarbons containing one or more aromatic ring. The terms "straight" and "unbranched", are interchangeably used herein.

The term "fatty acid", as used herein, refers to a hydrocarbon chain that terminates with a carboxylic acid group, wherein said hydrocarbon chain is typically and preferably either an alkyl or alkenyl of typically 3 to 32 carbons long, and that are, thus, saturated or unsaturated, and that are optionally substituted by one or more, preferably one, carboxylic group (—COOH), one or more, preferably one, $C_{1-32}$ alkyl, one or more, preferably one, phosphate group (HOP(O)(OH)O—), one or more, preferably one, phosphonate group (HOP(O)O—), one or more, preferably one, thiophosphate group (HOP(O)(SH)O—), one or more, preferably one, dithiophosphate group (HOP(S)(SH)O—), one or more, preferably one, diphosphate group (HO—P(O)(OH)—O—P(O)(OH)—O—), one or more, preferably one, triphosphate group (HO—P(O)(OH)—O—P(O)(OH)—O—P(O)(OH)—O—), one or more phenyl group (—$C_6H_5$), one or more phenyl group substituted with a halogen, preferably iodine, or a carboxylic group. If a fatty acid contains one or more double bond, and is thus unsaturated, there is the possibility of either a cis or trans geometric isomerism. The term "fatty acid moiety", as used herein, refers to a moiety derived from a fatty acid, as defined herein, wherein one carboxylic group (—COOH) of said fatty acid becomes and is a —C(O)— group of said fatty acid moiety, which —C(O)— group is linked to said oligonucleotide either directly or via spacer in accordance with the present invention. Preferably, the term "fatty acid" as used herein refers to a hydrocarbon chain that terminates with a carboxylic acid group, wherein said hydrocarbon chain is typically and preferably either an alkyl or alkenyl of typically 3 to 32 carbons long, and that are, thus, saturated or unsaturated, and that are optionally substituted by one or more, preferably one, carboxylic group (—COOH), one or more, preferably one, $C_{1-32}$ alkyl, one or more, preferably one, phosphate group (HOP(O)(OH)O—), one or more, preferably one, phosphonate group (HOP(O)O—), one or more, preferably one, thiophosphate group (HOP(O)(SH)O—), one or more, preferably one, dithiophosphate group (HOP(S)(SH)O—), one or more, preferably one, diphosphate group (HO—P(O)(OH)—O—P(O)(OH)—O—), one or more, preferably one, triphosphate group (HO—P(O)(OH)—O—P(O)(OH)—O—P(O)(OH)—O—), one or more phenyl group (—$C_6H_5$), one or more phenyl group substituted with a halogen, preferably iodine, or a carboxylic group. Preferably, said fatty acid has an even numbers of carbon atoms, wherein the carbon atom of the carboxylic group (—COOH) of said fatty acid or said —C(O)— group of said fatty acid moiety is included in the counting of the numbers of carbon atoms.

Thus, fatty acids preferably contain even or uneven numbers, preferably even numbers, of carbon atoms in a straight chain (commonly 3-32 carbons) and can be saturated or unsaturated, and can contain, or be modified to contain, a variety of substituent groups, preferably by one or more, preferably one, carboxylic group (—COOH), one or more, preferably one, $C_{1-32}$ alkyl, one or more, preferably one, phosphate group (HOP(O)(OH)O—), one or more, preferably one, phosphonate group (HOP(O)O—), one or more, preferably one, thiophosphate group (HOP(O)(SH)O—), one or more, preferably one, dithiophosphate group (HOP(S)(SH)O—), one or more, preferably one, diphosphate group (HO—P(O)(OH)—O—P(O)(OH)—O—), one or more, preferably one, triphosphate group (HO—P(O)(OH)—O—P(O)(OH)—O—P(O)(OH)—O—), one or more phenyl group (—$C_6H_5$), one or more phenyl group substituted with a halogen, preferably iodine, or a carboxylic group.

The term "fatty diacid" refers to fatty acids as defined herein but with an additional carboxylic acid group in the omega position. Thus, fatty diacids are dicarboxylic acids. The term "fatty diacid moiety", as used herein, refers to a moiety derived from a fatty diacid, as defined herein, wherein one carboxylic group (—COOH) of said fatty diacid becomes and is a —C(O)— group of said fatty diacid moiety, which —C(O)— group is linked to said oligonucleotide either directly or via spacer in accordance with the present invention. Preferred embodiments of fatty diacids are saturated fatty diacids optionally substituted by one or more, preferably one, $C_{1-32}$ alkyl, one or more, preferably one, phosphate group (HOP(O)(OH)O—), one or more, preferably one, phosphonate group (HOP(O)O—), one or more, preferably one, thiophosphate group (HOP(O)(SH)O—), one or more, preferably one, dithiophosphate group (HOP(S)(SH)O—), one or more, preferably one, diphosphate group (HO—P(O)(OH)—O—P(O)(OH)—O—), one or more, preferably one, triphosphate group (HO—P(O)(OH)—O—P(O)(OH)—O—P(O)(OH)—O—), one or more, preferably one, phenyl group (—$C_6H_5$), one or more, preferably one, phenyl group substituted with a halogen, preferably iodine, or a carboxylic group. Preferred examples include glutaric acid optionally substituted by one $C_{6-24}$ alkyl such 3-pentadecylglutaric acid (PDG).

The term "alkylphosphate moiety" as used herein refers to groups of $C_{3-32}$alkyl-O—P(O)(OH)—O—, wherein said $C_{3-32}$alkyl is independently selected from $C_{3-32}$alkyl as defined herein.

The term "alkylphosphonate moiety" as used herein refers to groups of $C_{3-32}$alkyl-O—P(O)—O—, wherein said $C_{3-32}$alkyl is independently selected from $C_{3-32}$alkyl as defined herein.

The term "alkyl", as used herein, refers to a straight or branched hydrocarbon chain radical consisting solely of carbon and hydrogen atoms, containing no unsaturation, having from one to thirty-two carbon atoms (e.g., ($C_{1-32}$) alkyl or $C_{1-32}$ alkyl), and which may be or typically is attached to the rest of the molecule by a single bond. Whenever it appears herein, a numerical range such as "1 to 32" refers to each integer in the given range. For example, "1 to 32 carbon atoms" means that the alkyl group may consist of 1 carbon atom, 2 carbon atoms, 3 carbon atoms, etc., up to and including 32 carbon atoms, although the definition is also intended to cover the occurrence of the term "alkyl" where no numerical range is specifically designated. Typical alkyl groups include, but are not limited to, methyl, ethyl, n-propyl, 1-methylethyl (interchangeably used with iso-propyl; interchangeably abbreviated herein as iPr or Pri), n-butyl, isobutyl, sec-butyl, isobutyl, tertiary butyl (interchangeably used with 1,1-dimethylethyl or tert-butyl), n-pentyl, isopentyl, neopentyl, hexyl, septyl, octyl, nonyl and decyl. Unless stated otherwise specifically in the specification, an alkyl group is optionally substituted by one or more of substituents which are independently alkenyl, alkoxy, carboxylic group (—COOH), heteroalkyl, heteroalkenyl, hydroxyl, phosphate group (—OP(O)(OH)O—), phosphonate group (—OP(O)O—), phenyl group (—$C_6H_4$) optionally substituted with a halogen, preferably iodine, or a carboxylic group. Preferably, the term "alkyl", as used herein, refers to an unsubstituted alkyl as defined herein.

The term "alkylene", as used herein, refers to a straight or branched hydrocarbon chain bi-radical derived from alkyl, as defined herein, wherein one hydrogen of said alkyl is cleaved off generating the second radical of said alkylene. Examples of alkylene are, by way of illustration, —$CH_2$—, —$CH_2$—$CH_2$—, —CH($CH_3$)—, —$CH_2$—$CH_2$—$CH_2$—, —CH($CH_3$)—$CH_2$—, or —CH($CH_2CH_3$)—.

The term "alkenyl", as used herein, refers to a straight or branched hydrocarbon chain radical group consisting solely of carbon and hydrogen atoms, containing at least one double bond, and having from 3 to 32 carbon atoms (i.e., ($C_{3-32}$)alkenyl or $C_{3-32}$ alkenyl), which may be or typically is attached to the rest of the molecule by a single bond. Whenever it appears herein, a numerical range such as "3 to 32" refers to each integer in the given range—e.g., "3 to 32 carbon atoms" means that the alkenyl group may consist of 3 carbon atoms, 4 carbon atoms, etc., up to and including 32 carbon atoms. Typical alkenyl groups include, but are not limited to ethenyl (i.e., vinyl), prop-1-enyl (i.e., allyl), but-1-enyl, pent-1-enyl and penta-1,4-dienyl. Each double bond can be of either the (E)- or (Z)-configuration. Alkenyl, thus, may include, if applicable, either each of said double bond in its (E)-configuration, in its (Z)-configuration and mixtures thereof in any ratio. Unless stated otherwise specifically in the specification, an alkenyl group is optionally substituted by one or more of substituents which are independently alkenyl, alkoxy, carboxylic group (—COOH), heteroalkyl, heteroalkenyl, hydroxyl, phosphate group (—OP(O)(OH)O—), phosphonate group (—OP(O)O—), phenyl group (—$C_6H_4$) optionally substituted with a halogen, preferably iodine, or a carboxylic group. Preferably, the term "alkenyl", as used herein, refers to an unsubstituted alkenyl as defined herein.

The term "alkenylene", as used herein, refers to a straight or branched hydrocarbon chain bi-radical derived from alkenyl, as defined herein, wherein one hydrogen of said alkenyl is cleaved off generating the second radical of said alkenylene.

The term "alkynyl" refers to a straight or branched hydrocarbon chain radical group consisting solely of carbon and hydrogen atoms, containing at least one triple bond, having from two to ten carbon atoms (i.e., ($C_{2-32}$)alkynyl or $C_{2-32}$ alkynyl). Whenever it appears herein, a numerical range such as "2 to 32" refers to each integer in the given range—e.g., "2 to 32 carbon atoms" means that the alkynyl group may consist of 2 carbon atoms, 3 carbon atoms, etc., up to and including 32 carbon atoms. Typical alkynyl groups include, but are not limited to ethynyl, propynyl, butynyl, pentynyl and hexynyl. Unless stated otherwise specifically in the specification, an alkynyl group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—$C_6H_4$) optionally substituted with a halogen, preferably iodine, or a carboxylic group. Preferably, the term "alkynyl", as used herein, refers to an unsubstituted alkynyl as defined herein.

The term "alkynylene", as used herein, refers to a straight or branched hydrocarbon chain bi-radical derived from alkynyl, as defined herein, wherein one hydrogen of said alkynyl is cleaved off generating the second radical of said alkynylene.

The term "alkoxy" refers to the group —O-alkyl, including from 1 to 32 carbon atoms of a straight, branched configuration and combinations thereof attached to the parent structure through an oxygen. Examples include, but are not limited to, methoxy, ethoxy, propoxy, isopropoxy, cyclopropyloxy and cyclohexyloxy. "Lower alkoxy" refers to alkoxy groups containing one to six carbons, also referred to as ($C_{1-6}$)alkoxy or O—$C_{1-6}$alkyl.

The term "substituted alkoxy" refers to alkoxy wherein the alkyl constituent is substituted (i.e., —O-(substituted alkyl)). Unless stated otherwise specifically in the specification, the alkyl moiety of an alkoxy group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—$C_6H_4$) optionally substituted with a halogen, preferably iodine, or a carboxylic group.

The term "acyl" refers to the groups (alkyl)-C(O)—, (aryl)-C(O)—, (heteroaryl)-C(O)—, and (heteroalkyl)-C(O)—, wherein the group is attached to the parent structure through the carbonyl functionality. Unless stated otherwise specifically in the specification, the alkyl, aryl or heteroaryl moiety of the acyl group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—$C_6H_4$) optionally substituted with a halogen, preferably iodine, or a carboxylic group.

The terms "amino" or "amine" refers to a —$N(R^a)_2$ radical group, where each $R^a$ is independently hydrogen, alkyl, fluoroalkyl, carbocyclyl, carbocyclylalkyl, aryl, aralkyl, heterocycloalkyl, heterocycloalkylalkyl, heteroaryl or heteroarylalkyl, unless stated otherwise specifically in the specification. When a —$N(R^a)_2$ group has two $R^a$ substituents other than hydrogen, they can be combined with the nitrogen atom to form a 4-, 5-, 6- or 7-membered ring. For example, —$N(R^a)_2$ is intended to include, but is not limited to, 1-pyrrolidinyl and 4-morpholinyl. Unless stated otherwise specifically in the specification, an amino or amine group is optionally substituted by one or more of substituents which are independently alkenyl, carboxylic group (—COOH), heteroalkyl, heteroalkenyl, phosphate group (—OP(O)(OH)O—), phosphonate group (—OP(O)O—), phenyl group (—$C_6H_4$) optionally substituted with a halogen, preferably iodine, or a carboxylic group.

The terms "aromatic" or "aryl" or "Ar" refers to an aromatic radical with six to ten ring atoms (e.g., $C_6$-$C_{10}$ aromatic or $C_6$-$C_{10}$aryl) which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Whenever it appears herein, a numerical range such as "6 to 10" refers to each integer in the given range; e.g., "6 to 10 ring atoms" means that the aryl group may consist of 6 ring atoms, 7 ring atoms, etc., up to and including 10 ring atoms. The term includes monocyclic or fused-ring polycyclic (i.e., rings which share adjacent pairs of ring atoms) groups.

The terms "aralkyl" or "arylalkyl" refers to an (aryl)alkyl-radical where aryl and alkyl are as disclosed herein and which are optionally substituted by one or more of the substituents described as suitable substituents for aryl and alkyl respectively.

The term "carboxyl" or "carboxylic", as interchangeably used herein, refers to a —(C=O)OH radical.

The term "cycloalkyl" refers to a monocyclic or polycyclic radical that contains only carbon and hydrogen, and may be saturated, or partially unsaturated. Cycloalkyl groups include groups having from 3 to 10 ring atoms (i.e. ($C_{3-10}$) cycloalkyl or $C_{3-10}$cycloalkyl). Whenever it appears herein, a numerical range such as "3 to 10" refers to each integer in the given range—e.g., "3 to 10 carbon atoms" means that the cycloalkyl group may consist of 3 carbon atoms, etc., up to and including 10 carbon atoms. Illustrative examples of cycloalkyl groups include, but are not limited to the following moieties: cyclopropyl, cyclobutyl, cyclopentyl, cyclopentenyl, cyclohexyl, cyclohexenyl, cycloheptyl, cyclooctyl, cyclononyl, cyclodecyl, norbornyl, and the like.

The term "fluoroalkyl" refers to an alkyl radical, as defined above, that is substituted by one or more fluoro radicals, as defined above, for example, trifluoromethyl, difluoromethyl, 2,2,2-trifluoroethyl, 1-fluoromethyl-2-fluoroethyl, and the like. The alkyl part of the fluoroalkyl radical may be optionally substituted as defined above for an alkyl group.

The term "halogen", as used herein, refers to fluorine, chlorine, bromine, or iodine, preferably iodine. In a preferred embodiment, the halogen substituent is iodine.

The terms "heteroalkyl," and "heteroalkenyl", as used herein, refer to optionally substituted alkyl and alkenyl radicals and which have one or more skeletal chain atoms selected from an atom other than carbon, e.g., oxygen, nitrogen, sulfur, phosphorus or combinations thereof. A numerical range may be given, e.g., $C_1$-$C_4$ heteroalkyl, which refers to the chain length in total, which in this example is 4 atoms long.

The terms "heteroaryl" or "heteroaromatic" or "HetAr" refers to a 5- to 18-membered aromatic radical (e.g., $C_5$-$C_{13}$heteroaryl) that includes one or more ring heteroatoms selected from nitrogen, oxygen and sulfur, and which may be a monocyclic, bicyclic, tricyclic or tetracyclic ring system. Whenever it appears herein, a numerical range such as "5 to 18" refers to each integer in the given range—e.g., "5 to 18 ring atoms" means that the heteroaryl group may consist of 5 ring atoms, 6 ring atoms, etc., up to and including 18 ring atoms. Bivalent radicals derived from univalent heteroaryl radicals whose names end in "-yl" by removal of one hydrogen atom from the atom with the free valence are named by adding "-idene" to the name of the corresponding univalent radical—e.g., a pyridyl group with two points of attachment is a pyridylidene.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994.

The symbols (*), (#) and (§) in a chemical formula designates i) a point of attachment, ii) a radical, and/or iii) an unshared electron.

The term "antisense oligonucleotide (AON)", as used herein, refers to an oligonucleotide or oligomeric compound that is capable of interacting with and/or hybridizing to a pre-mRNA or an mRNA having a complementary nucleotide sequence thereby modifying gene expression.

The term "protecting group", as used herein, is intended to mean a group that selectively blocks one or more reactive sites in a multifunctional compound such that a chemical reaction can be carried out selectively on another unprotected reactive site and the group can then be readily removed or deprotected after the selective reaction is complete. A variety of protecting groups are disclosed, for example, in *Protecting Groups in Organic Synthesis*, T. W. Greene and P. G. M. Wuts, 3$^{rd}$ edition, John Wiley & Sons, New York 1999.

The terms "protecting group for an amino", "protecting group for an amino group", or "amino protecting group" as interchangeably used herein, are well known in the art and include those described in detail in *Protecting Groups in Organic Synthesis*, T. W. Greene and P. G. M. Wuts, 3$^{rd}$ edition, John Wiley & Sons, New York (1999), Greene's Protective Groups in Organic Synthesis, P. G. M. Wuts, 5$^{th}$ edition, John Wiley & Sons, (2014), and in *Current Protocols in Nucleic Acid Chemistry*, edited by S. L. Beaucage et al. June 2012, and hereby in particular in Chapter 2. Suitable "amino protecting groups" for the present invention include and are typically and preferably independently at each occurrence selected from methyl carbamate, ethyl carbamate, 9-fluorenylmethyl carbamate (Fmoc), 9-(2-sulfo)fluorenylmethyl carbamate, 2,7-di-t-butyl-[9-(10,10-dioxo-10,10, 10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1,1-dimethyl-2,2-dibromoethyl carbamate (DB-t-BOC), 1,1-dimethyl-2,2,2-trichloroethyl carbamate (TCBOC), benzyl carbamate (Cbz), p-methoxybenzyl carbamate (Moz) and 2,4, 6-trimethylbenzyl carbamate, (4-Methoxyphenyl) diphenylmethyl (MMTr); as well as formamide, acetamide, benzamide.

The terms "protecting group for a hydroxyl", "protecting group for a hydroxyl group", or "hydroxyl protecting group" as interchangeably used herein, are well known in the art and includes those described in detail in *Protecting Groups in Organic Synthesis*, T. W. Greene and P. G. M. Wuts, 3$^{rd}$ edition, John Wiley & Sons, New York (1999); Greene's Protective Groups in Organic Synthesis, P. G. M. Wuts, 5$^{th}$ edition, John Wiley & Sons, (2014), and in *Current Protocols in Nucleic Acid Chemistry*, edited by S. L. Beaucage et al. June 2012, and hereby in particular in Chapter 2. In a certain embodiment, the "hydroxyl protecting groups" of the present invention include and, typically and preferably are independently at each occurrence selected from, acetyl, benzoyl, benzyl, β-methoxyethoxymethyl ether (MEM), dimethoxytrityl, [bis-(4-methoxyphenyl)phenylmethyl] (DMTr), methoxymethyl ether (MOM), methoxytrityl [(4-methoxyphenyl)diphenylmethyl] (MMT), p-methoxybenzyl ether (PMB), methylthiomethyl ether, pivaloyl (Piv), tetrahydropyranyl (THP), tetrahydrofuran (THF), trityl (triphenylmethyl, Tr), silyl ether, such as t-Butyldiphenylsilyl ether (TBDPS), trimethylsilyl (TMS), tert-butyldimethylsilyl (TBDMS), tri-iso-propylsilyloxymethyl (TOM), and triisopropylsilyl (TIPS) ethers; methyl ethers, ethoxyethyl ethers (EE).

Preferred examples of the "hydroxyl protecting groups" of the present invention include and are independently at each occurrence selected from, acetyl, t-butyl, t-butoxymethyl, methoxymethyl, tetrahydropyranyl, 1-ethoxyethyl, 1-(2-chloroethoxy)ethyl, 2-trimethylsilylethyl, p-chlorophenyl, 2,4-dinitrophenyl, benzyl, benzoyl, p-phenylbenzoyl, 2,6-dichlorobenzyl, diphenylmethyl, p-nitrobenzyl, triphenylmethyl (trityl), 4,4'-dimethoxytrityl, trimethylsilyl, triethylsilyl, t-butyldimethylsilyl (TBDMS), t-butyldiphenylsilyl (TBDPS), triphenylsilyl, triisopropylsilyl, benzoylformate, chloroacetyl, trichloroacetyl, trifluoroacetyl, pivaloyl, 9-fluorenylmethyl carbonate, mesylate, tosylate, triflate, 4-monomethoxytrityl (MMTr), 4,4'dimethoxytrityl, (DMTr) and 4,4,4-trimethoxytrityl (TMTr), 2-cyanoethyl (CE or Cne), 2-(trimethylsilyl)ethyl (TSE), 2-(2-nitrophenyl)ethyl, 2-(4-cyanophenyl)ethyl 2-(4-nitrophenyl)ethyl (NPE), 2-(4-nitrophenylsulfonyl)ethyl, 3,5-dichlorophenyl, 2,4-dimethylphenyl, 2-nitrophenyl, 4-nitrophenyl, 2,4,6-trimethylphenyl, 2-(2-nitrophenyl)ethyl, butylthiocarbonyl, 4,4',4"-tris(benzoyloxy)trityl, diphenylcarbamoyl, levulinyl, 2-(dibromomethyl)benzoyl (Dbmb), 2-(isopropylthiomethoxymethyl)benzoyl (Ptmt), 9-phenylxanthen-9-yl (pixyl) or 9-(p-methoxyphenyl)xanthine-9-yl (MOX).

The term "nucleobase", as used herein, and abbreviated as Bx, refers to unmodified or naturally occurring nucleobases as well as modified or non-naturally occurring nucleobases and synthetic mimetics thereof. A nucleobase is any heterocyclic base that contains one or more atoms or groups of atoms capable of hydrogen bonding to a heterocyclic base of a nucleic acid.

Typical and preferred examples of the nucleobase is a purine base or a pyrimidine base, wherein preferably said purine base is purine or substituted purine, and said pyrimidine base is pyrimidine or substituted pyrimidine. More preferably, the nucleobase is (i) adenine (A), (ii) cytosine (C), (iii) 5-methylcytosine (MeC), (iv) guanine (G), (v) uracil (U), or (vi) 5-methyluracil (MeU), or to a derivative of (i), (ii), (iii), (iv), (v) or (vi). The terms "derivative of (i), (ii), (iii), (iv), (v) or (vi), and "nucleobase derivative" are used herein interchangeably. Derivatives of (i), (ii), (iii), (iv), (v) or (vi), and nucleobase derivatives, respectively, are known to the skilled person in the art and are described, for example, in Sharma V. K. et al., Med. Chem. Commun., 2014, 5, 1454-1471, and include without limitation 5-hydroxymethyl cytosine, xanthine, hypoxanthine, 2-aminoadenine, alkyl adenine, such as 6-methyl adenine, 2-propyl adenine, alkyl guanine, such as 6-methyl guanine, 2-propyl guanine, 2-thiouracil, 2-thiothymine and 2-thiocytosine, 5-halo uracil, 5-halo cytosine, alkynyl pyrimidine bases, such as 5-propynyl (—C≡C—CH$_3$) uracil, 5-propynyl (—C≡C—CH$_3$) cytosine, 6-azo uracil, 6-azo cytosine, 6-azo thymine, pseudo-uracil, 4-thiouracil; 8-substituted purine bases, such as 8-halo-, 8-amino-, 8-thiol-, 8-thioalkyl-, 8-hydroxyl-adenine or guanine, 5-substituted pyrimidine bases, such as 5-halo-, particularly 5-bromo-, 5-trifluoromethyl-uracil or -cytosine; 7-methylguanine, 7-methyladenine, 2-F-adenine, 2-amino-adenine, 8-azaguanine and 8-azaadenine, 7-deazaguanine, 7-deazaadenine, 3-deazaguanine, 3-deazaadenine, hydrophobic bases, promiscuous bases, size-expanded bases, or fluorinated bases. In certain embodiments, the nucleobase includes without limitation tricyclic pyrimidines, such as 1,3-diazaphenoxazine-2-one, 1,3-diazaphenothiazine-2-one or 9-(2-aminoethoxy)-1,3-diazaphenoxazine-2-one (G-clamp). The term "nucleobase derivative" also includes those in which the purine or pyrimidine base is replaced by other heterocycles, for example 7-deaza-adenine, 7-deazaguanosine, 2-aminopyridine or 2-pyridone. Further nucleobases of the invention include without limitation those known to skilled artisan (e.g. U.S. Pat. No. 3,687,808; Swayze et al., The Medicinal Chemistry of Oligonucleotides, in Antisense a Drug Technology, Chapter 6, pp. 143-182 (Crooke, S. T., ed., 2008); The Concise Encyclopedia Of Polymer Science And Engineering, Kroschwitz, J. I., Ed., John Wiley & Sons, 1990, pp. 858-859; Englisch et al., Angewandte Chemie, International Edition, 1991, Vol. 30 (6), pp. 613-623; Sanghvi, Y. S., Antisense Research and Applications, Crooke, S. T. and Lebleu, B., Eds., CRC Press, 1993, pp. 273-302). The term "nucleobase derivative" also includes those in which the purine or pyrimidine base is substituted with a moiety corresponding to the spacer of the present invention, in particular, for linking said one or more lipid moiety internally of said oligomeric compound, preferably said oligonucleotide. The specific linkages of said moiety corresponding to the spacer are known to the skilled person in the art. Preferred nucleobase derivatives include methylated adenine, guanine, uracil and cytosine and nucleobase derivatives, preferably of (i), (ii), (iii) or (iv), wherein the respective amino groups, preferably the exocyclic amino groups, are protected by acyl protecting groups or dialkylformamidino, preferably dimethylformamidino (DMF), and further include nucleobase derivatives such as 2-fluorouracil, 2-fluorocytosine, 5-bromouracil, 5-iodouracil, 2,6-diaminopurine, azacytosine and pyrimidine analogs such as pseudoisocytosine and pseudouracil. The preparation of modified nucleobases is known in the art and is described in U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,750,692; 5,830,653; 5,763,588; 6,005,096; and 5,681,941.

The term "internucleosidic linkage group", as used herein, refers to any linkage group known in the art that is able to link, preferably links, said tricyclo-deoxyribonucleic acid (tc-DNA) nucleoside either to a further tc-DNA nucleoside, a nucleoside other than a tc-DNA nucleoside, a non-nucleoside including a peptide, protein. Representative patents that teach such possible linkage groups are without limitation U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608. The term "internucleosidic linkage group", thus, includes phosphorus linkage groups and non-phosphorus linkage groups. Non-phosphorus linkage groups do not contain a phosphorus atom and examples of non-phosphorus linkage groups include, and are typically and preferably selected from alkyl, aryl, preferably, phenyl, benzyl, or benzoyl, cycloalkyl, alkylenearyl, alkylenediaryl, alkoxy, alkoxyalkylene, alkylsulfonyl, alkyne, ether, each independently of each other optionally substituted with cyano, nitro, halogen; carboxyl, amide, amine, amino, imine, thiol, sulfide, sulfoxide, sulfone, sulfamate, sulfonate, sulfonamide, siloxane or mixtures thereof. Typically and preferably, said internucleosidic linkage group is a phosphorus linkage group, and said phosphorus linkage group refers to a moiety comprising a phosphorus atom in the $P^{III}$ or $P^V$ valence state. Further preferably, said internucleosidic linkage group is a phosphorus linkage group. Again further preferably, said internucleosidic linkage group is selected from a phosphodiester linkage group, a phosphotriester linkage group, a phosphorothioate linkage group, a phosphorodithioate linkage group, a phosphonate linkage group, preferably a H-phosphonate linkage group or a methylphosphonate linkage group; a phosphonothioate linkage group, preferably a H-phosphonothioate linkage group, a methyl phosphonothioate linkage group; a phosphinate linkage group, a phosphorthioamidate linkage, a phosphoramidate linkage group, or a phosphite linkage group. In another very preferred embodiment, said internucleosidic linkage group is selected from a phosphodiester linkage group, a phosphotriester linkage group, a phosphorothioate linkage group, or a phosphonate linkage group, wherein the phosphonate is preferably a H-phosphonate linkage group or methylphosphonate linkage group.

As used herein, the term "nucleoside" refers to a compound comprising a nucleobase and a sugar covalently linked to said nucleobase. Further, the term "nucleoside" is meant to include all manner of naturally occurring or modified nucleosides or nucleoside mimetics that can be incorporated into an oligomer using natural or chemical oligomer synthesis. Typically and preferably, the term "nucleoside", as used herein, refers to a naturally occurring nucleoside, a modified nucleoside or nucleoside mimetic. The term "modified nucleosides" is intended to include modifications made to the sugar and/or nucleobase of a nucleoside as known to the skilled person in the art and described herein. The term "nucleoside mimetic" is intended to include those structures used to replace the sugar and the nucleobase. Examples of nucleoside mimetics include nucleosides wherein the nucleobase is replaced with a phenoxazine moiety (for example the 9-(2-aminoethoxy)-1,3-diazaphenoxazine-2-one group) and the sugar moiety is replaced a cyclohexenyl or a bicyclo[3.1.0]hexyl moiety. The term "nucleoside" also includes combinations of modifications, such as more than one nucleobase modification, more than one sugar modification or at least one nucleobase and at least one sugar modification.

The sugar of the nucleoside includes without limitation a monocyclic, bicyclic or tricyclic ring system, preferably a tricyclic or bicyclic system or a monocyclic ribose or de(s)oxyribose. Modifications of the sugar further include but are not limited to modified stereochemical configurations, at least one substitution of a group or at least one deletion of a group. A modified sugar is typically and preferably a modified version of the ribosyl moiety as naturally occurring in RNA and DNA (i.e. the furanosyl moiety), such as bicyclic sugars, tetrahydropyrans, 2'-modified sugars, 3'-modified sugars, 4'-modified sugars, 5'-modified sugars, or 4'-substituted sugars. Examples of suitable sugar modifications are known to the skilled person and include, but are not limited to 2', 3' and/or 4' substituted nucleosides (e.g. 4'-S-modified nucleosides); 2-O-modified RNA nucleotide residues, such as 2'-O-alkyl or 2'-O-(substituted)alkyl e.g. 2'-O-methyl, 2'-O-(2-cyanoethyl), 2'-O-(2-methoxy)ethyl (2'-MOE), 2'-O-(2-thiomethyl)ethyl; 2'-O-(haloalkoxy)methyl e.g. 2'-O-(2-chloroethoxy)methyl (MCEM), 2'-O-(2,2-dichloroethoxy)methyl (DCEM); 2'-O-alkoxycarbonyl e.g. 2'-O-[2-(methoxycarbonyl)ethyl] (MOCE), 2'-O-[2-(N-methylcarbamoyl)ethyl] (MCE), 2'-O-[2-(N,N-dimethylcarbamoyl)ethyl] (DMCE), in particular a 2'-O-methyl modification or a 2'-O-methoxyethyl (2'-O-MOE); or other modified sugar moieties, such as morpholino (PMO), cationic morpholino (PMOPlus) or a modified morpholino group, such as PMO-X. The term "PMO-X" refers to a modified morpholino group comprising at least one 3' or 5' terminal modification, such 3'-fluorescent tag, 3' quencher (e.g. 3'-carboxyfluorescein, 3'-Gene Tools Blue, 3'-lissamine, 3'-dabcyl), 3'-affinity tag and functional groups for chemical linkage (e.g. 3'-biotin, 3'-primary amine, 3'-disulfide amide, 3'-pyridyl dithio), 5'-end modifications (5'-primary amine, 5'-dabcyl), 3'-azide, 3'-alkyne, 5'-azide, 5'-alkyne, or as disclosed in WO2011/150408 and US2012/0065169.

"Bicyclic sugar moieties" comprise two interconnected ring systems, e.g. bicyclic nucleosides wherein the sugar moiety has a 2'-O—CH(alkyl)-4' or 2'-O—CH2-4' group, locked nucleic acid (LNA), xylo-LNA, alpha-L-LNA, beta-D-LNA, cEt (2'-0,4'-C constrained ethyl) LNA, cMOEt (2'-0,4'-C constrained methoxyethyl) LNA, ethylene-bridged nucleic acid (ENA), hexitol nucleic acid (HNA), fluorinated HNA (F-HNA), pyranosyl-RNA (p-RNA), or 3'-deoxypyranosyl-DNA (p-DNA).

In a preferred embodiment, the oligomeric compound is an oligonucleotide. The term "oligonucleotide", as used herein, refers to a compound comprising at least two nucleosides linked to each other each by a internucleosidic linkage group. Thus, the term "oligonucleotide", as used herein, includes, and typically and preferably refer to, oligomeric compounds comprising at least two nucleosides linked by internucleosidic linkage groups, wherein said at least two nucleosides are independently selected from naturally occurring nucleosides, modified nucleosides or nucleoside mimetics.

The oligomeric compound can be single stranded or double stranded. In one embodiment, the oligomeric compound is double stranded (i.e. a duplex). In a preferred embodiment, the oligomeric compound is single stranded.

In a preferred embodiment, said one or more lipid moiety is independently of each other linked to said oligomeric compound at (i) a terminal residue of said oligomeric compound, (ii) the 5' terminus of said oligomeric compound, (iii) the 3' terminus of said oligomeric compound; (iv) an internal residue of said oligomeric compound.

The term "terminus" refers to the end or terminus of the oligomeric compound, wherein the integer (3', 5, etc.) indicates to the carbon atom of the sugar included in the nucleoside of the oligomeric compound. The term "5' terminal group" or "3' terminal group", as used herein, refers to a group located at the 5' terminus or 3' terminus, respectively.

The term "natural" or "naturally occurring", as interchangeably used herein, refers to compounds that are of natural origin.

The term "complementary" refers to a nucleic acid molecule that can form hydrogen bond(s) with another nucleic acid molecule by either traditional Watson-Crick base pairing or other non-traditional types of pairing (e.g., Hoogsteen or reversed Hoogsteen hydrogen bonding) between complementary nucleosides or nucleotides. "Complementary" (or "specifically hybridizable") are terms that indicate a sufficient degree of complementarity or precise pairing such that stable and specific binding occurs between an oligomeric compound and a pre-mRNA or mRNA target. It is understood in the art that a nucleic acid molecule need not be 100% complementary to a target nucleic acid sequence to be specifically hybridizable. That is, two or more nucleic acid molecules may be less than fully complementary. Complementarity may be indicated by a percentage of contiguous residues in a nucleic acid molecule that can form hydrogen bonds with a second nucleic acid molecule. For example, if a first nucleic acid molecule has 10 nucleotides and a second nucleic acid molecule has 10 nucleotides, then base pairing of 5, 6, 7, 8, 9, or 10 nucleotides between the first and second nucleic acid molecules represents 50%, 60%, 70%, 80%, 90%, and 100% complementarity, respectively. "Perfectly" or "fully" complementary nucleic acid molecules means those in which all the contiguous residues of a first nucleic acid molecule will hydrogen bond with the same number of contiguous residues in a second nucleic acid molecule, wherein the nucleic acid molecules either both have the same number of nucleotides (i.e., have the same length) or the two molecules have different lengths.

The term "exon skipping" refers to the modification of pre-mRNA splicing by the targeting of splice donor and/or acceptor sites within a pre-mRNA with one or more complementary antisense oligonucleotides or oligomeric compounds. By blocking access of a spliceosome to one or more splice donor or acceptor sites, or any other site within an exon or intron involved in the definition of splicing, an oligonucleotide can prevent a splicing reaction and cause the deletion of exons from a fully-processed mRNA. Exon skipping is achieved in the nucleus during the maturation process of pre-mRNAs. Exon skipping includes the masking of key sequences involved in the splicing of targeted exons by using antisense oligonucleotides that are complementary to splice donor sequences within a pre-mRNA. For example, the inventive compositions comprising said oligomeric compounds provided herein may be suitably employed for exon skipping through the masking of splice sites at intron/exon junctions within a dystrophin pre-mRNA thereby facilitating the deletion of a mutant exon during the processing of the pre-mRNA to a mature mRNA.

The term "exon inclusion" refers to oligonucleotide-mediated processes such as the base-pairing of antisense oligonucleotides to a target pre-mRNA to block an exonic or intronic splicing enhancer and block the corresponding splicing repressor and/or disrupt an unfavorable secondary structure, resulting in more efficient recognition of the exon by the spliceosome and restoration of exon expression.

The term "in vivo" refers to an event that takes place in a subject's body.

The term "in vitro" refers to an event that takes places outside of a subject's body. In vitro assays encompass cell-based assays in which cells alive or dead are employed and may also encompass a cell-free assay in which no intact cells are employed.

The term "effective amount" or "therapeutically effective amount" refers to that amount of a compound or combination of compounds as described herein that is sufficient to effect the intended application including, but not limited to, disease treatment. A therapeutically effective amount may vary depending upon the intended application (in vitro or in vivo), or the human subject and disease condition being treated (e.g., the weight, age and gender of the subject), the severity of the disease condition, the manner of administration, etc. which can readily be determined by one of ordinary skill in the art. The term also applies to a dose that will induce a particular response in target cells (e.g., the reduction of platelet adhesion and/or cell migration). The specific dose will vary depending on the particular compounds chosen, the dosing regimen to be followed, whether the compound is administered in combination with other compounds, timing of administration, the tissue to which it is administered, and the physical delivery system in which the compound is carried.

A "therapeutic effect" as that term is used herein, encompasses a therapeutic benefit and/or a prophylactic benefit in a human subject. A prophylactic effect includes delaying or eliminating the appearance of a disease or condition, delaying or eliminating the onset of symptoms of a disease or condition, slowing, halting, or reversing the progression of a disease or condition, or any combination thereof.

The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts, preferably said pharmaceutically acceptable salt is the sodium salt.

In case of hydroxyl groups (OH) or thiol groups (SH) typically and preferably bound to P(III) or P(V) and present in said one or more lipid moiety, typically and preferably as part of the group B of said one or more lipid moiety, or present in said spacer, or present in said oligomeric compound, preferably in said oligonucleotide, of the present invention, as part of said internucleosidic linkage group, typically and preferably selected from phosphorothioate or phosphorodiester, each of said hydroxyl groups (OH) or thiol groups (SH) can independently of each other be present as said OH group or in its ionic state such as the O-anion and a pharmaceutically acceptable cation, or as said SH group or in its ionic state such as the S-anion and a pharmaceutically acceptable cation. Further included are any combinations and any states of equilibrium between the aforementioned situations in the inventive compositions, in particular taking further oxygen or sulfur-containing groups on said P(III) or P(V) such as (=O), (=S), another OH or SH group, into account, which is known by the skilled person in the art. For sake of simplicity, in the aspects and embodiments of the present invention, typically only one of the aforementioned situations is described. By way of example, a preferred spacer of the present invention is indicated herein as #-NH-$C_{2-12}$alkylene-OP(O)(SH)-§. Included herein is, as indicated without limitation, the spacer where the hydrogen is located at the oxygen, thus, #-NH-$C_{2-12}$alkylene-OP (OH)(S)-§ and all of the pharmaceutically acceptable salt thereof.

Thus, a pharmaceutically acceptable salt in the context of hydroxyl groups (OH) and or thiol groups (SH) typically and preferably bound to P(III) or P(V) and present in said one or more lipid moiety, typically and preferably as part of the group B of said one or more lipid moiety, or present in said spacer, or present in said oligomeric compound, preferably in said oligonucleotide, of the present invention, as part of said internucleosidic linkage group, typically and preferably selected from phosphorothioate or phosphorodiester, refers to the inventive compositions in which one or more of said OH groups or said SH groups are independently of each other be present as said OH group or in its ionic state such as the O-anion and a pharmaceutically acceptable cation thereof, or as said SH group or in its ionic state such as the S-anion and a pharmaceutically acceptable cation, and wherein typically and preferably said pharmaceutically acceptable cation is selected from protonated trimethylamine, protonated diethylamine, protonated methylamine, ammonium, sodium or potassium, further preferably wherein said pharmaceutically acceptable cation is sodium.

"Pharmaceutically acceptable carrier" or "pharmaceutically acceptable excipient" is intended to include any and all solvents, dispersion media, coatings, antibacterial and antifungal agents, isotonic and absorption delaying agents, and inert ingredients. The use of such pharmaceutically acceptable carriers or pharmaceutically acceptable excipients for active pharmaceutical ingredients is well known in the art. Except insofar as any conventional pharmaceutically accept-able carrier or pharmaceutically acceptable excipient is incompatible with the active pharmaceutical ingredient, its use in the therapeutic compositions of the invention is contemplated. Additional active pharmaceutical ingredients, such as other drugs, can also be incorporated into the described compositions and methods.

When ranges are used herein to describe, for example, physical or chemical properties such as molecular weight or chemical formulae, all combinations and sub-combinations of ranges and specific embodiments therein are intended to be included. Use of the term "about" when referring to a number or a numerical range means that the number or numerical range referred to is an approximation within experimental variability (or within statistical experimental error), and thus the number or numerical range may vary. The variation is typically from 0% to 15%, from 0% to 10%, from 0% to 5% of the stated number or numerical range.

In a first aspect, the present invention provides for a composition comprising an oligomeric compound comprising one or more tricyclo-deoxyribonucleic acid (tc-DNA) nucleosides and one or more lipid moiety, preferably exactly one lipid moiety, wherein said one or more lipid moiety is covalently linked to said oligomeric compound either directly or via a spacer, and wherein preferably said oligomeric compound comprises from 5 to 40 monomer subunits.

Tc-DNA Nucleosides

In an embodiment, the tc-DNA nucleosides of the oligomeric compounds of the inventive compositions comprise a compound of Formula (1):

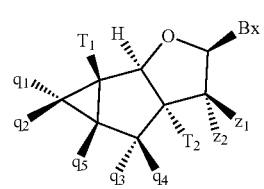

Formula (1)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety;
$q_1$, $q_2$, $q_3$, $q_4$ and $q_5$ are each independently selected from the group consisting of hydrogen (H), halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and —($CH_2$)$_n$—C(O)—$R_6$', wherein n is 0 to 6 and wherein $R_6$' is selected from the group consisting of OH, $NH_2$, O—$C_{1-32}$lkyl and NH—$C_{1-32}$alkyl;
$z_1$ and $z_2$ are each independently selected from the group consisting of H, halogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl;
or a pharmaceutically-acceptable salt thereof.

In an embodiment, the tc-DNA nucleosides of the oligomeric compounds of the inventive compositions comprise a compound of Formula (1), wherein $q_5$ is H.

In an embodiment, the tc-DNA nucleosides of the oligomeric compounds of the inventive compositions comprise a compound of Formula (1), wherein Bx is selected from the group consisting of thymine, adenine, guanine, and cytosine.

In an embodiment, the tc-DNA nucleosides of the oligomeric compounds of the inventive compositions comprise a compound of Formula (1), wherein Bx is a modified base. In an embodiment, the tc-DNA nucleosides of the oligomeric compounds of the invention comprise a compound of Formula (1), wherein Bx is a modified base selected from the group consisting of 5-methylcytosine, 5-bromouracil, inosine, and 2,6-diaminopurine.

In an embodiment, the tc-DNA nucleosides of the oligomeric compounds of the inventive compositions comprise a compound of Formula (2):

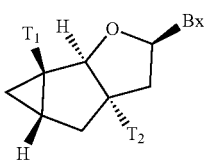

Formula (2)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the tc-DNA nucleosides of the oligomeric compounds of the inventive compositions comprise a compound of Formula (2), wherein Bx is selected from the group consisting of thymine, adenine, guanine, and cytosine. In an embodiment, the tc-DNA nucleosides of the oligomeric compounds of the invention comprise a compound of Formula (2), wherein Bx is a modified base. In an embodiment, the tc-DNA nucleosides of the oligomeric compounds of the invention comprise a compound of Formula (2), wherein Bx is a modified base selected from the group consisting of 5-methylcytosine, 5-bromouracil, inosine, and 2,6-diaminopurine.

In an embodiment, the tc-DNA nucleosides of the oligomeric compounds of the inventive compositions comprise a compound of Formula (3) (also known as a C(6')-functionalized tc-DNA):

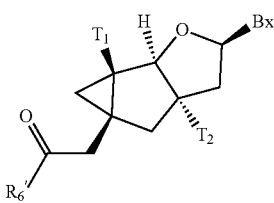

Formula (3)

wherein:
Bx is a nucleobase;
$R_{6'}$ is selected from the group consisting of OH, $NH_2$, O—$C_{1-32}$alkyl and NH—$C_{1-32}$alkyl; one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the tc-DNA nucleosides of the oligomeric compounds of the inventive compositions comprise a compound of Formula (3), wherein Bx is selected from the group consisting of thymine, adenine, guanine, and cytosine. In an embodiment, the tc-DNA nucleosides of the oligomeric compounds of the invention comprise a compound of Formula (3), wherein Bx is a modified base. In an embodiment, the tc-DNA nucleosides of the oligomeric compounds of the invention comprise a compound of Formula (3), wherein Bx is a modified base selected from the group consisting of 5-methylcytosine, 5-bromouracil, inosine, and 2,6-diaminopurine.

In an embodiment, the tc-DNA nucleosides of the oligomeric compounds of the inventive compositions comprise a compound of Formula (4) (also known as 6'-fluoro-tc-DNA):

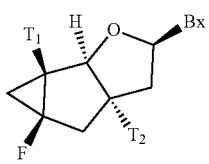

Formula (4)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the tc-DNA nucleosides of the oligomeric compounds of the inventive compositions comprise a compound of Formula (4), wherein Bx is selected from the group consisting of thymine, adenine, guanine, and cytosine. In an embodiment, the tc-DNA nucleosides of the oligomeric compounds of the invention comprise a compound of Formula (4), wherein Bx is a modified base. In an embodiment, the tc-DNA nucleosides of the oligomeric compounds of the invention comprise a compound of Formula (4), wherein Bx is a modified base selected from the group consisting of 5-methylcytosine, 5-bromouracil, inosine, and 2,6-diaminopurine.

In an embodiment, the tc-DNA nucleosides of the oligomeric compounds of the inventive compositions comprise a compound of Formula (5) (also known as 2'-fluoro-tc-DNA):

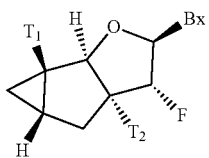

Formula (5)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the tc-DNA nucleosides of the oligomeric compounds of the inventive compositions comprise a compound of Formula (5), wherein Bx is selected from the group consisting of thymine, adenine, guanine, and cytosine. In an embodiment, the tc-DNA nucleosides of the oligomeric compounds of the invention comprise a compound of Formula (5), wherein Bx is a modified base. In an embodiment, the tc-DNA nucleosides of the oligomeric compounds of the invention comprise a compound of Formula (5), wherein Bx is a modified base selected from the group consisting of 5-methylcytosine, 5-bromouracil, inosine, and 2,6-diaminopurine.

Thus, in an embodiment, said one or more nucleosides tc-DNA nucleosides of the oligomeric compounds of the inventive compositions comprise a compound of Formula (5') (also known as 2'-fluoro-tc-ANA):

Formula (5')

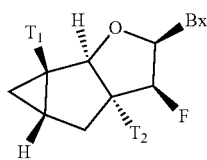

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the tc-DNA nucleosides of the oligomeric compounds of the inventive compositions comprise a compound of Formula (5'), wherein Bx is selected from the group consisting of thymine, adenine, guanine, and cytosine. In an embodiment, the tc-DNA nucleosides of the oligomeric compounds of the invention comprise a compound of Formula (5'), wherein Bx is a modified base. In an embodiment, the tc-DNA nucleosides of the oligomeric compounds of the invention comprise a compound of Formula (5'), wherein Bx is a modified base selected from the group consisting of 5-methylcytosine, 5-bromouracil, inosine, and 2,6-diaminopurine.

General methods of preparation of compounds of Formula (1) and Formula (2) for use with oligomeric compounds are known in the art, including the methods described in U.S. Patent Application Publication Nos. 2015/0141637, 2016/0002280, and 2014/0296323, the disclosures of which are incorporated by reference herein. Standard phosphoramidite building blocks for tc-DNA have been described in the art, e.g., in Steffens and Leumann, *Helv. Chim. Acta* 1997, 80, 2426-2439. Methods of preparing compounds of Formula (3) have been described, e.g., in Lietard and Leumann, *J. Org. Chem.* 2012, 77, 4566-77, the disclosure of which is incorporated by reference herein. Methods of preparing compounds of Formula (4) have been described, e.g., in Medvecky, Istrate, and Leumann, *J. Org. Chem.* 2015, 80, 3556-65, the disclosure of which is incorporated by reference herein. Methods of preparing compounds of Formula (5) and (5') have been described, e.g., in Istrate, Medvecky, and Leumann, *Org. Lett.* 2015, 17, 1950-53, the disclosure of which is incorporated by reference herein.

2'-Modified RNA Nucleosides and Other Nucleosides

In an embodiment, said oligomeric compound further comprises one or more nucleosides other than tc-DNA nucleosides, wherein said one or more nucleosides other than tc-DNA nucleosides are independently of each other 2'-modified ribonucleic acid (2'-modified-RNA) nucleosides.

In an embodiment, the one or more nucleosides other than tc-DNA nucleosides of the oligomeric compounds of the invention is an RNA nucleoside of Formula (6) (a RNA nucleoside):

Formula (6)

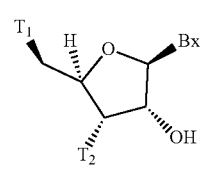

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the one or more nucleosides other than tc-DNA nucleosides of the oligomeric compounds of the invention is an RNA nucleoside of Formula (6), wherein Bx is selected from the group consisting of cytosine, adenine, guanine, and uracil. In an embodiment, the 2'-modified-RNA nucleosides of the oligomeric compounds of the invention comprise a compound of Formula (6), wherein Bx is a modified base. In an embodiment, the 2'-modified-RNA nucleosides of the oligomeric compounds of the invention comprise a compound of Formula (6), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the preferred inventive compositions comprise a compound of Formula (7) (a 2'-O-methyl-RNA nucleoside):

Formula (7)

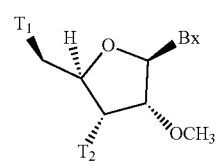

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (7), wherein Bx is selected from the group consisting of cytosine, adenine, guanine, and uracil. In an embodiment, the 2'-modified-RNA nucleosides of the oligomeric compounds of the invention comprise a compound of Formula (7), wherein Bx is a modified base. In an embodiment, the 2'-modified-RNA nucleosides of the oligomeric compounds of the invention comprise a compound of Formula (7), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (8) (a 2'-O-propargyl-RNA nucleoside):

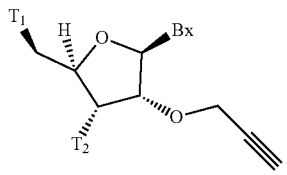

Formula (8)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (8), wherein Bx is selected from the group consisting of cytosine, adenine, guanine, and uracil. In an embodiment, the 2'-modified-RNA nucleosides of the oligomeric compounds of the invention comprise a compound of Formula (8), wherein Bx is a modified base. In an embodiment, the 2'-modified-RNA nucleosides of the oligomeric compounds of the invention comprise a compound of Formula (8), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (9) (a 2'-O-propylamino-RNA nucleoside):

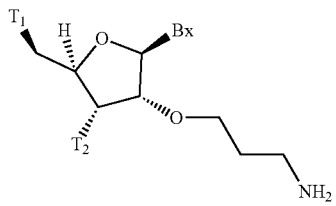

Formula (9)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (9), wherein Bx is selected from the group consisting of cytosine, adenine, guanine, and uracil. In an embodiment, the 2'-modified-RNA nucleosides of the oligomeric compounds of the invention comprise a compound of Formula (9), wherein Bx is a modified base. In an embodiment, the 2'-modified-RNA nucleosides of the oligomeric compounds of the invention comprise a compound of Formula (9), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (10) (a 2'-amino-RNA nucleoside):

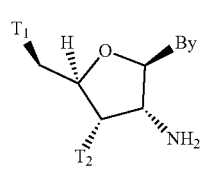

Formula (10)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (10), wherein Bx is selected from the group consisting of cytosine, adenine, guanine, and uracil. In an embodiment, the 2'-modified-RNA nucleosides of the oligomeric compounds of the invention comprise a compound of Formula (10), wherein Bx is a modified base. In an embodiment, the 2'-modified-RNA nucleosides of the oligomeric compounds of the invention comprise a compound of Formula (10), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (11) (a 2'-fluoro-RNA nucleoside):

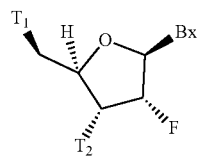

Formula (11)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (11), wherein Bx is selected from the group consisting of cytosine, adenine, guanine, and uracil. In an embodiment, the 2'-modified-RNA nucleosides of the oligomeric compounds of the invention comprise a compound of Formula (11), wherein Bx is a modified base. In an embodiment, the 2'-modified-RNA nucleosides of the oligomeric compounds of the invention comprise a compound of Formula (11), wherein Bx is a modified base selected from the group consisting of 5-methylcytosine, 5-methyluracil, 5-bromouracil, inosine, and 2,6-diaminopurine.

In an embodiment, the one or more nucleosides other than tc-DNA nucleosides of the oligomeric compounds of the invention comprise a compound of Formula (11') (a 2'-deoxy 2'-fluoro-arabino nucleoside (2'-FANA):

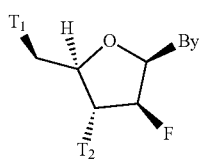

Formula (11')

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the one or more nucleosides other than tc-DNA nucleosides of the oligomeric compounds of the invention comprise a compound of Formula (11'), wherein Bx is selected from the group consisting of cytosine, adenine, guanine, and uracil. In an embodiment, the 2'-modified-RNA nucleosides of the oligomeric compounds of the invention comprise a compound of Formula (11'), wherein Bx is a modified base. In an embodiment, the 2'-modified-RNA nucleosides of the oligomeric compounds of the invention comprise a compound of Formula (11'), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (12) (a 2'-O-methoxyethyl-RNA, or 2'-MOE, nucleoside):

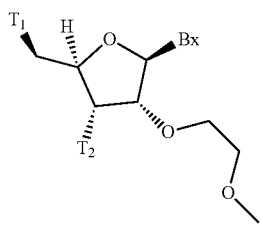

Formula (12)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (12), wherein Bx is selected from the group consisting of cytosine, adenine, guanine, and uracil. In an embodiment, the 2'-modified-RNA nucleosides of the oligomeric compounds of the invention comprise a compound of Formula (12), wherein Bx is a modified base. In an embodiment, the 2'-modified-RNA nucleosides of the oligomeric compounds of the invention comprise a compound of Formula (12), wherein Bx is a modified base selected from the group consisting of 5-methylcytosine, 5-methyluracil, 5-bromouracil, inosine, and 2,6-diaminopurine.

In an embodiment, the one or more nucleosides other than tc-DNA nucleosides of the oligomeric compounds of the invention comprise a compound of Formula (13) comprise a compound of Formula (13) (a morpholino nucleoside):

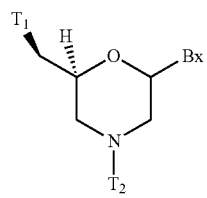

Formula (13)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the one or more nucleosides other than tc-DNA nucleosides of the oligomeric compounds of the invention comprise a compound of Formula (13), wherein Bx is selected from the group consisting of cytosine, adenine, guanine, and uracil. In an embodiment, the 2'-modified-RNA nucleosides of the oligomeric compounds of the invention comprise a compound of Formula (13), wherein Bx is a modified base. In an embodiment, the 2'-modified-RNA nucleosides of the oligomeric compounds of the invention comprise a compound of Formula (13), wherein Bx is a modified base selected from the group consisting of 5-methylcytosine, 5-methyluracil, 5-bromouracil, inosine, and 2,6-diaminopurine.

In an embodiment, the 2'-modified-RNA nucleosides of the oligomeric compounds of the invention comprise a compound of Formula (14) (a locked nucleic acid or LNA nucleoside):

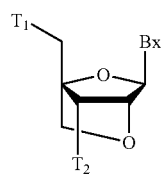

Formula (14)

wherein:
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety.

In an embodiment, the 2'-modified-RNA nucleosides of the oligomeric compounds of the invention comprise a compound of Formula (14), wherein Bx is selected from the group consisting of cytosine, adenine, guanine, and uracil. In an embodiment, the 2'-modified-RNA nucleosides of the oligomeric compounds of the invention comprise a compound of Formula (14), wherein Bx is a modified base. In an embodiment, the 2'-modified-RNA nucleosides of the oligomeric compounds of the invention comprise a compound of Formula (14), wherein Bx is a modified base selected from the group consisting of 5-methylcytosine, 5-methyluracil, 5-bromouracil, inosine, and 2,6-diaminopurine.

General methods of preparation of compounds of Formula (6) to Formula (14) for use with oligomeric compounds are known in the art, including the methods described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847; and 6,600,032; U.S. Patent Application Publication Nos. 2015/0141637, 2016/0002280, and 2014/0296323; and Renneberg, et al., *J Am. Chem. Soc.* 2002, 124, 5993-6002, the disclosures of which are incorporated by reference herein.

In an embodiment, said oligomeric compound further comprises one or more nucleosides other than tc-DNA nucleosides, wherein said one or more nucleosides other than tc-DNA nucleosides are independently of each other selected from
  (i) ribonucleic acid (RNA) nucleosides;
  (ii) deoxyribonucleic acid (DNA) nucleosides;
  (iii) 2'-modified-RNA nucleosides
  (iv) bicyclic nucleic acid (2',4'-BNA) nucleosides, preferably selected from 2',4'-BNA having a 2'-O—N—C bridged system (2',4'-BNA$^{NC}$), stereoisomer of LNA-α-L-LNA and Ethylene nucleic acid (ENA) nucleosides;
  (v) peptide nucleic acids (PNAs) nucleosides;
  (vi) 2'-deoxy 2'-fluoro-arabino (FANA) nucleosides;
  (vii) hexitol nucleic acids (HNAs) nucleosides; and
  (viii) phosphorodiamidate morpholino (PMO) nucleosides.

Further nucleosides useful for the present invention are known for the skilled person in the art such as other lipophilic 2'-O-alkyl RNA as described in Biochemistry 2005, 44, 9045-9057.

Non-Nucleosides

In an embodiment, the oligomeric compounds of the invention comprise non-nucleosides, also known in the art as non-nucleoside linkers, non-nucleotide linkers, and non-nucleotidylic linkers, which are highly flexible substitutes for the sugar carbons of, e.g., a ribofuranone moiety, and which can be used to replace the tc-DNA nucleosides and the nucleosides other than the tc-DNA nucleosides of the present oligomeric compounds. An exemplary non-nucleotide is the 1,3-propanediol group shown in Formula (15), which is shown joining two exemplary phosphorodiester internucleosidic linkages:

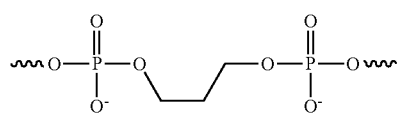

Formula (15)

The wavy lines in Formula (15) signify additional oligomeric repeating nucleoside and internucleosidic linkages units as described herein.

The non-nucleotides of the present invention may be used with any of the internucleosidic linkages described herein, including embodiments wherein the phosphorodiester internucleosidic linkages shown in Formula (15) are replaced with one or more phosphorothioate internucleosidic linkages.

In an embodiment, a non-nucleotide is a 1,3-propanediol group. The synthesis and incorporation of 1,3-propanediol groups into oligomeric compounds is known in the art and is described, e.g., in Seela and Kaiser, *Nuc. Acids Res.* 1987, 15, 3113-29. In an embodiment, the oligomeric compounds of the invention include 1, 2, 3, 4, 5, 6, 7, 8, 9, 10, 11, or 12 1,3-propanediol groups linked by phosphorothioate internucleosidic linkages, phosphorodiester internucleosidic linkages, or mixtures thereof.

Alternative non-nucleosides may also be used with the oligomeric compounds of the present invention, such as ethylene glycol oligomers of various lengths (i.e., one, two, three, or more ethylene glycol units joined to form a single non-nucleoside). Various suitable ethylene glycol groups are described, e.g., in Pils and Micura, *Nuc. Acids Res.* 2000, 28, 1859-63. The synthesis and use of non-nucleosides has also been described in, e.g., U.S. Pat. No. 5,573,906, the disclosure of which is incorporated by reference herein Internucleosidic Linkage Groups In an embodiment, the internucleosidic linkage group of the oligomeric compounds of the invention is independently selected from the group consisting of a phosphorothioate linkage, a phosphorodithioate linkage, a phosphorodiester linkage, a phosphotriester linkage, an aminoalkylphosphotriester linkage, a methyl phosphonate linkage, an alkyl phosphonate linkage, a 5'-alkylene phosphonate linkage, a phosphonate linkage, a phosphinate linkage, a phosphoramidate linkage, an 3'-aminophosphoramidate linkage, an aminoalkyl phosphoramidate linkage, a thionophosphoramidate linkage, a thionoalkylphosphonate linkage, a thionoalkylphosphotriester linkage, a selenophosphate linkage, and a boranophosphate linkage.

In a preferred embodiment, the internucleosidic linkages of the oligomeric compounds of the invention are independently selected from the group consisting of a phosphorothioate linkage and a phosphorodiester linkage. In an embodiment, the internucleosidic linkages of the oligomeric compounds of the invention comprise only phosphorodiester linkages.

An exemplary phosphorothioate linkage is shown in Formula (16):

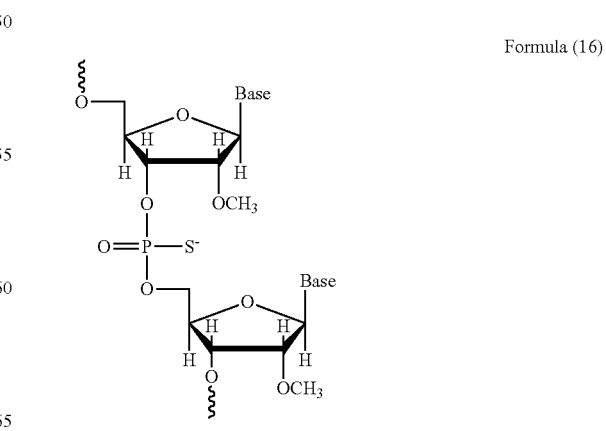

Formula (16)

An exemplary phosphorodiester linkage is shown in Formula (17):

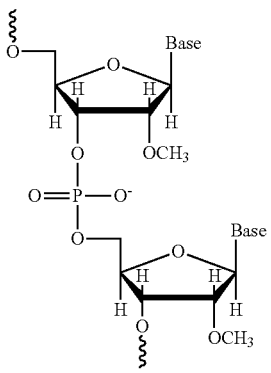

Formula (17)

The wavy lines in Formula (16) and Formula (17) represent additional oligomeric repeating nucleoside and internucleosidic linkages as described herein.

General methods of preparation of internucleosidic linkages for use with oligomeric compounds are known in the art, including the methods described in U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein. Phosphorothioates may be prepared from phosphate triesters, for example, using phenylacetyl disulfide (PADS) chemistry described in Krotz, et al., *Org. Proc. R&D* 2004, 8, 852-58, as part of solid-phase syntheses using, e.g., the four-reaction 3'- to 5'-elongation cycle (detritylation, coupling, sulfurization using PADS, and capping, followed by deprotection, cleavage from the support, and purification steps.

The term "phosphorus moiety", as used herein, refers to a moiety comprising a phosphorus atom in the $P^{III}$ or $P^V$ valence state and which is represented by Formula (18)

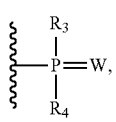

Formula (18)

$R_4$ Formula (18), wherein

W represents O, S or Se or W represents an electron pair; $R_3$ and $R_4$ are independently of each other H, halogen, OH, $OR_5$, $NR_6R_7$, SH, $SR_5$, $C_1$-$C_6$alkyl, $C_1$-$C_6$haloalkyl, $C_1$-$C_6$alkoxy, $C_1$-$C_6$haloalkoxy, $C_1$-$C_6$aminoalkyl; wherein $R_5$ is $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl, each independently of each other optionally substituted with cyano, nitro, halogen, $C_1$-$C_4$alkoxy, $C_1$-$C_4$haloalkyl, $C_1$-$C_4$haloalkoxy, NHC(O)$C_1$-$C_3$alkyl, NHC(O)$C_1$-$C_3$haloalkyl, $C_1$-$C_3$alkylsulfonyl; acetyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl optionally substituted with cyano, nitro, halogen, $C_1$-$C_3$alkyl, $C_1$-$C_3$alkoxy; an amino protecting group; or together with the nitrogen atom to which they are attached form a heterocyclic ring, wherein preferably said heterocyclic ring is selected from pyrolidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein the wavy line indicates the attachment to the oxygen of said $OR_2$ group in any one of Formulas (1) to (14) or in analogous manner for nucleosides not explicitly shown herein by formula. When W represents O, S or Se then said P atom within said phosphorus moiety is in its $P^V$ valence state. When W represents an electron pair then said P atom within said phosphorus moiety is in its $P^{III}$ valence. The moiety of Formula (18) includes any possible stereoisomer. Further included in said moieties represented by Formula (18) are salts thereof, wherein typically and preferably said salts are formed upon treatment with inorganic bases or amines, and are typically and preferably salts derived from reaction with the OH or SH groups being (independently of each other) said $R_3$ and $R_4$. Preferred inorganic bases or amines leading to said salt formation with the OH or SH groups are well known in the art and are typically and preferably trimethylamine, diethylamine, methylamine or ammonium hydroxide. These phosphorus moieties included in the present invention are, if appropriate, also abbreviated as "O-HB+", wherein said HB+ refers to the counter cation formed.

The term "phosphorus moiety", as used herein, includes and, typically and preferably is independently at each occurrence selected from a moiety derived from phosphonates, phosphite triester, monophosphate, diphosphate, triphosphate, phosphate triester, phosphate diester, thiophosphate ester, di-thiophosphate ester or phosphoramidites. Thus, in an embodiment, said $OR_2$ in any one of the Formula (1) to (14) or in analogous manner for nucleosides not explicitly shown herein by formula, is independently at each occurrence selected from phosphonates, phosphite triester, monophosphate, diphosphate, triphosphate, phosphate triester, phosphate diester, thiophosphate ester, di-thiophosphate ester or phosphoramidites. Further phosphorus moieties usable in the present invention are disclosed in Tetrahedron Report Number 309 (Beaucage and Iyer, Tetrahedron, 1992, 48, 2223-2311), the disclosure of which is incorporated herein by reference.

The term "phosphorus moiety", as used herein, preferably refers to a group $R_2$ as defined in any one of the Formula (1) to (14) or in analogous manner for nucleosides not explicitly shown herein by formula, comprising a phosphorus atom in the $P^{III}$ or $P^V$ valence state and which is represented independently at each occurrence either by Formula (19), Formula (20) or Formula (21),

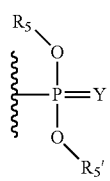

Formula (19)

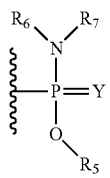

Formula (20)

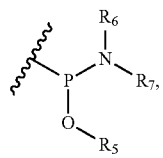

Formula (21)

wherein Y is O, S or Se, and wherein Y preferably is O or S, more preferably Y is O; and wherein $R_5$ and $R_{5'}$ are independently at each occurrence and of each other hydrogen, $C_1$-$C_9$alkyl, $C_1$-$C_6$alkoxy, each independently of each other optionally substituted with cyano, nitro, halogen, —NHC(O)$C_1$-$C_3$alkyl, —NHC(O)$C_1$-$C_3$haloalkyl, $C_1$-$C_3$alkylsulfonyl; aryl, $C_1$-$C_6$alkylenearyl, $C_1$-$C_6$alkylenediaryl each independently of each other optionally substituted with cyano, nitro, halogen, $C_1$-$C_4$alkoxy, $C_1$-$C_4$haloalkyl, $C_1$-$C_4$haloalkoxy, —NHC(O)$C_1$-$C_3$alkyl, NHC(O)$C_1$-$C_3$haloalkyl, $C_1$-$C_3$alkylsulfonyl; a hydroxyl protecting group; wherein $R_6$ and $R_7$ are independently of each other hydrogen, $C_1$-$C_9$alkyl optionally substituted with cyano, nitro, halogen, $C_2$-$C_6$alkenyl, $C_3$-$C_6$cycloalkyl, $C_1$-$C_3$alkoxy; aryl, preferably phenyl, optionally substituted with cyano, nitro, halogen, $C_1$-$C_3$ alkyl, $C_1$-$C_3$alkoxy; an amino protecting group; or together with the nitrogen atom to which they are attached form a heterocyclic ring, wherein preferably said heterocyclic ring is selected from pyrolidinyl, piperidinyl, morpholinyl, piperazinyl and homopiperazine, wherein said heterocyclic ring is optionally substituted with $C_1$-$C_3$ alkyl; and wherein $R_8$ is a thiol protecting group; and wherein the wavy line indicates the attachment to the oxygen of said $OR_2$ group in any one of the Formula (1) to (5).

Compositions

Thus, in a first aspect, the present invention provides for a composition comprising an oligomeric compound comprising one or more tricyclo-deoxyribonucleic acid (tcDNA) nucleosides and one or more lipid moiety, preferably exactly one lipid moiety, wherein said one or more lipid moiety is covalently linked to said oligomeric compound either directly or via a spacer, and wherein preferably said oligomeric compound comprises from 5 to 40 monomer subunits.

In one embodiment, said one or more lipid moiety is independently of each other selected from a fatty acid moiety, a fatty diacid moiety, a glycerolipid moiety, a glycerophospholipid moiety, a sphingolipid moiety, a phospholipid, an alkylphosphate moiety and an alkylphosphonate moiety.

In one embodiment, said one or more lipid moiety is independently of each other selected from a fatty acid moiety, a fatty diacid moiety, a phospholipid, an alkylphosphate moiety and an alkylphosphonate moiety.

In one preferred embodiment, said one or more lipid moiety is independently of each other a fatty acid moiety. In another preferred embodiment, said one or more lipid moiety is independently of each other a fatty diacid moiety. In another embodiment, said one or more lipid moiety is independently of each other a glycerolipid moiety. In another embodiment, said one or more lipid moiety is independently of each other a glycerophospholipid moiety. In another embodiment, said one or more lipid moiety is independently of each other a sphingolipid moiety. In another preferred embodiment, said one or more lipid moiety is independently of each other an alkylphosphate moiety. In another preferred embodiment, said one or more lipid moiety is independently of each other an alkylphosphonate moiety.

In one embodiment, the one or more lipid moiety is negatively charged at pH of 7.4, wherein typically said pH of 7.4 corresponds to the physiological pH.

In a preferred embodiment, said one or more lipid moiety is independently of each other selected from a fatty acid moiety, a fatty diacid moiety, an alkylphosphate moiety and an alkylphosphonate moiety.

In a preferred embodiment, said one or more lipid moiety is independently of each other a fatty acid moiety or a fatty diacid moiety.

In another preferred embodiment, said one or more lipid moiety is independently of each other a fatty acid moiety, wherein said fatty acid moiety is a saturated fatty acid moiety. In another preferred embodiment, said one or more lipid moiety is independently of each other a fatty acid moiety, wherein said fatty acid moiety is an unsaturated fatty acid moiety.

In a preferred embodiment, said one or more lipid moiety is independently of each other a fatty diacid moiety, wherein said fatty diacid moiety is a saturated fatty diacid moiety. In another preferred embodiment, said one or more lipid moiety is independently of each other a fatty diacid moiety, wherein said fatty acid moiety is an unsaturated fatty diacid moiety.

In a very preferred embodiment, said one or more lipid moiety is independently of each other a fatty acid moiety, wherein said fatty acid moiety is a saturated unbranched fatty acid moiety.

In a preferred embodiment, said one or more lipid moiety is independently of each other a fatty acid moiety, wherein said fatty acid moiety is derived from a saturated unbranched fatty acid. In a preferred embodiment, said one or more lipid moiety is independently of each other a fatty diacid moiety, wherein said fatty diacid moiety is derived from a saturated unbranched fatty diacid.

In a very preferred embodiment, said one or more lipid moiety is independently of each other a fatty acid moiety or a fatty diacid moiety, wherein said fatty acid moiety is a saturated unbranched fatty acid moiety, and wherein said fatty diacid moiety is a saturated unbranched fatty diacid moiety.

In a preferred embodiment, said one or more lipid moiety is independently of each other a moiety of formula (I)

A-B—* (I)

wherein A is $C_{3-32}$alkyl, $C_{3-32}$alkenyl, $C_{3-32}$alkynyl, HOOC—$C_{3-32}$alkylene, HOOC—$C_{3-32}$alkenylene or HOOC—$C_{3-32}$alkynylene, and B is C(O), OP(OH), OP(O)(OH), OP(O)(SH), NH—C(O), NH—P(O)(OH), NH—P(O)(SH) or a pharmaceutically acceptable salt thereof; and wherein said asterisk (*) represents the point of said covalent linkage to said oligomeric compound or to said spacer.

In a further preferred embodiment, said one or more lipid moiety is independently of each other selected from any one of the formula (a) to (u)
(a) $C_{3-32}$alkyl-C(O)—*,
(b) $C_{3-32}$alkenyl-C(O)—*,
(c) $C_{3-32}$alkynyl-C(O)—*,
(d) $C_{3-32}$alkyl-OP(OH)—*,
(e) $C_{3-32}$alkenyl-OP(OH)—*,
(f) $C_{3-32}$alkynyl-OP(OH)—*,
(g) $C_{3-32}$alkyl-OP(O)(OH)—*,
(h) $C_{3-32}$alkenyl-OP(O)(OH)—*,
(i) $C_{3-32}$alkynyl-OP(O)(OH)—*,
(j) $C_{3-32}$alkyl-OP(O)(SH)—*,
(k) $C_{3-32}$alkenyl-OP(O)(SH)—*,
(l) $C_{3-32}$alkynyl-OP(O)(SH)—*,
(m) $C_{3-32}$alkyl-NH—C(O)—*,
(n) $C_{3-32}$alkenyl-NH—C(O)—*,
(o) $C_{3-32}$alkynyl-NH—C(O)—*,
(p) $C_{3-32}$alkyl-NH—P(O)(OH)—*,
(q) $C_{3-32}$alkenyl-NH—P(O)(OH)—*,
(r) $C_{3-32}$alkynyl-NH—P(O)(OH)—*,
(s) HOOC—$C_{3-32}$alkylene-C(O)—*,
(t) HOOC—$C_{3-32}$alkenylene-C(O)—*, and
(u) HOOC—$C_{3-32}$alkynylene-C(O)—*,
wherein said asterisk (*) represents the point of said covalent linkage to said oligomeric compound or to said spacer.

In a preferred embodiment, said one or more lipid moiety is independently of each other a moiety of formula $C_{3-32}$alkyl-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkyl-OP(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-OP(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-OP(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkyl-OP(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-OP(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-OP(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkyl-OP(O)(SH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-OP(O)(SH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-OP(O)(SH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkyl-NH—C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-NH—C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-NH—C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkyl-NH—P(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkenyl-NH—P(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula $C_{3-32}$alkynyl-NH—P(O)(OH)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula HOOC—$C_{3-32}$alkylene-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula HOOC—$C_{3-32}$alkenylene-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety of formula HOOC—$C_{3-32}$alkynylene-C(O)—*, wherein said asterisk (*) represents the point of said covalent linkage to said oligomeric compound or to said spacer, wherein preferably said composition comprises exactly one lipid moiety.

In a preferred embodiment, said one or more lipid moiety is independently of each other a moiety from any one of the formula (a) and (b)
  (a) $C_{3-32}$alkyl-C(O)—*,
  (b) HOOC—$C_{3-32}$alkylene-C(O)—*,
  (c) $C_{3-32}$alkyl-OP(O)(OH)—*
  (d) $C_{3-32}$alkyl-OP(O)(SH)—*
wherein said asterisk (*) represents the point of said covalent linkage to said oligomeric compound or to said spacer, and wherein preferably said $C_{3-32}$alkyl is an unbranched $C_{3-32}$alkyl, and wherein further preferably said $C_{3-32}$alkyl is an unbranched $C_{3-32}$alkyl having an uneven number of carbon atoms, and wherein preferably said $C_{3-32}$alkylene is an unbranched $C_{3-32}$alkylene, and wherein further preferably said $C_{3-32}$alkylene is an unbranched $C_{3-32}$alkylene having an uneven number of carbon atoms.

In a further preferred embodiment, said one or more lipid moiety is independently of each other a moiety of formula $C_{3-32}$alkyl-C(O)—*, wherein said asterisk (*) represents the point of said covalent linkage to said oligomeric compound or to said spacer, and wherein preferably said $C_{3-32}$alkyl is an unbranched $C_{3-32}$alkyl, and wherein further preferably said $C_{3-32}$alkyl is an unbranched $C_{3-32}$alkyl having an uneven number of carbon atoms.

In a preferred embodiment, said one or more lipid moiety is independently of each other a moiety of formula $C_{3-32}$alkyl-C(O)—*, wherein said asterisk (*) represents the point of said covalent linkage to said oligomeric compound or to said spacer, wherein preferably said composition comprises exactly one lipid moiety, and wherein said $C_{3-32}$alkyl is an unbranched $C_{3-32}$alkyl.

In a preferred embodiment, said one or more lipid moiety is independently of each other a moiety of formula $C_{3-32}$alkyl-C(O)—*, wherein said asterisk (*) represents the point of said covalent linkage to said oligomeric compound or to said spacer, wherein preferably said composition comprises exactly one lipid moiety, and wherein said $C_{3-32}$alkyl is an unbranched $C_{3-32}$alkyl having an uneven number of carbon atoms.

In a preferred embodiment, said one or more lipid moiety is independently of each other a moiety of formula $C_{3-32}$alkenyl-C(O)—*, wherein said asterisk (*) represents the point of said covalent linkage to said oligomeric compound or to said spacer, and wherein preferably said $C_{3-32}$alkenyl is a branched $C_{3-32}$alkenyl, and wherein further preferably said $C_{3-32}$alkenyl is a branched $C_{3-32}$alkenyl having an uneven number of carbon atoms.

In a preferred embodiment, said one or more lipid moiety is independently of each other a moiety of formula $C_{3-32}$alkenyl-C(O)—*, wherein said asterisk (*) represents the point of said covalent linkage to said oligomeric compound or to said spacer, wherein preferably said composition comprises exactly one lipid moiety, and wherein said $C_{3-32}$alkenyl is a branched $C_{3-32}$alkenyl.

In a preferred embodiment, said one or more lipid moiety is independently of each other a moiety of formula $C_{3-32}$alkenyl-C(O)—*, wherein said asterisk (*) represents the point of said covalent linkage to said oligomeric compound or to said spacer, wherein preferably said composition comprises exactly one lipid moiety, and wherein said $C_{3-32}$alkenyl is a branched $C_{3-32}$alkenyl having an uneven number of carbon atoms.

In a further very preferred embodiment, said one or more lipid moiety is independently of each other a saturated $C_{8-26}$-fatty acid moiety, wherein preferably said saturated $C_{8-26}$-saturated fatty acid moiety is derived from caprylic acid (C8), capric acid (C10), lauric acid (C12), myristic acid (C14), palmitic acid (C16), stearic acid (C18), arachidic acid (C20), lignoceric acid (C22) or cerotic acid (C24).

In a further very preferred embodiment, said one or more lipid moiety is independently of each other a saturated fatty acid moiety, wherein said saturated fatty acid moiety is derived from caprylic acid (C8), capric acid (C10), lauric acid (C12), myristic acid (C14), palmitic acid (C16), stearic acid (C18), arachidic acid (C20), lignoceric acid (C22) and cerotic acid (C24).

In a further very preferred embodiment, said one or more lipid moiety is independently of each other a saturated fatty acid moiety derived from palmitic acid (C16) or stearic acid (C18), wherein preferably said one or more lipid moiety is a saturated fatty acid moiety derived from palmitic acid (C16).

In a further very preferred embodiment, said one or more lipid moiety is independently of each other an unsaturated $C_{14-22}$-fatty acid moiety, wherein preferably said unsaturated $C_{14-22}$-fatty acid moiety is derived from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid. In a further very preferred embodiment, said one or more lipid moiety is a saturated fatty acid moiety derived from palmitoleic acid.

In a further very preferred embodiment, said one or more lipid moiety is independently of each other an unsaturated fatty acid moiety, wherein said unsaturated fatty acid moiety is derived from myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid and docosahexaenoic acid.

In a further very preferred embodiment, said one or more lipid moiety is an unsaturated fatty acid moiety derived from oleic acid.

In a further very preferred embodiment, said one or more lipid moiety is independently of each other a moiety of formula (HOOC)—$C_{3-32}$alkylene-C(O)—*, wherein said asterisk (*) represents the point of said covalent linkage to said oligomeric compound or to said spacer, and wherein preferably said $C_{3-32}$alkylene is an unbranched $C_{3-32}$alkylene, and wherein further preferably said $C_{3-32}$alkylene is an unbranched $C_{3-32}$alkylene having an uneven number of carbon atoms.

In a further very preferred embodiment, said one or more lipid moiety is independently of each other a moiety of formula (HOOC)—$(CH_2)_r$—$(CH)(C_{5-25}$alkyl)-$(CH_2)_t$—C (O)—*, wherein said asterisk (*) represents the point of said covalent linkage to said oligomeric compound or to said spacer, wherein r is independently of each other an integer of 1 to 3, wherein t is independently of each other an integer of 1 to 3.

In a further very preferred embodiment, said one or more lipid moiety is independently of each other a moiety of formula, $(HOOC)—(CH_2)_r—(CH)[(CH_2)_sCH_3]—(CH_2)_t—C(O)—*$, wherein said asterisk (*) represents the point of said covalent linkage to said oligomeric compound or to said spacer, and wherein r is independently of each other an integer of 1 to 3, wherein s is independently of each other an integer of 4 to 24, wherein t is independently of each other an integer of 1 to 3.

In a further very preferred embodiment, said one or more lipid moiety is independently of each other a moiety of formula, $(HOOC)—(CH_2)_r—(CH)[(CH_2)_sCH_3]—(CH_2)_t—C(O)—*$, wherein said asterisk (*) represents the point of said covalent linkage to said oligomeric compound or to said spacer, and wherein r is independently of each other an integer of 1 or 2, wherein s is independently of each other an integer of 5 to 19, wherein t is independently of each other an integer of 1 or 2.

In a further very preferred embodiment, said one or more lipid moiety is independently of each other a moiety of formula, $(HOOC)—(CH_2)_r—(CH)[(CH_2)_sCH_3]—(CH_2)_t—C(O)—*$, wherein said asterisk (*) represents the point of said covalent linkage to said oligomeric compound or to said spacer, and wherein r is 1, wherein s is independently of each other an integer of 4 to 24, preferably 5 to 19, wherein t is 1.

In a further very preferred embodiment, said one or more lipid moiety is independently of each other a moiety of formula, $(HOOC)—(CH_2)_r—(CH)[(CH_2)_sCH_3]—(CH_2)_t—C(O)—*$, wherein said asterisk (*) represents the point of said covalent linkage to said oligomeric compound or to said spacer, and wherein r is 1, wherein s is independently of each other an integer of 5 to 19, preferably 11 to 17, wherein t is 1.

In a further very preferred embodiment, said one or more lipid moiety is independently of each other a moiety of formula, $(HOOC)—(CH_2)_r—(CH)[(CH_2)_sCH_3]—(CH_2)_t—C(O)—*$, wherein said asterisk (*) represents the point of said covalent linkage to said oligomeric compound or to said spacer, and wherein r is 1, wherein s is 15, wherein t is 1.

Thus, in a further very preferred embodiment, said one or more lipid moiety is 3-pentadecylglutaric acid (PDG).

In a further very preferred embodiment, said lipid moiety is linked directly to said oligomeric compound.

In a further very preferred embodiment, said one or more lipid moiety is linked to said oligomeric compound via a spacer.

In an embodiment, said spacer has from 5 to 30 C-atoms, preferably from 5 to 25 C-atoms, more preferably from 5 to 20 C-atoms, or most preferably from 5 to 17 C-atoms. In additional embodiments, said spacer has from 4 to 20 hetero-atoms, preferably from 4 to 18 hetero-atoms, more preferably from 4 to 14 hetero-atoms, or most preferably from 4 to 12 hetero-atoms. Particularly preferred examples of hetero-atoms are N-, and O-atoms. H-atoms are not hetero-atoms.

In a preferred embodiment, said spacer comprises, preferably is, independently selected from, any one of the formula
(a) #-NH—$C_{2-12}$alkylene-§,
(b) #-NH—$C_{2-12}$alkylene-OP(OH)-§,
(c) #-NH—$C_{2-12}$alkylene-OP(O)(SH)-§,
(d) #-NH—$C_{2-12}$alkylene-OP(O)(OH)-§,
(e) #-SH—$C_{2-12}$alkylene-§,
(f) #-NH—$C_{2-12}$alkylene-NH—C(O)-§,
(g) #-NH—$C_{2-12}$alkylene-NH—P(O)(OH)-§, and
(h) #-NH—$C_{2-12}$alkylene-NH—P(O)(SH)-§,
wherein one or more —$CH_2$-moieties in said $C_{2-12}$alkylene are optionally replaced independently by —O—, —S—, —NH—, —C(O)—, —C(O)O—, an aryl, a heteroaryl, a cycloalkyl, a heterocycloalkyl, —OP(OH)O—, OP(O)(SH)O—, OP(O)(OH)O—, NHP(O)(OH)O—, NHP(O)(SH)O—, or —(O—$CH_2$—$CH_2$)$_k$— with k being an integer of 1 to 8, and wherein one or more —$CH_2$-moieties in said $C_{2-12}$alkylene are independently of each other optionally substituted with one or more —COOH, —$NH_2$, —OP(O)(OH)$_2$ or —OH (and thus meaning that one or both, preferably one, of the hydrogen atoms in one or more of the —CH2-moieties in said $C_{2-12}$alkylene are independently of each other optionally substituted with one or more —COOH, —$NH_2$, —OP(O)(OH)$_2$ or —OH), and wherein said (#) represents the point of covalent linkage to said lipid moiety and said (§) represents the point of covalent linkage to said oligomeric compound.

In a very preferred embodiment, said spacer comprises, preferably is, independently selected from, any one of the formula
(a) #-NH—$C_{2-12}$alkylene-§,
(b) #-NH—$C_{2-12}$alkylene-OP(OH)-§,
(c) #-NH—$C_{2-12}$alkylene-OP(O)(SH)-§,
(d) #-NH—$C_{2-12}$alkylene-OP(O)(OH)-§,
(e) #-NH—$C_{2-12}$alkylene-NH—C(O)-§,
(f) #-NH—$C_{2-12}$alkylene-NH—P(O)(OH)-§, and
(g) #-NH—$C_{2-12}$alkylene-NH—P(O)(SH)-§,
wherein said (#) represents the point of covalent linkage to said lipid moiety and said (§) represents the point of covalent linkage to said oligomeric compound.

In a very preferred embodiment, said spacer comprises, preferably is, independently selected from, any one of the formula
(a) #-NH—$C_{2-12}$alkylene-§,
(b) #-NH—$C_{2-12}$alkylene-OP(OH)-§,
(c) #-NH—$C_{2-12}$alkylene-OP(O)(SH)-§,
(d) #-NH—$C_{2-12}$alkylene-OP(O)(OH)-§,
(e) #-NH—$C_{2-12}$alkylene-NH—C(O)-§,
(f) #-NH—$C_{2-12}$alkylene-NH—P(O)(OH)-§, and
(g) #-NH—$C_{2-12}$alkylene-NH—P(O)(SH)-§,
wherein one or more —$CH_2$-moieties in said $C_{2-12}$alkylene are optionally replaced independently by —O—, —S—, —NH—, —C(O)—, —C(O)O—, an aryl, a heteroaryl, a cycloalkyl, a heterocycloalkyl, —OP(OH)O—, OP(O)(SH)O—, OP(O)(OH)O—, NHP(O)(OH)O—, NHP(O)(SH)O—, or —(O—$CH_2$—$CH_2$)$_k$— with k being an integer of 1 to 8, and wherein said (#) represents the point of covalent linkage to said lipid moiety and said (§) represents the point of covalent linkage to said oligomeric compound.

In a very preferred embodiment, said spacer comprises, preferably is, independently selected from, any one of the formula
(a) #-NH—$C_{2-12}$alkylene-§,
(b) #-NH—$C_{2-12}$alkylene-OP(OH)-§,
(c) #-NH—$C_{2-12}$alkylene-OP(O)(SH)-§,
(d) #-NH—$C_{2-12}$alkylene-OP(O)(OH)-§,
(e) #-NH—$C_{2-12}$alkylene-NH—C(O)-§,
(f) #-NH—$C_{2-12}$alkylene-NH—P(O)(OH)-§, and
(g) #-NH—$C_{2-12}$alkylene-NH—P(O)(SH)-§,
wherein one or more —$CH_2$-moieties in said $C_{2-12}$alkylene are optionally replaced independently by —O—, —S—, —NH—, —C(O)—, —C(O)O—, an aryl, a heteroaryl, a cycloalkyl, a heterocycloalkyl, —OP(OH)O—, OP(O)(SH)O—, OP(O)(OH)O—, NHP(O)(OH)O—, NHP(O)(SH)O—, or —(O—CH$_2$—CH$_2$)$_k$— with k being an integer of 1 to 8, and wherein one or more —CH$_2$-moieties in said C$_{2-12}$alkylene are independently of each other optionally substituted with one or more —COOH, —NH$_2$, —OP(O)(OH)$_2$ or —OH, and wherein said (#) represents the point of covalent linkage to said lipid moiety and said (§) represents the point of covalent linkage to said oligomeric compound.

In a very preferred embodiment, said spacer comprises, preferably is, independently selected from, any one of the formula
(a) #-NH—C$_{2-12}$alkylene-§,
(b) #-NH—C$_{2-12}$alkylene-OP(OH)-§,
(c) #-NH—C$_{2-12}$alkylene-OP(O)(SH)-§,
(d) #-NH—C$_{2-12}$alkylene-OP(O)(OH)-§,
(e) #-NH—C$_{2-12}$alkylene-NH—C(O)-§,
(f) #-NH—C$_{2-12}$alkylene-NH—P(O)(OH)-§, and
(g) #-NH—C$_{2-12}$alkylene-NH—P(O)(SH)-§, wherein one or more —CH$_2$-moieties in said C$_{2-12}$alkylene are optionally replaced independently by —O—, —S—, —NH—, —C(O)—, —C(O)O—, phenyl, triazolyl, cyclopentyl, cyclohexyl, succinimidyl, —OP(OH)O—, OP(O)(SH)O—, OP(O)(OH)O—, NHP(O)(OH)O—, NHP(O)(SH)O—, or —(O—CH$_2$—CH$_2$)$_k$— with k being an integer of 1 to 8, and wherein one or more —CH$_2$-moieties in said C$_{2-12}$alkylene are independently of each other optionally substituted with one or more —COOH, —NH$_2$, —OP(O)(OH)$_2$ or —OH, and wherein said (#) represents the point of covalent linkage to said lipid moiety and said (§) represents the point of covalent linkage to said oligomeric compound.

In a further very preferred embodiment, said spacer comprises, preferably is, independently selected from any one of the formula:
(a) —NH—(CH$_2$)$_m$—,
(b) —NH—(CH$_2$)$_m$—X—,
(c) —NH—(CH$_2$)$_n$—(O—CH$_2$—CH$_2$)$_k$—O—(CH$_2$)$_p$—,
(d) —NH—(CH$_2$)$_n$—(O—CH$_2$—CH$_2$)$_k$—O—(CH$_2$)$_p$—X—,
(e) —NH—CH(COOH)—(CH$_2$)$_q$—,
(f) —NH—CH(COOH)—(CH$_2$)$_q$—X—,
(g) —NH—CH(COOH)—(CH$_2$)$_q$—C(O)—NH—(CH$_2$)$_m$—,
(h) —NH—CH(COOH)—(CH$_2$)$_q$—C(O)—NH—(CH$_2$)$_m$—X—,
(i) —NH—CH(COOH)—(CH$_2$)$_q$—C(O)—NH—(CH$_2$)$_n$—(O—CH$_2$—CH$_2$)$_k$—O—(CH$_2$)$_p$—X—,
(j) —NH—CH(COOH)—(CH$_2$)$_q$—C(O)—NH—(CH$_2$)$_n$—(O—CH$_2$—CH$_2$)$_k$—O—(CH$_2$)$_p$—C(O)—NH—(CH$_2$)$_n$—(O—CH$_2$—CH$_2$)$_r$X—, wherein X is independently of each other OP(OH), OP(O)(SH) or OP(O)(OH), wherein k is independently of each other an integer of 1 to 8, wherein m is independently of each other an integer of 2 to 12, wherein n is independently of each other an integer of 2 to 4, wherein p is independently of each other an integer of 1 to 5, wherein q is independently of each other an integer of 1 to 3, preferably 1 or 2, wherein r is independently of each other an integer of 1 to 3, preferably 1 or 2.

In a further very preferred embodiment, said spacer comprises, preferably is, independently selected from any one of the formula:
(a) #-NH—(CH$_2$)$_m$-§,
(b) #-NH—(CH$_2$)$_m$—X-§,
(c) #-NH—(CH$_2$)$_n$—(O—CH$_2$—CH$_2$)$_k$—O—(CH$_2$)$_p$-§,
(d) #-NH—(CH$_2$)$_n$—(O—CH$_2$—CH$_2$)$_k$—O—(CH$_2$)$_p$—X-§,
(e) #-NH—CH(COOH)—(CH$_2$)$_q$-§,
(f) #-NH—CH(COOH)—(CH$_2$)$_q$—X-§,
(g) #-NH—CH(COOH)—(CH$_2$)$_q$—C(O)—NH—(CH$_2$)$_m$-§,
(h) #-NH—CH(COOH)—(CH$_2$)$_q$—C(O)—NH—(CH$_2$)$_m$—X-§,
(i) #-NH—CH(COOH)—(CH$_2$)$_q$—C(O)—NH—(CH$_2$)$_n$—(O—CH$_2$—CH$_2$)$_k$—O—(CH$_2$)$_p$—X-§,
(j) #-NH—CH(COOH)—(CH$_2$)$_q$—C(O)—NH—(CH$_2$)$_n$—(O—CH$_2$—CH$_2$)$_k$—O—(CH$_2$)$_p$—C(O)—NH—(CH$_2$)$_n$—(O—CH$_2$—CH$_2$)$_r$—X-§, wherein X is independently of each other OP(OH), OP(OH)(S) or OP(O)(OH), wherein k is independently of each other an integer of 1 to 8, wherein m is independently of each other an integer of 2 to 12, wherein n is independently of each other an integer of 2 to 4, wherein p is independently of each other an integer of 1 to 5, wherein q is independently of each other an integer of 1 to 3, preferably 1 or 2, wherein r is independently of each other an integer of 1 to 3, preferably 1 or 2, and wherein said (#) represents the point of covalent linkage to said lipid moiety and said (§) represents the point of covalent linkage to said oligomeric compound.

In a further very preferred embodiment, said spacer comprises, preferably is, independently selected from any one of the formula
(a) —Z—NH—(CH$_2$)$_m$—X—
(b) —Z—NH—(CH$_2$)$_n$—(O—CH$_2$—CH$_2$)$_k$—O—(CH$_2$)$_p$—X—
(c) —Z[—NH—(CH$_2$)$_n$—(O—CH$_2$—CH$_2$)$_k$—O—(CH$_2$)$_p$—C(O)—]—NH—(CH$_2$)$_q$—X—
(d) —Z[—NH—(CH$_2$)$_n$—(O—CH$_2$—CH$_2$)$_k$—O—(CH$_2$)$_p$—C(O)—]$_r$—NH—(CH$_2$)$_q$—(O—CH$_2$—CH$_2$)$_k$—X— wherein —Z— represents independently of each other a bond or —NH—CH(COOH)—(CH$_2$)$_2$—C(O)— or —NH—CH[(CH$_2$)$_2$COOH]—C(O)—, wherein X is independently of each other OP(OH), OP(O)(SH), OP(O)(OH), NHP(O)(OH), NHP(O)(SH) or NH—C(O), wherein k is independently of each other an integer of 1 to 8, wherein m is independently of each other an integer of 2 to 12, wherein n is independently of each other an integer of 2 to 4, and wherein p is independently of each other an integer of 1 to 5, wherein q is independently of each other an integer of 1 to 6, preferably 3 or 6, wherein r is independently of each other an integer of 1 to 3, preferably 1 or 2.

In a further very preferred embodiment, said spacer comprises, preferably is, independently selected from any one of the formula
(a) #-Z—NH—(CH$_2$)$_m$—X-§
(b) #-Z—NH—(CH$_2$)$_n$—(O—CH$_2$—CH$_2$)$_k$—O—(CH$_2$)$_p$—X-§
(c) #-Z[—NH—(CH$_2$)$_n$—(O—CH$_2$—CH$_2$)$_k$—O—(CH$_2$)$_p$—C(O)—]—NH—(CH$_2$)$_q$—X-§
(d) #-Z[—NH—(CH$_2$)$_n$—(O—CH$_2$—CH$_2$)$_k$—O—(CH$_2$)$_p$—C(O)—]$_r$—NH—(CH$_2$)$_q$—(O—CH$_2$—CH$_2$)$_k$—X-§ wherein —Z— represents independently of each other a bond or —NH—CH(COOH)—(CH$_2$)$_2$—C(O)— or —NH—CH[(CH$_2$)$_2$COOH]—C(O)—, wherein X is independently of each other OP(OH), OP(O)(SH), OP(O)(OH), NHP(O)(OH), NHP(O)(SH) or NH—C(O), wherein k is independently of each other an integer of 1 to 8, wherein m is independently of each other an integer of 2 to 12, wherein n is independently of each other an integer of 2 to 4, and wherein p is independently of each other an integer of 1 to 5, wherein q is independently of each other an integer of 1 to 6, preferably 3 or 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§
- (c) #-Z[—NH—$(CH_2)_n$—(O—$CH_2$—$CH_2)_k$—O—$(CH_2)_p$—C(O)—]—NH—$(CH_2)_q$—X-§
- (d) #-Z[—NH—$(CH_2)_n$—(O—$CH_2$—$CH_2)_k$—O—$(CH_2)_p$—C(O)—]$_r$—NH—$(CH_2)_q$—(O—$CH_2$—$CH_2)_k$—X-§ wherein —Z— represents independently of each other a bond or —NH—CH(COOH)—$(CH_2)_2$—C(O)— or —NH—CH[$(CH_2)_2$COOH]—C(O)—, wherein X is independently of each other OP(OH), OP(O)(SH), OP(O)(OH), NHP(O)(OH), NHP(O)(SH) or NH—C(O), wherein k is independently of each other an integer of 1 or 2, wherein m is independently of each other an integer of 4 to 8, wherein n is independently of each other an integer of 2 to 4, and wherein p is independently of each other an integer of 1 or 2, wherein q is independently of each other an integer of 1 to 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§
- (c) #-Z[—NH—$(CH_2)_n$—(O—$CH_2$—$CH_2)_k$—O—$(CH_2)_p$—C(O)—]—NH—$(CH_2)_q$—X-§
- (d) #-Z[—NH—$(CH_2)_n$—(O—$CH_2$—$CH_2)_k$—O—$(CH_2)_p$—C(O)—]$_r$—NH—$(CH_2)_q$—(O—$CH_2$—$CH_2)_k$—X-§ wherein —Z— represents independently of each other a bond or —NH—CH(COOH)—$(CH_2)_2$—C(O)— or —NH—CH[$(CH_2)_2$COOH]—C(O)—, X is independently of each other OP(OH), OP(O)(SH) or OP(O)(OH), wherein k is independently of each other an integer of 1 or 2, wherein m is independently of each other an integer of 4 to 8, wherein n is 2, and wherein p is 1, wherein q is independently of each other an integer of 1 to 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§
- (c) #-Z[—NH—$(CH_2)_n$—(O—$CH_2$—$CH_2)_k$—O—$(CH_2)_p$—C(O)—]—NH—$(CH_2)_q$—X-§
- (d) #-Z[—NH—$(CH_2)_n$—(O—$CH_2$—$CH_2)_k$—O—$(CH_2)_p$—C(O)—]$_r$—NH—$(CH_2)_q$—(O—$CH_2$—$CH_2)_k$—X-§ wherein —Z— represents independently of each other a bond or —NH—CH(COOH)—$(CH_2)_2$—C(O)— or —NH—CH[$(CH_2)_2$COOH]—C(O)—, X is independently of each other OP(O)(SH) or OP(O)(OH), wherein k is independently of each other an integer of 1 or 2, wherein m is independently of each other an integer of 4 to 8, wherein n is 2, and wherein p is 1, wherein q is independently of each other an integer of 1 to 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another very preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§
- (c) #-Z[—NH—$(CH_2)_n$—(O—$CH_2$—$CH_2)_k$—O—$(CH_2)_p$—C(O)—]—NH—$(CH_2)_q$—X-§
- (d) #-Z[—NH—$(CH_2)_n$—(O—$CH_2$—$CH_2)_k$—O—$(CH_2)_p$—C(O)—]$_r$—NH—$(CH_2)_q$—(O—$CH_2$—$CH_2)_k$—X-§ wherein —Z— represents independently of each other a bond or —NH—CH(COOH)—$(CH_2)_2$—C(O)— or —NH—CH[$(CH_2)_2$COOH]—C(O)—, X is independently of each other OP(O)(SH), wherein k is independently of each other an integer of 1 or 2, wherein m is independently of each other an integer of 4 to 8, wherein n is 2, and wherein p is 1, wherein q is independently of each other an integer of 1 to 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another very preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§
- (c) #-Z[—NH—$(CH_2)_n$—(O—$CH_2$—$CH_2)_k$—O—$(CH_2)_p$—C(O)—]—NH—$(CH_2)_q$—X-§
- (d) #-Z[—NH—$(CH_2)_n$—(O—$CH_2$—$CH_2)_k$—O—$(CH_2)_p$—C(O)—]$_r$—NH—$(CH_2)_q$—(O—$CH_2$—$CH_2)_k$—X-§ wherein —Z— represents independently of each other a bond or —NH—CH(COOH)—$(CH_2)_2$—C(O)— or —NH—CH[$(CH_2)_2$COOH]—C(O)—, X is independently of each other OP(O)(OH), wherein k is independently of each other an integer of 1 or 2, wherein m is independently of each other an integer of 4 to 8, wherein n is 2, and wherein p is 1, wherein q is independently of each other an integer of 1 to 6, wherein r is independently of each other an integer of 1 to 3, preferably 1 or 2, and wherein said (#) represents the point of covalent linkage to said lipid moiety and said (§) represents the point of covalent linkage to said oligomeric compound.

In another very preferred embodiment, the spacer comprises, preferably is, independently selected from any one of the formula
- (a) #-Z—NH—$(CH_2)_m$—X-§
- (b) #-Z—NH—$(CH_2)_n$—(O—$CH_2$—$CH_2)_k$—O—$(CH_2)_p$—X-§

(c) #-Z[—NH—(CH$_2$)$_n$—(O—CH$_2$—CH$_2$)$_k$—O—(CH$_2$)$_p$—C(O)—]—NH—(CH$_2$)$_q$—X-§

(d) #-Z[—NH—(CH$_2$)$_n$—(O—CH$_2$—CH$_2$)$_k$—O—(CH$_2$)$_p$—C(O)—]$_r$—NH—(CH$_2$)$_q$—(O—CH$_2$—CH$_2$)$_k$—X-§ wherein —Z— represents independently of each other a bond or —NH—CH(COOH)—(CH$_2$)$_2$—C(O)— or —NH—C[(CH$_2$)$_2$COOH]—C(O)—, X is independently of each other OP(O)(SH) or OP(O)(OH), wherein k is 1, wherein m is 6, wherein n is 2, and wherein p is 1, wherein q is independently of each other an integer of 1 to 6, wherein r is independently of each other an integer of 1 to 3, preferably 1 or 2, wherein said (#) represents the point of covalent linkage to said lipid moiety and said (§) represents the point of covalent linkage to said oligomeric compound.

In another very preferred embodiment, the spacer comprises, preferably is, #-Z—NH—(CH$_2$)$_m$—X-§, wherein —Z— represents a bond, X is independently of each other OP(O)(SH) or OP(O)(OH), wherein m is 6, wherein said (#) represents the point of covalent linkage to said lipid moiety and said (§) represents the point of covalent linkage to said oligomeric compound.

In another very preferred embodiment, the spacer comprises, preferably is, #-Z—NH—(CH$_2$)$_m$—X-§, wherein —Z— represents a bond, X is OP(O)(OH), wherein m is 6, wherein said (#) represents the point of covalent linkage to said lipid moiety and said (§) represents the point of covalent linkage to said oligomeric compound.

In another very preferred embodiment, the spacer comprises, preferably is, #-Z—NH—(CH$_2$)$_m$—X-§, wherein —Z— represents a bond, X is OP(O)(SH), wherein m is 6, wherein said (#) represents the point of covalent linkage to said lipid moiety and said (§) represents the point of covalent linkage to said oligomeric compound.

In another very preferred embodiment, said one or more lipid moiety is covalently linked to said oligomeric compound either directly or via a spacer through a —OP(O)(SH)— or a —OP(O)(OH)— moiety, typically and preferably comprised by said one or more lipid moiety or said spacer, wherein said —OP(O)(SH)— or said —OP(O)(OH)— moiety is linked to the 5'-terminal OH-group or to the 3'-terminal OH-group of said oligomeric compound.

In another very preferred embodiment, said one or more lipid moiety is independently of each other linked to said oligomeric compound at (i) a terminal residue of said oligomeric compound, (ii) the 5' terminus of said oligomeric compound, (iii) the 3' terminus of said oligomeric compound; (iv) an internal residue of said oligomeric compound.

In another preferred embodiment, said one or more lipid moiety, preferably said exactly one lipid moiety, is independently of each other linked to said oligomeric compound at a terminal residue of said oligomeric compound.

In another preferred embodiment, said one or more lipid moiety, preferably said exactly one lipid moiety, is independently of each other linked to said oligomeric compound at the 5' terminus of said oligomeric compound.

In another preferred embodiment, said one or more lipid moiety, preferably said exactly one lipid moiety, is independently of each other linked to said oligomeric compound at the 3' terminus of said oligomeric compound.

In another preferred embodiment, said one or more lipid moiety, preferably said exactly one lipid moiety, is independently of each other linked to said oligomeric compound at an internal residue of said oligomeric compound.

In another very preferred embodiment, said one or more lipid moiety, preferably exactly one lipid moiety, is covalently linked to said oligomeric compound, preferably to said oligonucleotide, either directly or via a spacer through a —OP(O)(SH)— or a —OP(O)(OH)— or a —NHP(O)(OH)— or a —NHP(O)(SH)— or a —NH—C(O)— moiety, typically and preferably comprised by said one or more lipid moiety or said spacer, wherein said —OP(O)(SH)— or said —OP(O)(OH)— or said —NHP(O)(OH)— or said —NHP(O)(SH)— or said —NH—C(O)— moiety is linked to the 5'-terminal OH-group or to the 3'-terminal OH-group of said oligomeric compound.

In another very preferred embodiment, said one or more lipid moiety, preferably exactly one lipid moiety, is covalently linked to said oligomeric compound, preferably to said oligonucleotide, either directly or via a spacer through a —OP(O)(SH)— or a —OP(O)(OH)— moiety, wherein said —OP(O)(SH)— or said —OP(O)(OH)— moiety is linked to the 5'-terminal OH-group or to the 3'-terminal OH-group of said oligomeric compound, and wherein typically and preferably said —OP(O)(SH)— or said —OP(O)(OH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(SH)— moiety, wherein said —OP(O)(SH)— moiety is linked to the 5'-terminal OH-group or to the 3'-terminal OH-group of said oligomeric compound, and wherein typically and preferably said —OP(O)(SH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(SH)— moiety, wherein said —OP(O)(SH)— moiety is linked to the 5'-terminal OH-group of said oligomeric compound, and wherein typically and preferably said —OP(O)(SH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(SH)— moiety, wherein said —OP(O)(SH)— moiety is linked to the 3'-terminal OH-group of said oligomeric compound, and wherein typically and preferably said —OP(O)(SH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(OH)— moiety, wherein said —P(O)(OH)— moiety is linked to the 5'-terminal OH-group or to the 3'-terminal OH-group of said oligomeric compound, and wherein typically and preferably said —OP(O)(OH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(OH)— moiety, wherein said —P(O)(OH)— moiety is linked to the 5'-terminal OH-group of said oligomeric compound, and wherein typically and preferably said —OP(O)(OH)— moiety is comprised by said one or more lipid moiety or said spacer.

In another very preferred embodiment, said one or more lipid moiety, preferably exactly one lipid moiety, is covalently linked to said oligomeric compound, preferably to said oligonucleotide, either directly or via a spacer through a —OP(O)(OH)— moiety, wherein said —P(O)(OH)— moiety is linked to the 3'-terminal OH-group of said oligomeric compound, and wherein typically and preferably said —OP(O)(OH)— moiety is comprised by said one or more lipid moiety or said spacer.

In another preferred embodiment, said composition does not comprise nucleosides other than tc-DNA nucleosides.

In another preferred embodiment, said oligomeric compound does not comprise nucleosides other than tc-DNA nucleosides.

In another preferred embodiment, said composition further comprises one or more nucleosides other than tc-DNA nucleosides.

In another preferred embodiment, said oligomeric compound further comprises one or more nucleosides other than tc-DNA nucleosides.

In another preferred embodiment, said oligomeric compound comprises one or more tc-DNA nucleosides and one or more nucleosides other than tc-DNA nucleosides, wherein 50% or more of all nucleosides are tc-DNA nucleosides.

In another preferred embodiment, said oligomeric compound comprises one or more tc-DNA nucleosides and one or more nucleosides other than tc-DNA nucleosides, wherein 60% or more of all nucleosides are tc-DNA nucleosides.

In another preferred embodiment, said oligomeric compound comprises one or more tc-DNA nucleosides and one or more nucleosides other than tc-DNA nucleosides, wherein 70% or more of all nucleosides are tc-DNA nucleosides.

In another preferred embodiment, said oligomeric compound comprises one or more tc-DNA nucleosides and one or more nucleosides other than tc-DNA nucleosides, wherein 75% or more of all nucleosides are tc-DNA nucleosides.

In another preferred embodiment, said oligomeric compound comprises one or more tc-DNA nucleosides and one or more nucleosides other than tc-DNA nucleosides, wherein 80% or more of all nucleosides are tc-DNA nucleosides.

In another preferred embodiment, said oligomeric compound comprises one or more tc-DNA nucleosides and one or more nucleosides other than tc-DNA nucleosides, wherein 85% or more of all nucleosides are tc-DNA nucleosides.

In another preferred embodiment, said oligomeric compound comprises one or more tc-DNA nucleosides and one or more nucleosides other than tc-DNA nucleosides, wherein 90% or more of all nucleosides are tc-DNA nucleosides.

In another preferred embodiment, said oligomeric compound comprises one or more tc-DNA nucleosides and one or more nucleosides other than tc-DNA nucleosides, wherein 95% or more of all nucleosides are tc-DNA nucleosides.

In another preferred embodiment, said oligomeric compound further comprises one or more nucleosides other than tc-DNA nucleosides, wherein said one or more nucleosides other than tc-DNA nucleosides are independently of each other selected from (i) 2'-modified ribonucleic acid (2'-modified-RNA) nucleosides;
(ii) ribonucleic acid (RNA) nucleosides;
(iii) deoxyribonucleic acid (DNA) nucleosides;
(iv) locked nucleic acid (LNA) nucleosides;
(v) peptide nucleic acids (PNAs) nucleosides;
(vi) 2'-deoxy 2'-fluoro-arabino nucleosides;
(vii) hexitol nucleic acids (HNAs) nucleosides; and
(viii) phosphorodiamidate morpholino (PMO) nucleosides.

In another preferred embodiment, said oligomeric compound further comprises one or more nucleosides other than tc-DNA nucleosides, wherein said one or more nucleosides other than tc-DNA nucleosides are independently of each other 2'-modified ribonucleic acid (2'-modified-RNA) nucleosides.

In another preferred embodiment, said 2'-modified-RNA nucleosides are incorporated in at least two adjacent positions that form self-complementary Watson-Crick base pairs.

In another preferred embodiment, said 2'-modified-RNA nucleosides are incorporated at three or more adjacent positions that form self-complementary Watson-Crick base pairs.

In another preferred embodiment, said oligomeric compound further comprises one or more nucleosides other than tc-DNA nucleosides, wherein said one or more nucleosides other than tc-DNA nucleosides are independently of each other ribonucleic acid (RNA) nucleosides.

In another preferred embodiment, said oligomeric compound further comprises one or more nucleosides other than tc-DNA nucleosides, wherein said one or more nucleosides other than tc-DNA nucleosides are independently of each other deoxyribonucleic acid (DNA) nucleosides.

In another preferred embodiment, said oligomeric compound further comprises one or more nucleosides other than tc-DNA nucleosides, wherein said one or more nucleosides other than tc-DNA nucleosides are independently of each other locked nucleic acid (LNA) nucleosides.

In another preferred embodiment, said oligomeric compound further comprises one or more nucleosides other than tc-DNA nucleosides, wherein said one or more nucleosides other than tc-DNA nucleosides are independently of each other peptide nucleic acids (PNAs) nucleosides.

In another preferred embodiment, said oligomeric compound further comprises one or more nucleosides other than tc-DNA nucleosides, wherein said one or more nucleosides other than tc-DNA nucleosides are independently of each other 2'-deoxy 2'-fluoro-arabino nucleosides.

In another preferred embodiment, said oligomeric compound further comprises one or more nucleosides other than tc-DNA nucleosides, wherein said one or more nucleosides other than tc-DNA nucleosides are independently of each other hexitol nucleic acids (HNAs) nucleosides.

In another preferred embodiment, said oligomeric compound further comprises one or more nucleosides other than tc-DNA nucleosides, wherein said one or more nucleosides other than tc-DNA nucleosides are independently of each other phosphorodiamidate morpholino (PMO) nucleosides.

In another preferred embodiment, said oligomeric compound further comprises one or more nucleosides other than tc-DNA nucleosides, wherein said one or more nucleosides other than tc-DNA nucleosides are independently of each other selected from
(i) RNA nucleosides;
(ii) 2'-O-methyl-RNA nucleosides;
(iii) 2'-O-propargyl-RNA nucleosides;
(iv) 2'-O-propylamino-RNA nucleosides;
(v) 2'-O-amino-RNA nucleosides;

(vi) 2'-fluoro-RNA nucleosides;
(vii) 2'-O-methoxyethyl-RNA nucleosides;
(viii) morpholino nucleosides; and
(ix) locked nucleic acid nucleosides.

In another preferred embodiment, said oligomeric compound further comprises one or more nucleosides other than tc-DNA nucleosides, wherein said one or more nucleosides other than tc-DNA nucleosides are independently of each other RNA nucleosides.

In another preferred embodiment, said oligomeric compound further comprises one or more nucleosides other than tc-DNA nucleosides, wherein said one or more nucleosides other than tc-DNA nucleosides are independently of each other 2'-O-methyl-RNA nucleosides.

In another preferred embodiment, said oligomeric compound further comprises one or more nucleosides other than tc-DNA nucleosides, wherein said one or more nucleosides other than tc-DNA nucleosides are independently of each other 2'-O-propargyl-RNA nucleosides.

In another preferred embodiment, said oligomeric compound further comprises one or more nucleosides other than tc-DNA nucleosides, wherein said one or more nucleosides other than tc-DNA nucleosides are independently of each other 2'-O-propylamino-RNA nucleosides.

In another preferred embodiment, said oligomeric compound further comprises one or more nucleosides other than tc-DNA nucleosides, wherein said one or more nucleosides other than tc-DNA nucleosides are independently of each other 2'-O-amino-RNA nucleosides.

In another preferred embodiment, said oligomeric compound further comprises one or more nucleosides other than tc-DNA nucleosides, wherein said one or more nucleosides other than tc-DNA nucleosides are independently of each other 2'-fluoro-RNA nucleosides.

In another preferred embodiment, said oligomeric compound further comprises one or more nucleosides other than tc-DNA nucleosides, wherein said one or more nucleosides other than tc-DNA nucleosides are independently of each other 2'-O-methoxyethyl-RNA nucleosides.

In another preferred embodiment, said oligomeric compound further comprises one or more nucleosides other than tc-DNA nucleosides, wherein said one or more nucleosides other than tc-DNA nucleosides are independently of each other morpholino nucleosides.

In another preferred embodiment, said oligomeric compound further comprises one or more nucleosides other than tc-DNA nucleosides, wherein said one or more nucleosides other than tc-DNA nucleosides are independently of each other locked nucleic acid RNA nucleosides.

In another preferred embodiment, said oligomeric compound is complementary to a target sequence.

In another preferred embodiment, said oligomeric compound has a length of, up to 40 monomer subunits, preferably up to 30 monomer subunits, more preferably up to 30 monomer subunits, again more preferably up to 20 monomer subunits or up to 15 monomer subunits. In a further embodiment, said oligomer comprises from 5 to 40 monomeric subunits, preferably from 8 to 30 monomer subunits, more preferably from 8 to 25 monomer subunits, again more preferably from 8 to 20 monomer subunits.

In another preferred embodiment, said oligomeric compound comprises from 5 to 40 nucleotides, and wherein preferably said oligomeric compound comprises 10 to 30 nucleotides, and wherein further preferably said oligomeric compound comprises from 10 to 25 nucleotides.

In another preferred embodiment, said oligomeric compound is an oligonucleotide, said wherein said oligomeric compound comprises one or more tricyclo-deoxyribonucleic acid (tc-DNA) nucleosides, wherein preferably said oligomeric compound comprises from 5 to 40 monomer subunits.

In another preferred embodiment, said oligomeric compound is an oligonucleotide, said wherein said oligomeric compound comprises one or more tricyclo-deoxyribonucleic acid (tc-DNA) nucleosides, wherein said oligomeric compound comprises from 5 to 40 monomer subunits, and wherein said monomer subunits are linked by internucleosidic linkage groups, In another preferred embodiment, said monomer subunits are independently of each other selected from naturally occurring nucleosides, modified nucleosides and mimetics of nucleosides, wherein preferably said naturally occurring nucleosides, said modified nucleosides and said mimetics of nucleosides are independently of each other selected from tricyclic nucleosides, ribonucleic acid (RNA) nucleosides, deoxyribonucleic acid (DNA) nucleosides, 2'-modified ribonucleic acid (2'-modified-RNA) nucleosides, locked nucleic acid (LNA) nucleosides, peptide nucleic acids (PNAs) nucleosides, 2'-deoxy 2'-fluoro-arabino nucleosides, hexitol nucleic acids (HNAs) nucleosides and phosphorodiamidate morpholino (PMO) nucleosides.

In another preferred embodiment, said monomer subunits are independently of each other selected from naturally occurring nucleosides, modified nucleosides and mimetics of nucleosides, wherein preferably said naturally occurring nucleosides, said modified nucleosides and said mimetics of nucleosides are independently of each other selected from tricyclic nucleosides, ribonucleic acid (RNA) nucleosides, deoxyribonucleic acid (DNA) nucleosides, 2'-modified ribonucleic acid (2'-modified-RNA) nucleosides, locked nucleic acid (LNA) nucleosides, peptide nucleic acids (PNAs) nucleosides, 2'-deoxy 2'-fluoro-arabino nucleosides, hexitol nucleic acids (HNAs) nucleosides and phosphorodiamidate morpholino (PMO) nucleosides, and wherein said monomer subunits are linked by a plurality of internucleosidic linkage groups.

In another preferred embodiment, said oligomeric compound comprises from 5 to 40 monomer subunits, wherein said monomer subunits are nucleosides, and wherein one or more of said nucleosides are said one or more tricyclo-deoxyribonucleic acid (tc-DNA) nucleosides, and wherein said monomer subunits are linked by a plurality of internucleosidic linkage groups, and wherein preferably said oligomeric compound is an oligonucleotide.

In another preferred embodiment, said oligomeric compound comprises from 5 to 40 monomer subunits, wherein said monomer subunits are nucleosides, and wherein one or more of said nucleosides are said one or more tricyclo-deoxyribonucleic acid (tc-DNA) nucleosides, and wherein said monomer subunits are linked by a plurality of internucleosidic linkage groups, and wherein preferably said oligomeric compound is an oligonucleotide.

In another preferred embodiment, said oligomeric compound comprises from 5 to 40 monomer subunits, wherein said monomer subunits are nucleosides, and wherein one or more of said nucleosides are said one or more tricyclo-deoxyribonucleic acid (tc-DNA) nucleosides, and wherein said nucleosides are linked by a plurality of internucleosidic linkage groups, and wherein preferably said oligomeric compound is an oligonucleotide.

In another preferred embodiment, said composition does not comprise nucleosides other than tc-DNA nucleosides. In another preferred embodiment, said oligomeric compound does not comprise nucleosides other than tc-DNA nucleosides. In another preferred embodiment, said composition further comprises one or more nucleosides other than tc-DNA nucleosides. In another preferred embodiment, said oligomeric compound further comprises one or more nucleosides other than tc-DNA nucleosides.

In another preferred embodiment, said oligomeric compound comprise one or more tc-DNA nucleosides. In another preferred embodiment, said oligomeric compound comprise one or more tc-DNA nucleosides and one or more nucleosides other than tc-DNA nucleosides.

In another preferred embodiment, said one or more tc-DNA nucleosides, or said one or more tc-DNA nucleosides and said one or more nucleosides other than tc-DNA nucleosides are linked by a plurality of internucleosidic linkage groups.

In another preferred embodiment, said oligomeric compound comprises from 5 to 40 monomer subunits, wherein said monomer subunits are nucleosides, and wherein all of said nucleosides are said one or more tricyclo-deoxyribonucleic acid (tc-DNA) nucleosides, and wherein said nucleosides are linked by a plurality of internucleosidic linkage groups, and wherein preferably said oligomeric compound is an oligonucleotide.

In another preferred embodiment, said oligomeric compound comprises from 5 to 40 monomer subunits, wherein said monomer subunits are nucleosides, and wherein one of said nucleosides is a nucleosides other than tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein preferably said oligomeric compound is an oligonucleotide.

In another preferred embodiment, said oligomeric compound comprises from 5 to 40 monomer subunits, wherein said monomer subunits are nucleosides, and wherein at most 5, preferably at most 4, further preferably at most 3 of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 5, preferably at most 4, further preferably at most 3 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide.

In another very preferred embodiment, said oligomeric compound comprises from 5 to 40 monomer subunits, wherein said monomer subunits are nucleosides, and wherein at most 3 of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 3 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide.

In another very preferred embodiment, said oligomeric compound comprises from 5 to 40 monomer subunits, wherein said monomer subunits are nucleosides, and wherein at most 2 of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 2 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide.

In another very preferred embodiment, said oligomeric compound comprises from 5 to 40 monomer subunits, wherein said monomer subunits are nucleosides, and wherein at most 1, of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 1 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide.

In another preferred embodiment, said oligomeric compound comprises from 5 to 40 monomer subunits, wherein said monomer subunits are nucleosides, and wherein one of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide.

In another preferred embodiment, said oligomeric compound comprises from 5 to 40 monomer subunits, wherein said monomer subunits are nucleosides, and wherein one of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside and a phosphorodiamidate morpholino (PMO) nucleoside, and wherein preferably said oligomeric compound is an oligonucleotide.

In another preferred embodiment, said oligomeric compound comprises from 5 to 40 monomer subunits, wherein said monomer subunits are nucleosides, and wherein one of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said nucleoside other than a tc-DNA nucleoside is selected from a ribonucleic acid (RNA) nucleoside, a deoxyribonucleic acid (DNA) nucleoside and a 2'-modified ribonucleic acid (2'-modified-RNA) nucleoside, and wherein preferably said oligomeric compound is an oligonucleotide.

In another preferred embodiment, said oligomeric compound comprises from 5 to 40 monomer subunits, wherein said monomer subunits are nucleosides, and wherein two of said nucleosides are nucleosides other than tc-DNA nucleosides, and wherein all the other of said nucleosides are said one or more tricyclo-deoxyribonucleic acid (tc-DNA) nucleosides, and wherein said nucleosides are linked by a plurality of a plurality of internucleosidic linkage groups, and wherein said two nucleosides other than a tc-DNA nucleoside are independently selected from ribonucleic acid (RNA) nucleosides, deoxyribonucleic acid (DNA) nucleosides, 2'-modified ribonucleic acid (2'-modified-RNA) nucleosides, locked nucleic acid (LNA) nucleosides, peptide nucleic acid (PNA) nucleosides, 2'-deoxy 2'-fluoro-arabino nucleosides, hexitol nucleic acid (HNA) nucleosides and phosphorodiamidate morpholino (PMO) nucleosides, and wherein preferably said oligomeric compound is an oligonucleotide.

In another preferred embodiment, said plurality of internucleosidic linkage groups are independently selected from a phosphorothioate linkage group, a phosphorodithioate linkage group, and a phosphorodiester linkage group, a phosphotriester linkage group, an aminoalkylphosphotriester linkage group, a methyl phosphonate linkage group, an alkyl phosphonate linkage group, a 5'-alkylene phosphonate linkage group, a phosphonate linkage group, a phosphinate linkage group, a phosphoramidate linkage group, an 3'-aminophosphoramidate linkage group, an aminoalkyl phosphoramidate linkage group, a thionophosphoramidate linkage group, a thionoalkylphosphonate linkage group, a thionoalkylphosphotriester linkage group, a selenophosphate linkage group, or a boranophosphate linkage group.

In another preferred embodiment, said plurality of internucleosidic linkage groups are independently selected from a phosphorothioate linkage group and a phosphorodiester linkage group.

In another preferred embodiment, no more than 50% of said plurality of internucleosidic linkage groups are phosphorothioate linkage groups. In another preferred embodiment, no more than 45% of said plurality of internucleosidic linkage groups are phosphorothioate linkage groups. In another preferred embodiment, no more than 40% of said plurality of internucleosidic linkage groups are phosphorothioate linkage groups. In another preferred embodiment, no more than 35% of said plurality of internucleosidic linkage groups are phosphorothioate linkage groups. In another preferred embodiment, no more than 33% of said plurality of internucleosidic linkage groups are phosphorothioate linkage groups. In another preferred embodiment, no more than 30% of said plurality of internucleosidic linkage groups are phosphorothioate linkage groups. In another preferred embodiment, no more than 25% of said plurality of internucleosidic linkage groups are phosphorothioate linkage groups. In another preferred embodiment, no more than 20% of said plurality of internucleosidic linkage groups are phosphorothioate linkage groups. In another preferred embodiment, no more than 20% of said plurality of internucleosidic linkage groups are phosphorothioate linkage groups. In another preferred embodiment, no more than 15% of said plurality of internucleosidic linkage groups are phosphorothioate linkage groups. In another preferred embodiment, no more than 10% of said plurality of internucleosidic linkage groups are phosphorothioate linkage groups. In another preferred embodiment, no more than 5% of said plurality of internucleosidic linkage groups are phosphorothioate linkage groups. In another preferred embodiment, none (0%) of said plurality of internucleosidic linkage groups are phosphorothioate linkage groups.

In another preferred embodiment, no more than 8 of said plurality of internucleosidic linkage groups are phosphorothioate linkage groups. In another preferred embodiment, no more than 7 of said plurality of internucleosidic linkage groups are phosphorothioate linkage groups. In another preferred embodiment, no more than 6 of said plurality of internucleosidic linkage groups are phosphorothioate linkage groups. In another preferred embodiment, no more than 5 of said plurality of internucleosidic linkage groups are phosphorothioate linkage groups. In another preferred embodiment, no more than 4 of said plurality of internucleosidic linkage groups are phosphorothioate linkage groups. In another preferred embodiment, no more than 3 of said plurality of internucleosidic linkage groups are phosphorothioate linkage groups. In another preferred embodiment, no more than 2 of said plurality of internucleosidic linkage groups are phosphorothioate linkage groups. In another preferred embodiment, no more than 1 of said plurality of internucleosidic linkage groups are phosphorothioate linkage groups. In another preferred embodiment, none (zero/0) of said plurality of internucleosidic linkage groups are phosphorothioate linkage groups.

In another preferred embodiment, said plurality of internucleosidic linkage groups are independently selected from a phosphorothioate linkage group and a phosphorodiester linkage group, and wherein no more than 30% of said plurality of internucleosidic linkage groups are phosphorothioate linkage groups.

In another preferred embodiment, at least 50% of said plurality of internucleosidic linkage groups are phosphorodiester linkage groups. In another preferred embodiment, at least 55% of said plurality of internucleosidic linkage groups are phosphorodiester linkage groups. In another preferred embodiment, at least 60% of said plurality of internucleosidic linkage groups are phosphorodiester linkage groups. In another preferred embodiment, at least 65% of said plurality of internucleosidic linkage groups are phosphorodiester linkage groups. In another preferred embodiment, at least 66% of said plurality of internucleosidic linkage groups are phosphorodiester linkage groups. In another preferred embodiment, at least 70% of said plurality of internucleosidic linkage groups are phosphorodiester linkage groups. In another preferred embodiment, at least 75% of said plurality of internucleosidic linkage groups are phosphorodiester linkage groups. In another preferred embodiment, at least 80% of said plurality of internucleosidic linkage groups are phosphorodiester linkage groups. In another preferred embodiment, at least 85% of said plurality of internucleosidic linkage groups are phosphorodiester linkage groups. In another preferred embodiment, at least 90% of said plurality of internucleosidic linkage groups are phosphorodiester linkage groups. In another preferred embodiment, at least 95% of said plurality of internucleosidic linkage groups are phosphorodiester linkage groups. In another preferred embodiment, all (100%) of said plurality of internucleosidic linkage groups are phosphorodiester linkage groups.

In another preferred embodiment, at least 80% of said plurality of internucleosidic linkage groups are phosphorodiester linkage groups, and wherein preferably said plurality of internucleosidic linkage groups are independently selected from a phosphorothioate linkage group and a phosphorodiester linkage group.

In another very preferred embodiment, said plurality of internucleosidic linkage groups are independently selected from a phosphorothioate linkage group and a phosphorodiester linkage group, and wherein no more than 6 of said plurality of internucleosidic linkage groups are phosphorothioate linkage groups. In another very preferred embodiment, said plurality of internucleosidic linkage groups are independently selected from a phosphorothioate linkage group and a phosphorodiester linkage group, and wherein no more than 5 of said plurality of internucleosidic linkage groups are phosphorothioate linkage groups. In another very preferred embodiment, said plurality of internucleosidic linkage groups are independently selected from a phosphorothioate linkage group and a phosphorodiester linkage group, and wherein no more than 4 of said plurality of internucleosidic linkage groups are phosphorothioate linkage groups. In another very preferred embodiment, said plurality of internucleosidic linkage groups are independently selected from a phosphorothioate linkage group and a phosphorodiester linkage group, and wherein no more than 3 of said plurality of internucleosidic linkage groups are phosphorothioate linkage groups. In another very preferred embodiment, said plurality of internucleosidic linkage groups are independently selected from a phosphorothioate linkage group and a phosphorodiester linkage group, and wherein no more than 2 of said plurality of internucleosidic linkage groups are phosphorothioate linkage groups. In another very preferred embodiment, said plurality of internucleosidic linkage groups are independently selected from a phosphorothioate linkage group and a phosphorodiester linkage group, and wherein no more than 1 of said plurality of internucleosidic linkage groups are phosphorothioate linkage groups.

In another very preferred embodiment, said plurality of internucleosidic linkage groups are independently selected from a phosphorodiester linkage group. Thus, in another very preferred embodiment, all of said plurality of internucleosidic linkage groups are phosphorodiester linkage groups.

In another very preferred embodiment, said oligomeric compound comprises from 5 to 40 monomer subunits, wherein said monomer subunits are nucleosides, and wherein at most 3 of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 3 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide, and wherein said plurality of internucleosidic linkage groups are independently selected from a phosphorothioate linkage group and a phosphorodiester linkage group, and wherein no more than 6, preferably no more than 5, further preferably no more than 4, again further preferably no more than 3, further preferably no more than 2, further preferably no more than 1, of said plurality of internucleosidic linkage groups are phosphorothioate linkage groups. In a very preferred embodiment hereof, all of said plurality of internucleosidic linkage groups are independently selected from a phosphorodiester linkage group.

In another very preferred embodiment, said oligomeric compound comprises from 5 to 40 monomer subunits, wherein said monomer subunits are nucleosides, and wherein at most 2 of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 2 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide, and wherein said plurality of internucleosidic linkage groups are independently selected from a phosphorothioate linkage group and a phosphorodiester linkage group, and wherein no more than 6, preferably no more than 5, further preferably no more than 4, again further preferably no more than 3, further preferably no more than 2, further preferably no more than 1, of said plurality of internucleosidic linkage groups are phosphorothioate linkage groups. In a very preferred embodiment hereof, all of said plurality of internucleosidic linkage groups are independently selected from a phosphorodiester linkage group.

In another very preferred embodiment, said oligomeric compound comprises from 5 to 40 monomer subunits, wherein said monomer subunits are nucleosides, and wherein at most 1, of said nucleosides is a nucleoside other than a tc-DNA nucleoside, and wherein all the other of said nucleosides are said one or more tricyclo-deoxyribonucleic acid (tc-DNA) nucleosides, and wherein said nucleosides are linked by a plurality of internucleosidic linkage groups, and wherein said at most 1 nucleoside other than a tc-DNA nucleoside is selected from a ribonucleic acid (RNA) nucleoside, a deoxyribonucleic acid (DNA) nucleoside, a 2'-modified ribonucleic acid (2'-modified-RNA) nucleoside, a locked nucleic acid (LNA) nucleoside, a peptide nucleic acid (PNA) nucleoside, a 2'-deoxy 2'-fluoro-arabino nucleoside, hexitol nucleic acid (HNA) nucleoside and a phosphorodiamidate morpholino (PMO) nucleoside, and wherein preferably said oligomeric compound is an oligonucleotide, and wherein said plurality of internucleosidic linkage groups are independently selected from a phosphorothioate linkage group and a phosphorodiester linkage group, and wherein no more than 6, preferably no more than 5, further preferably no more than 4, again further preferably no more than 3, further preferably no more than 2, further preferably no more than 1, of said plurality of internucleosidic linkage groups are phosphorothioate linkage groups. In a very preferred embodiment hereof, all of said plurality of internucleosidic linkage groups are independently selected from a phosphorodiester linkage group.

In another preferred embodiment, said oligomeric compound does not contain a direct tc-DNA to tc-DNA phosphorothioate internucleosidic linkage.

The following tables provides for very preferred embodiments of the present invention.

TABLE 1

Preferred embodiments of the oligomeric compound of the present invention, wherein all oligonucleotides may use phosphorothioate linkages, phosphorodiester linkages, or other internucleoside linkages, or mixtures thereof, and any suitable base analog may be employed in addition to the nucleobase shown.

| Identifier | Sequence of oligomeric compound (A, G, C, T = tc-DNA; a, g, c, u = 2'-modified-RNA; a', g', c', t' = DNA) |
|---|---|
| SEQ ID NO: 1 | CCTCGGCTTACCT |
| SEQ ID NO: 2 | ACCTCGGCTTACC |
| SEQ ID NO: 3 | CCuCGGCTTACCT |
| SEQ ID NO: 4 | AAGAuGGCATTTCTA |
| SEQ ID NO: 5 | CATCCTGgAGTTCCT |
| SEQ ID NO: 6 | GCCATCCTGgAGTTC |
| SEQ ID NO: 7 | CCGCTGCCCAATGCC |
| SEQ ID NO: 8 | ACTTcATCCCACTGA |
| SEQ ID NO: 9 | ATTTCATTCAACTGT |
| SEQ ID NO: 10 | CTGGAGTTCCTGTAA |
| SEQ ID NO: 11 | CTGgAGTTCCTGTAA |
| SEQ ID NO: 12 | TCCTGgAGTTCCTGT |
| SEQ ID NO: 13 | GTGTTCTTGTaCTTC |
| SEQ ID NO: 14 | CTGAaGGTGTTCTTG |
| SEQ ID NO: 15 | CTCCGGTTcTGAAGG |
| SEQ ID NO: 16 | TTGAATCCTuTAACA |
| SEQ ID NO: 17 | CTTTCaTAATGCTGG |
| SEQ ID NO: 18 | CTTTCATAAuGCTGG |
| SEQ ID NO: 19 | AAGATGGCATTTCTA |
| SEQ ID NO: 20 | CAGCAgCAGCAGCAG |
| SEQ ID NO: 21 | GCCTGGACAGCTCCT |
| SEQ ID NO: 22 | AAGAt'GGCATTTCTA | wherein an * between two nucleosides indicates a phosphorothioate internucleoside linkage group, the absence of an * between two nucleosides indicates a phosphorodiester internucleoside linkage group, the capitalized letters A, C, G, and T indicate tc-DNA nucleosides; the lowercase letters a, c, u, g, and t indicate 2'-modified-RNA, preferably 2'-O-methyl-RNA, nucleosides, the nucleobase at all C positions is 5-methylcytosine, the nucleobase at all c positions is cytosine, and the primed lowercase letters a', u', g', and t' indicate deoxyribonucleosides.

In a preferred embodiment, said oligomeric compound is selected from the oligomeric compounds listed in Table 1, wherein typically and preferably said 2'-modified-RNA is 2'-OMe-RNA.

In a preferred embodiment, said oligomeric compound, preferably said oligonucleotide, is selected from any one of the sequences of SEQ ID NOs:1-22, wherein said 2'-modified-RNA is 2'-OMe-RNA. In a preferred embodiment, said oligomeric compound, preferably said oligonucleotide, is selected from any one of the sequences of SEQ ID NOs:1-22, wherein said 2'-modified-RNA is 2'-OMe-RNA, and wherein each of said internucleosidic linkage groups of the sequences of SEQ ID NOs:1-22 are phosphorodiester linkage groups.

In a further preferred embodiment, said oligomeric compound comprises, preferably is, the sequence of SEQ ID NO: 1.

In a further preferred embodiment, said oligomeric compound comprises, preferably is, the sequence of SEQ ID NO:2.

In a further preferred embodiment, said oligomeric compound comprises, preferably is, the sequence of SEQ ID NO:3. In a further preferred embodiment, said oligomeric compound comprises, preferably is, the sequence of SEQ ID NO:3, wherein said 2'-modified-RNA is 2'-OMe-RNA.

In a further preferred embodiment, said oligomeric compound comprises, preferably is, the sequence of SEQ ID NO:4. In a further preferred embodiment, said oligomeric compound comprises, preferably is, the sequence of SEQ ID NO:4, wherein said 2'-modified-RNA is 2'-OMe-RNA.

In a further preferred embodiment, said oligomeric compound comprises, preferably is, the sequence of SEQ ID NO:5. In a further preferred embodiment, said oligomeric compound comprises, preferably is, the sequence of SEQ ID NO:5, wherein said 2'-modified-RNA is 2'-OMe-RNA.

In a further preferred embodiment, said oligomeric compound comprises, preferably is, the sequence of SEQ ID NO:6. In a further preferred embodiment, said oligomeric compound comprises, preferably is, the sequence of SEQ ID NO:6, wherein said 2'-modified-RNA is 2'-OMe-RNA.

In a further preferred embodiment, said oligomeric compound comprises, preferably is, the sequence of SEQ ID NO:7.

In a further preferred embodiment, said oligomeric compound comprises, preferably is, the sequence of SEQ ID NO:8. In a further preferred embodiment, said oligomeric compound comprises, preferably is, the sequence of SEQ ID NO:8, wherein said 2'-modified-RNA is 2'-OMe-RNA.

In a further preferred embodiment, said oligomeric compound comprises, preferably is, the sequence of SEQ ID NO:9.

In a further preferred embodiment, said oligomeric compound comprises, preferably is, the sequence of SEQ ID NO: 10.

In a further preferred embodiment, said oligomeric compound comprises, preferably is, the sequence of SEQ ID NO:11. In a further preferred embodiment, said oligomeric compound comprises, preferably is, the sequence of SEQ ID NO:11, wherein said 2'-modified-RNA is 2'-OMe-RNA.

In a further preferred embodiment, said oligomeric compound comprises, preferably is, the sequence of SEQ ID NO:12. In a further preferred embodiment, said oligomeric compound comprises, preferably is, the sequence of SEQ ID NO:12, wherein said 2'-modified-RNA is 2'-OMe-RNA.

In a further preferred embodiment, said oligomeric compound comprises, preferably is, the sequence of SEQ ID NO:13. In a further preferred embodiment, said oligomeric compound comprises, preferably is, the sequence of SEQ ID NO:13, wherein said 2'-modified-RNA is 2'-OMe-RNA.

In a further preferred embodiment, said oligomeric compound comprises, preferably is, the sequence of SEQ ID NO:14. In a further preferred embodiment, said oligomeric compound comprises, preferably is, the sequence of SEQ ID NO:14, wherein said 2'-modified-RNA is 2'-OMe-RNA.

In a further preferred embodiment, said oligomeric compound comprises, preferably is, the sequence of SEQ ID NO:15. In a further preferred embodiment, said oligomeric compound comprises, preferably is, the sequence of SEQ ID NO:15, wherein said 2'-modified-RNA is 2'-OMe-RNA.

In a further preferred embodiment, said oligomeric compound comprises, preferably is, the sequence of SEQ ID NO:16. In a further preferred embodiment, said oligomeric compound comprises, preferably is, the sequence of SEQ ID NO:16, wherein said 2'-modified-RNA is 2'-OMe-RNA.

In a further preferred embodiment, said oligomeric compound comprises, preferably is, the sequence of SEQ ID NO:17. In a further preferred embodiment, said oligomeric compound comprises, preferably is, the sequence of SEQ ID NO:17, wherein said 2'-modified-RNA is 2'-OMe-RNA.

In a further preferred embodiment, said oligomeric compound comprises, preferably is, the sequence of SEQ ID NO:18. In a further preferred embodiment, said oligomeric compound comprises, preferably is, the sequence of SEQ ID NO:18, wherein said 2'-modified-RNA is 2'-OMe-RNA.

In a further preferred embodiment, said oligomeric compound comprises, preferably is, the sequence of SEQ ID NO: 19.

In a further preferred embodiment, said oligomeric compound comprises, preferably is, the sequence of SEQ ID NO:20. In a further preferred embodiment, said oligomeric compound comprises, preferably is, the sequence of SEQ ID NO:20, wherein said 2'-modified-RNA is 2'-OMe-RNA.

In a further preferred embodiment, said oligomeric compound comprises, preferably is, the sequence of SEQ ID NO:21.

In a further preferred embodiment, said oligomeric compound comprises, preferably is, the sequence of SEQ ID NO:22.

In a further preferred embodiment, said oligomeric compound is selected from the oligomeric compounds listed in Table 2, wherein typically and preferably said 2'-modified-RNA is 2'-OMe-RNA.

In a very preferred embodiment, said oligomeric compound, preferably said oligonucleotide, is selected from any one of the sequences of SEQ ID NOs:1-37.

In a further very preferred embodiment, said oligomeric compound, preferably said oligonucleotide, is selected from any one of the sequences of SEQ ID NOs:1-37, wherein said 2'-modified-RNA is 2'-OMe-RNA.

TABLE 2

Very preferred embodiments of oligonucleotide sequences of the oligomeric compound of the present invention. PO refers to phosphorodiester internucleosidic linkages and PS refers to phosphorothioate internucleosidic linkages (indicated by * in the table). A, G, C, and T refer to tc-DNA; a, g, c, and u refer to 2'-O-Me-RNA; and a', g', c' and t' refers to DNA. All tc-DNA cytosine positions ("C") use the 5-methylcytosine base analog, and all 2'-O-Me RNA positions ("c") use cytosine.

| Identifier | Sequence of oligomeric compound (A, G, C, T = tc-DNA; a, g, c, u = 2'-modified-RNA; a', g', c' t' = DNA) | Internucleosidic linkages |
|---|---|---|
| SEQ ID NO: 1 | CCTCGGCTTACCT | Full PO |
| SEQ ID NO: 2 | ACCTCGGCTTACC | Full PO |
| SEQ ID NO: 3 | CCuCGGCTTACCT | Full PO |
| SEQ ID NO: 4 | AAGAuGGCATTTCTA | Full PO |
| SEQ ID NO: 5 | CATCCTGgAGTTCCT | Full PO |
| SEQ ID NO: 6 | GCCATCCTGgAGTTC | Full PO |
| SEQ ID NO: 7 | CCGCTGCCCAATGCC | Full PO |
| SEQ ID NO: 8 | ACTTcATCCCACTGA | Full PO |
| SEQ ID NO: 9 | ATTTCATTCAACTGT | Full PO |
| SEQ ID NO: 10 | CTGGAGTTCCTGTAA | Full PO |
| SEQ ID NO: 11 | CTGgAGTTCCTGTAA | Full PO |
| SEQ ID NO: 12 | TCCTGgAGTTCCTGT | Full PO |
| SEQ ID NO: 13 | GTGTTCTTGTaCTTC | Full PO |
| SEQ ID NO: 14 | CTGAaGGTGTTCTTG | Full PO |
| SEQ ID NO: 15 | CTCCGGTTcTGAAGG | Full PO |
| SEQ ID NO: 16 | TTGAATCCTuTAACA | Full PO |
| SEQ ID NO: 17 | CTTTCaTAATGCTGG | Full PO |

TABLE 2-continued

Very preferred embodiments of oligonucleotide sequences of the oligomeric compound of the present invention. PO refers to phosphorodiester internucleosidic linkages and PS refers to phosphorothioate internucleosidic linkages (indicated by * in the table). A, G, C, and T refer to tc-DNA; a, g, c, and u refer to 2'-O-Me-RNA; and a', g', c' and t' refers to DNA. All tc-DNA cytosine positions ("C") use the 5-methylcytosine base analog, and all 2'-O-Me RNA positions ("c") use cytosine.

| Identifier | Sequence of oligomeric compound (A, G, C, T = tc-DNA; a, g, c, u = 2'-modified-RNA; a', g', c' t' = DNA) | Internucleosidic linkages |
|---|---|---|
| SEQ ID NO: 18 | CTTTCATAAuGCTGG | Full PO |
| SEQ ID NO: 19 | AAGATGGCATTTCTA | Full PO |
| SEQ ID NO: 20 | CAGCAgCAGCAGCAGCAG | Full PO |
| SEQ ID NO: 21 | GCCTGGACAGCTCCT | Full PO |
| SEQ ID NO: 22 | AAGAt'GGCATTTCTA | Full PO |
| SEQ ID NO: 23 | C*C*T*C*G*G*C*T*T*A*C*C*T | Full PS |
| SEQ ID NO: 24 | A*AGAuGGCATTTCTA | PO, but with PS at * |
| SEQ ID NO: 25 | A*A*GAuGGCATTTCTA | PO, but with PS at * |
| SEQ ID NO: 26 | A*A*G*AuGGCATTTCTA | PO, but with PS at * |
| SEQ ID NO: 27 | A*A*G*A*uGGCATTTCTA | PO, but with PS at * |
| SEQ ID NO: 28 | A*A*G*A*u*GGCATTTCTA | PO, but with PS at * |
| SEQ ID NO: 29 | A*A*G*A*u*G*GCATTTCTA | PO, but with PS at * |
| SEQ ID NO: 30 | A*A*G*A*u*G*G*CATTTCTA | PO, but with PS at * |
| SEQ ID NO: 31 | A*AGATGGCATTTCTA | PO, but with PS at * |
| SEQ ID NO: 32 | A*A*GATGGCATTTCTA | PO, but with PS at * |
| SEQ ID NO: 33 | A*A*G*ATGGCATTTCTA | PO, but with PS at * |
| SEQ ID NO: 34 | A*A*G*A*TGGCATTTCTA | PO, but with PS at * |
| SEQ ID NO: 35 | A*A*G*A*T*GGCATTTCTA | PO, but with PS at * |
| SEQ ID NO: 36 | A*A*G*A*T*G*GCATTTCTA | PO, but with PS at * |
| SEQ ID NO: 37 | A*A*G*A*T*G*G*CATTTCTA | PO, but with PS at * | wherein an * between two nucleosides indicates a phosphorothioate internucleoside linkage group, the absence of an * between two nucleosides indicates a phosphorodiester internucleoside linkage group, the capitalized letters A, C, G, and T indicate tc-DNA nucleosides; the lowercase letters a, c, u, g, and t indicate 2'-modified-RNA, preferably 2'-O-methyl-RNA nucleosides, the nucleobase at all C positions is 5-methylcytosine, the nucleobase at all c positions is cytosine, and the primed lowercase letters a', u', g', and t' indicate deoxyribonucleosides.

In a further very preferred embodiment, said oligomeric compound is a sequence selected from any one of SEQ ID NOs:1-37, wherein each of said internucleosidic linkage groups of the sequences of SEQ ID NOs:1-22 are phosphorodiester linkage groups, and wherein preferably said 2'-modified-RNA is 2'-OMe-RNA. In a further very preferred embodiment, said oligomeric compound is a sequence selected from any one of SEQ ID NOs:1-37, wherein each of said internucleosidic linkage groups of the sequences of SEQ ID NOs:1-22 are phosphorodiester linkage groups, and wherein said 2'-modified-RNA is 2'-OMe-RNA.

In a further preferred embodiment, said oligomeric compound comprises, preferably is, the sequence of SEQ ID NO:23.

In a further preferred embodiment, said oligomeric compound comprises, preferably is, the sequence of SEQ ID NO:24. In a further preferred embodiment, said oligomeric compound comprises, preferably is, the sequence of SEQ ID NO:24, wherein said 2'-modified-RNA is 2'-OMe-RNA.

In a further preferred embodiment, said oligomeric compound comprises, preferably is, the sequence of SEQ ID NO:25. In a further preferred embodiment, said oligomeric compound comprises, preferably is, the sequence of SEQ ID NO:25, wherein said 2'-modified-RNA is 2'-OMe-RNA.

In a further preferred embodiment, said oligomeric compound comprises, preferably is, the sequence of SEQ ID NO:26. In a further preferred embodiment, said oligomeric compound comprises, preferably is, the sequence of SEQ ID NO:26, wherein said 2'-modified-RNA is 2'-OMe-RNA.

In a further preferred embodiment, said oligomeric compound comprises, preferably is, the sequence of SEQ ID NO:27. In a further preferred embodiment, said oligomeric compound comprises, preferably is, the sequence of SEQ ID NO:27, wherein said 2'-modified-RNA is 2'-OMe-RNA.

In a further preferred embodiment, said oligomeric compound comprises, preferably is, the sequence of SEQ ID NO:28. In a further preferred embodiment, said oligomeric compound comprises, preferably is, the sequence of SEQ ID NO:28, wherein said 2'-modified-RNA is 2'-OMe-RNA.

In a further preferred embodiment, said oligomeric compound comprises, preferably is, the sequence of SEQ ID NO:29. In a further preferred embodiment, said oligomeric compound comprises, preferably is, the sequence of SEQ ID NO:29, wherein said 2'-modified-RNA is 2'-OMe-RNA.

In a further preferred embodiment, said oligomeric compound comprises, preferably is, the sequence of SEQ ID NO:30. In a further preferred embodiment, said oligomeric compound comprises, preferably is, the sequence of SEQ ID NO:30, wherein said 2'-modified-RNA is 2'-OMe-RNA.

In a further preferred embodiment, said oligomeric compound comprises, preferably is, the sequence of SEQ ID NO:31.

In a further preferred embodiment, said oligomeric compound comprises, preferably is, the sequence of SEQ ID NO:32.

In a further preferred embodiment, said oligomeric compound comprises, preferably is, the sequence of SEQ ID NO:33.

In a further preferred embodiment, said oligomeric compound comprises, preferably is, the sequence of SEQ ID NO:34.

In a further preferred embodiment, said oligomeric compound comprises, preferably is, the sequence of SEQ ID NO: 35.

In a further preferred embodiment, said oligomeric compound comprises, preferably is, the sequence of SEQ ID NO: 36.

In a further preferred embodiment, said oligomeric compound comprises, preferably is, the sequence of SEQ ID NO: 37.

In a further very preferred embodiment, the inventive composition is selected from any one the compositions listed in Table 3.

TABLE 3

Very preferred embodiments of the composition of the present invention.

| Name | Composition | Sequence of oligomeric compound |
|---|---|---|
| SY-0299 | $CH_3(CH_2)_{14}-C(O)NH-(CH_2)_6$-p-CCTCGGCTTACCT-p-$CH_2CH-(CH_2OH)-(CH_2)_4NH_2$ | SEQ ID NO: 1 |
| SY-0343 | $CH_3(CH_2)_{14}-C(O)NH-(CH_2)_6$-ps-CCTCGGCTTACCT-ps-$CH_2CH-(CH_2OH)-(CH_2)_4NH_2$ | SEQ ID NO: 1 |
| SY-0357 | $CH_3(CH_2)_{14}-C(O)NH-(CH_2)_6$-p-ACCTCGGCTTACC-p-$CH_2CH-(CH_2OH)-(CH_2)_4NH_2$ | SEQ ID NO: 2 |
| SY-0427 | biotin-NH-$(CH_2)_6$-p-$(CH_2)_3$-p-CCTCGGCTTACCT-OH | SEQ ID NO: 1 |
| SY-0440 | biotin-NH-$(CH_2)_6$-p-$(CH_2)_3$-p-C*C*T*C*G*G*C*T*T*A*C*C*T-OH | SEQ ID NO: 23 |
| SY-0442 | $CH_3(CH_2)_{14}-C(O)NH-(CH_2)_6$-ps-CCTCGGCTTACCT-OH | SEQ ID NO: 1 |
| SY-0443 | $CH_3(CH_2)_{14}-C(O)NH-(CH_2)_6$-ps-CCTCGGCTTACCT-ps-$CH_2CH-[CH_2$-p-$(CH_2)_3$-p-$CH_2-CH-(CH_2OH)-(CH_2)_4NH$-biotin]-$(CH_2)_4NH_2$ | SEQ ID NO: 1 |
| SY-0444 | $CH_3(CH_2)_{14}-C(O)NH-(CH_2)_6$-ps-CCTCGGCTTACCT-p-$(CH_2)_3$-p-$CH_2-CH-(CH_2OH)-(CH_2)_4NH$-biotin | SEQ ID NO: 1 |
| SY-0445 | $CH_3(CH_2)_{14}-C(O)NH-CH_2)_6$-p-CCTCGGCTTACCT-p-$CH_2CH-[CH_2$-p-$(CH_2)_3$-p-$CH_2-CH-CH_2OH)-(CH_2)_4NH$-biotin]-$(CH_2)_4NH_2$ | SEQ ID NO: 1 |
| SY-0446 | $CH_3(CH_2)_{14}-C(O)NH-(CH_2)_6$-p-CCTCGGCTTACCT-p-$(CH_2)_3$-p-$CH_2-CH-(CH_2OH)-(CH_2)_4NH$-biotin | SEQ ID NO: 1 |
| SY-0448 | $CH_3(CH_2)_{14}-C(O)NH-(CH_2)_6$-p-CC<u>u</u>CGGCTTACCT-p-$(CH_2)_3$-p-$CH_2-CH-(CH_2OH)-(CH_2)_4NH$-biotin | SEQ ID NO: 3 |
| SY-0450 | $CH_3(CH_2)_{14}-C(O)NH-(CH_2)_6$-p-CCTCGGCTTACCT-OH | SEQ ID NO: 1 |
| SY-0451 | $CH_3(CH_2)_{15}$-p-CCTCGGCTTACCT-p-$(CH_2)_3$-p-$CH_2-CH-(CH_2OH)-(CH_2)_4NH$-biotin | SEQ ID NO: 1 |
| SY-0455 | $CH_3(CH_2)_{14}-C(O)NH-(CH_2)_6$-p-CC<u>u</u>CGGCTTACCT-OH | SEQ ID NO: 3 |
| SY-0457 | $CH_3(CH_2)_{14}-C(O)NH-CH(COOH)(CH_2)_2C(O)NH-(CH_2)_6$-ps-CCTCGGCTTACCT-OH | SEQ ID NO: 1 |
| SY-0458 | $(HOOC)-(CH_2)_{16}-C(O)NH-CH(COOH)(CH_2)_2C(O)NH-(CH_2CH_2O)_2-CH_2-C(O)NH-(CH_2)_2-O-CH_2)_2$-ps-CCTCGGCTTACCT-OH | SEQ ID NO: 1 |

TABLE 3-continued

Very preferred embodiments of the composition of the present invention.

| Name | Composition | Sequence of oligomeric compound |
|---|---|---|
| SY-0459 | CH$_3$(CH$_2$)$_{14}$—C(O)NH—CH(COOH)(CH$_2$)$_2$C(O)NH—CH$_2$)$_6$-ps-CCTCGGCTTACCT-p-(CH$_2$)$_3$-p-CH$_2$—CH—(CH$_2$OH)—(CH$_2$)$_4$NH-biotin | SEQ ID NO: 1 |
| SY-0460 | (HOOC)—(CH$_2$)$_{16}$—C(O)NH—CH(COOH)(CH$_2$)$_2$C(O)NH—(CH$_2$CH$_2$O)$_2$—CH$_2$—C(O)NH—(CH$_2$)$_2$—O—(CH$_2$)$_2$-ps-CCTCGGCTTACCT-p-(CH$_2$)$_3$-p-CH$_2$—CH—(CH$_2$OH)—(CH$_2$)$_4$NH-biotin | SEQ ID NO: 1 |
| SY-0487 | CH$_3$(CH$_2$)$_{14}$—C(O)NH—(CH$_2$)$_6$-ps-AAGAuGGCATTTCTA-OH | SEQ ID NO: 4 |
| SY-0488 | CH$_3$(CH$_2$)$_{14}$—C(O)NH—(CH$_2$)$_6$-ps-CCuCGGCTTACCT-OH | SEQ ID NO: 3 |
| SY-0489 | CH$_3$(CH$_2$)$_{14}$—C(O)NH—CH(COOH)(CH$_2$)$_2$C(O)NH-(CH$_2$)$_6$-ps-AAGAuGGCATTTCTA-OH | SEQ ID NO: 4 |
| SY-0490 | (HOOC)—(CH$_2$)$_{16}$—C(O)NH—CH(COOH)(CH$_2$)$_2$C(O)NH—(CH$_2$CH$_2$O)$_2$—CH$_2$—C(O)NH—(CH$_2$)$_2$—O—(CH$_2$)$_2$-ps-AAGAuGGCATTTCTA-OH | SEQ ID NO: 4 |
| SY-0491 | CH$_3$(CH$_2$)$_{14}$—C(O)NH—(CH$_2$)$_6$-ps-CATCCTGgAGTTCCT-OH | SEQ ID NO: 5 |
| SY-0492 | CH$_3$(CH$_2$)$_{14}$—C(O)NH—(CH$_2$)$_6$-ps-GCCATCCTGgAGTTC-OH | SEQ ID NO: 6 |
| SY-0493 | CH$_3$(CH$_2$)$_{14}$—C(O)NH—(CH$_2$)$_6$-ps-CCGCTGCCCAATGCC-OH | SEQ ID NO: 7 |
| SY-0494 | CH$_3$(CH$_2$)$_{14}$—C(O)NH—(CH$_2$)$_6$-ps-ACTTcATCCCACTGA-OH | SEQ ID NO: 8 |
| SY-0495 | CH$_3$(CH$_2$)$_{14}$—C(O)NH—(CH$_2$)$_6$-ps-ATTTCATTCAACTGT-OH | SEQ ID NO: 9 |
| SY-0496 | CH$_3$(CH$_2$)$_{14}$—C(O)NH—(CH$_2$)$_6$-ps-CTGGAGTTCCTGTAA-OH | SEQ ID NO: 10 |
| SY-0497 | CH$_3$(CH$_2$)$_{14}$—C(O)NH—(CH$_2$)$_6$-ps-CTGgAGTTCCTGTAA-OH | SEQ ID NO: 11 |
| SY-0498 | CH$_3$(CH$_2$)$_{14}$—C(O)NH—(CH$_2$)$_6$-ps-TCCTGgAGTTCCTGT-OH | SEQ ID NO: 12 |
| SY-0499 | CH$_3$(CH$_2$)$_{14}$—C(O)NH—(CH$_2$)$_6$-ps-GTGTTCTTGTaCTTC-OH | SEQ ID NO: 13 |
| SY-0500 | CH$_3$(CH$_2$)$_{14}$—C(O)NH—(CH$_2$)$_6$-ps-CTGAaGGTGTTCTTG-OH | SEQ ID NO: 14 |
| SY-0501 | CH$_3$(CH$_2$)$_{14}$—C(O)NH—(CH$_2$)$_6$-ps-CTCCGGTTcTGAAGG-OH | SEQ ID NO: 15 |
| SY-0502 | CH$_3$(CH$_2$)$_{14}$—C(O)NH—(CH$_2$)$_6$-ps-TTGAATCCTuTAACA-OH | SEQ ID NO: 16 |
| SY-0503 | CH$_3$(CH$_2$)$_{14}$—C(O)NH—(CH$_2$)$_6$-ps-CTTTCaTAATGCTGG-OH | SEQ ID NO: 17 |
| SY-0504 | CH$_3$(CH$_2$)$_{14}$—C(O)NH—(CH$_2$)$_6$-ps-CTTTCATAAuGCTGG-OH | SEQ ID NO: 18 |
| SY-0505 | CH$_3$(CH$_2$)$_{14}$—C(O)NH—(CH$_2$)$_6$-ps-A*AGAuGGCATTTCTA-OH | SEQ ID NO: 24 |
| SY-0506 | CH$_3$(CH$_2$)$_{14}$—C(O)NH—(CH$_2$)$_6$-ps-A*A*GAuGGCATTTCTA-OH | SEQ ID NO: 25 |
| SY-0507 | CH$_3$(CH$_2$)$_{14}$—C(O)NH—(CH$_2$)$_6$-ps-A*A*G*AuGGCATTTCTA-OH | SEQ ID NO: 26 |
| SY-0508 | CH$_3$(CH$_2$)$_{14}$—C(O)NH—(CH$_2$)$_6$-ps-A*A*G*A*uGGCATTTCTA-OH | SEQ ID NO: 27 |
| SY-0509 | CH$_3$(CH$_2$)$_{14}$—C(O)NH—(CH$_2$)$_6$-ps-A*A*G*A*u*GGCATTTCTA-OH | SEQ ID NO: 28 |
| SY-0510 | CH$_3$(CH$_2$)$_{14}$—C(O)NH—(CH$_2$)$_6$-ps-A*A*G*A*u*G*GCATTTCTA-OH | SEQ ID NO: 29 |
| SY-0511 | CH$_3$(CH$_2$)$_{14}$—C(O)NH—(CH$_2$)$_6$-ps-A*A*G*A*u*G*G*CATTTCTA-OH | SEQ ID NO: 30 |
| SY-0512 | CH$_3$(CH$_2$)$_{14}$—C(O)NH—(CH$_2$)$_6$-ps-A*AGATGGCATTTCTA-OH | SEQ ID NO: 31 |
| SY-0513 | CH$_3$(CH$_2$)$_{14}$—C(O)NH—(CH$_2$)$_6$-ps-A*A*GATGGCATTTCTA-OH | SEQ ID NO: 32 |
| SY-0514 | CH$_3$(CH$_2$)$_{14}$—C(O)NH—(CH$_2$)$_6$-ps-A*A*G*ATGGCATTTCTA-OH | SEQ ID NO: 33 |
| SY-0515 | CH$_3$(CH$_2$)$_{14}$—C(O)NH—(CH$_2$)$_6$-ps-A*A*G*A*TGGCATTTCTA-OH | SEQ ID NO: 34 |
| SY-0516 | CH$_3$(CH$_2$)$_{14}$—C(O)NH—(CH$_2$)$_6$-ps-A*A*G*A*T*GGCATTTCTA-OH | SEQ ID NO: 35 |
| SY-0517 | CH$_3$(CH$_2$)$_{14}$—C(O)NH—(CH$_2$)$_6$-ps-A*A*G*A*T*G*GCATTTCTA-OH | SEQ ID NO: 36 |
| SY-0518 | CH$_3$(CH$_2$)$_{14}$—C(O)NH—(CH$_2$)6-ps-A*A*G*A*T*G*G*CATTTCTA-OH | SEQ ID NO: 37 |

TABLE 3-continued

Very preferred embodiments of the composition of the present invention.

| Name | Composition | Sequence of oligomeric compound |
|---|---|---|
| SY-0519 | $CH_3(CH_2)_{14}$-C(O)NH-$(CH_2)_6$-ps-CAGCAgCAGCAGCAGCAG-OH | SEQ ID NO: 20 |
| SY-0520 | $CH_3(CH_2)_{14}$-C(O)NH-$(CH_2)_6$-ps-GCCTGGACAGCTCCT-OH | SEQ ID NO: 21 |
| SY-0521 | p-AAGAuGGCATTTCTA-ps-$CH_2CH$-$(CH_2OH)$-$(CH_2)_4NHC(O)$-$(CH_2)_{14}$-$CH_3$ | SEQ ID NO: 4 |
| SY-0522 | biotin-NH-$(CH_2)_6$-p-$(CH_2)_3$-p-AAGAuGGCATTTCTA-ps-$CH_2CH$-$(CH_2OH)$-$(CH_2)_4NHC(O)$-$CH_2)_{14}$-$CH_3$ | SEQ ID NO: 4 |
| SY-0523 | p-AAGAtGGCATTTCTA-OH | SEQ ID NO: 22 |
| SY-0524 | biotin-NH-$(CH_2)_6$-p-$(CH_2)_3$-p-AAGAtGGCATTTCTA-OH | SEQ ID NO: 22 |
| SY-0526 | $CH_3(CH_2)_{14}$-C(O)NH-$(CH_2)_6$-p-AAGATGGCATTTCTA-OH | SEQ ID NO: 19 |
| SY-0527 | $CH_3(CH_2)_{14}$-C(O)NH-$(CH_2)_6$-ps-AAGATGGCATTTCTA-OH | SEQ ID NO: 19 |
| SY-0543 | $CH_3(CH_2)_{14}$-C(O)NH-$(CH_2)_6$-p-AAGAuGGCATTTCTA-OH | SEQ ID NO: 4 | ps = 5'-OP(O)(SH)-3', meaning that ps = -OP(O)(SH)-> when at the 5'-end of the oligomeric compound and ps = <-P(O)(SH)O- when at the 3'-end of the oligomeric compound, wherein the > and < indicate the attachment of the P to the 5'O- and 3'O atoms of the corresponding nucleotide;
p = 5'-OP(O)(OH)-3', meaning that p = -OP(O)(OH)-> when at the 5'-end of the oligomeric compound and p = <-P(O)(OH)O- at the 3'-end of the oligomeric compound, wherein the > and < indicate the attachment of the P to the 5'O- and 3'O atoms of the corresponding nucleotide;
wherein an * between two nucleosides indicates a phosphorothioate internucleoside linkage group, the absence of an * between two nucleosides indicates a phosphorodiester internucleoside linkage group, the capitalized letters A, C, G, and T indicate tc-DNA nucleosides (A, C, G, T = tc-DNA); the lowercase letters a, c, u, g, and t indicate 2'-O-methyl-RNA nucleosides (a, c, g, u = 2'-OMe-RNA), the nucleobase at all C positions is 5-methylcytosine, the nucleobase at all c positions is cytosine, and the primed lowercase letters a', u', g', and t' indicate deoxyribonucleosides;

t=dT-internal palm:

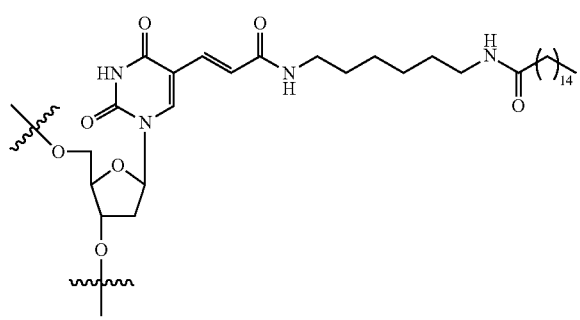

In a further very preferred embodiment, the inventive composition comprises, preferably is, SY-0299.
In a further very preferred embodiment, the inventive composition comprises, preferably is, SY-0343.
In a further very preferred embodiment, the inventive composition comprises, preferably is, SY-0357.
In a further very preferred embodiment, the inventive composition comprises, preferably is, SY-0427.
In a further very preferred embodiment, the inventive composition comprises, preferably is, SY-0440.
In a further very preferred embodiment, the inventive composition comprises, preferably is, SY-0442.
In a further very preferred embodiment, the inventive composition comprises, preferably is, SY-0443.
In a further very preferred embodiment, the inventive composition comprises, preferably is, SY-0444.
In a further very preferred embodiment, the inventive composition comprises, preferably is, SY-0445.
In a further very preferred embodiment, the inventive composition comprises, preferably is, SY-0446.
In a further very preferred embodiment, the inventive composition comprises, preferably is, SY-0448.
In a further very preferred embodiment, the inventive composition comprises, preferably is, SY-0450.
In a further very preferred embodiment, the inventive composition comprises, preferably is, SY-0451.
In a further very preferred embodiment, the inventive composition comprises, preferably is, SY-0455.
In a further very preferred embodiment, the inventive composition comprises, preferably is, SY-0457.
In a further very preferred embodiment, the inventive composition comprises, preferably is, SY-0458.
In a further very preferred embodiment, the inventive composition comprises, preferably is, SY-0459.
In a further very preferred embodiment, the inventive composition comprises, preferably is, SY-0460.
In a further very preferred embodiment, the inventive composition comprises, preferably is, SY-0487.
In a further very preferred embodiment, the inventive composition comprises, preferably is, SY-0488.
In a further very preferred embodiment, the inventive composition comprises, preferably is, SY-0489.
In a further very preferred embodiment, the inventive composition comprises, preferably is, SY-0490.
In a further very preferred embodiment, the inventive composition comprises, preferably is, SY-0491.
In a further very preferred embodiment, the inventive composition comprises, preferably is, SY-0492.
In a further very preferred embodiment, the inventive composition comprises, preferably is, SY-0493.
In a further very preferred embodiment, the inventive composition comprises, preferably is, SY-0494.
In a further very preferred embodiment, the inventive composition comprises, preferably is, SY-0495.

In a further very preferred embodiment, the inventive composition comprises, preferably is, SY-0496.

In a further very preferred embodiment, the inventive composition comprises, preferably is, SY-0497.

In a further very preferred embodiment, the inventive composition comprises, preferably is, SY-0498.

In a further very preferred embodiment, the inventive composition comprises, preferably is, SY-0499.

In a further very preferred embodiment, the inventive composition comprises, preferably is, SY-0487.

In a further very preferred embodiment, the inventive composition comprises, preferably is, SY-0500.

In a further very preferred embodiment, the inventive composition comprises, preferably is, SY-0501.

In a further very preferred embodiment, the inventive composition comprises, preferably is, SY-0502.

In a further very preferred embodiment, the inventive composition comprises, preferably is, SY-0503.

In a further very preferred embodiment, the inventive composition comprises, preferably is, SY-0504.

In a further very preferred embodiment, the inventive composition comprises, preferably is, SY-0505.

In a further very preferred embodiment, the inventive composition comprises, preferably is, SY-0506.

In a further very preferred embodiment, the inventive composition comprises, preferably is, SY-0507.

In a further very preferred embodiment, the inventive composition comprises, preferably is, SY-0508.

In a further very preferred embodiment, the inventive composition comprises, preferably is, SY-0509.

In a further very preferred embodiment, the inventive composition comprises, preferably is, SY-0510.

In a further very preferred embodiment, the inventive composition comprises, preferably is, SY-0511.

In a further very preferred embodiment, the inventive composition comprises, preferably is, SY-0512.

In a further very preferred embodiment, the inventive composition comprises, preferably is, SY-0513.

In a further very preferred embodiment, the inventive composition comprises, preferably is, SY-0514.

In a further very preferred embodiment, the inventive composition comprises, preferably is, SY-0515.

In a further very preferred embodiment, the inventive composition comprises, preferably is, SY-0516.

In a further very preferred embodiment, the inventive composition comprises, preferably is, SY-0517.

In a further very preferred embodiment, the inventive composition comprises, preferably is, SY-0518.

In a further very preferred embodiment, the inventive composition comprises, preferably is, SY-0519.

In a further very preferred embodiment, the inventive composition comprises, preferably is, SY-0520.

In a further very preferred embodiment, the inventive composition comprises, preferably is, SY-0521.

In a further very preferred embodiment, the inventive composition comprises, preferably is, SY-0522.

In a further very preferred embodiment, the inventive composition comprises, preferably is, SY-0523.

In a further very preferred embodiment, the inventive composition comprises, preferably is, SY-0524.

In a further very preferred embodiment, the inventive composition comprises, preferably is, SY-0525.

In a further very preferred embodiment, the inventive composition comprises, preferably is, SY-0526.

In a further very preferred embodiment, the inventive composition comprises, preferably is, SY-0527. In a further very preferred embodiment, the inventive composition comprises, preferably is, SY-0543.

Methods of Treating Diseases

The compositions described herein can be used in a method for treating a disease. In some embodiments, the disease is a disease that may be treated using an exon-skipping oligomeric compound. In some embodiments, the disease is a disease that may be treated using an antisense-mediated exon-inclusion oligomeric compound. In an embodiment of the invention, the compositions described herein cross the blood-brain barrier, thus are useful in treating diseases of the central nervous system, behavioral disorders, psychiatric disorders, and/or behavioral symptoms of diseases. In some embodiments, the disease is a disease of the central nervous system (CNS). In some embodiments, the disease is amyotrophic lateral sclerosis (ALS), Alzheimer's Disease (AD), Parkinson's Disease (PD), Multiple Sclerosis (MS), epilepsy, Creutzfeldt-Jakob, (CJ), Menkes Disease, or Huntington's Disease (HD). In some embodiments, the disease is a disease affecting cerebellar function, including, but not limited to, ataxia. In some embodiments, the disease is a disease affecting amygdala function, including, but not limited to, Urbach-Wiethe Disease. In some embodiments, the disease is a disease affecting hippocampal function, including, but not limited to, memory loss. In some embodiments, the disease to be treated is a psychiatric or behavioral disorder, including, but not limited to, mood disorders, dementia, anxiety, bipolar disorder, schizophrenia, sleep disorders, post-traumatic stress disorder (PTSD), attention-deficit hyperactivity disorder (ADHD), and depression disorders.

In some embodiments of the invention, the oligonucleotides of the present invention are used to treat sleep and/or cognitive disorders, and symptoms associated therewith. In some embodiments, the sleep disorder is insomnia or slow wave sleep disturbance. In some embodiments, the cognitive disorder is schizophrenia. Where the disease being treated is schizophrenia, both positive and negative symptoms of schizophrenia may be treated. In some embodiments, positive symptoms of schizophrenia are hallucinations, delusions, or disturbances in logical thought process. In some embodiments, negative symptoms of schizophrenia include deficit in motivation, deficit in spontaneity, inability to think abstractly, deficit in mood expression, deficit in cognition, deficit in the ability to experience pleasure, affective flattening, alogia, avolition, dysphoric mood, including anger, anxiety, and depression), disturbances in sleep pattern, poor impulse control, lack of judgment, abnormal psychomotor activity, such as pacing or rocking, and movement disorders, such as tardive dyskinesia. In some embodiments, areas of cognition, such as verbal memory, verbal fluency, memory consolidation, and executive functions, are improved by administration of one or more of the oligonucleotide compounds of the present invention. In some embodiments, slow wave sleep is increased, thereby improving cognition, with administration of one or more of the oligonucleotide compounds of the present invention. In some embodiments, the disease is selected from the group consisting of Duchenne muscular dystrophy (DMD), familial dysautonomia, spinal muscular atrophy (SMA), ataxia telangiectasia, congenital disorder of glycosylation, fronto-temporal dementia (FTD), Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, and myotonic dystrophy type 1. Methods of using tc-DNA oligonucleotides for the treatment of Duchenne muscular dystrophy (DMD), spinal muscular atrophy (SMA), spinocerebellar ataxia type 3 (SCA3), and other diseases are known in the art and are described, e.g., in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847; and 6,600,032; and U.S. Patent Application Publication Nos. 2015/0141637, 2016/0002280, 2014/0296323, and 2012/0149756, the disclosures of which are incorporated by reference herein.

Table A provides a listing of certain neurodegenerative diseases and their targets for which the compositions of the present invention are useful.

| Disease State | Target Gene |
| --- | --- |
| SMA | Survival of motor neuron 2 (SMN2) |
| ALS | Superoxide dismutase 1 (SOD1) |
|  | Acetylcholinesterase (AChE) |
|  | C9ORF72 |
|  | Glutamate receptor subunit 3 (GluR3) |
|  | P75 neurotrophin receptor (P75NTR) |
| HD | Mutant HTT |
|  | HTT |
| AD | APP |
|  | Mutated APP |
|  | GSK-3β |
| CJ | PRPc |
| SCA3 | Ataxin 3 |
| Menkes Disease | ATP7A |
| FTD | Tau |

Efficacy of the compositions described herein in treating, preventing and/or managing the indicated diseases or disorders can be tested using various models known in the art, which provide guidance for treatment of human disease. Models for diseases that may be treated using an exon-skipping oligomeric compound are described, e.g., in Siva, et al., *Nucleic Acid Therapeutics* 2014, 24, 69-86. Models for diseases that may be treated using an antisense-mediated exon-inclusion oligomeric compound are described, e.g., in Hua and Kramer, *Methods Mol. Biol.* 2012, 867, 307-323.

Genetic animal models for DMD are known in the art. The mdx mouse harbors a nonsense mutation in exon 23 of the dystrophin gene, which precludes the synthesis of full-length, wild-type dystrophin protein. Grounds, et al., *Neurobiol. Dis.* 2008, 31, 1-19. The GRMD (Golden Retriever Muscle Dystrophy) dog model lacks functional dystrophin because of a splice site mutation in intron 6, which disrupts the reading frame. In the GRMD model, as with human DMD, the progressive degradation of fibers leads to skeletal musculature decay with marked endomysial and perimysial fibrosis. Other models for DMD include dystrophin/utrophin double knockout mice, humanized DMD mice, mdx52 mice (carrying a deletion of exon 52 in murine DMD), and 4CV mice (carrying a nonsense mutation in exon53). Goyenvalle, et al., *Mol. Ther.* 2010, 18, 198-05; Bremmer-Bout, et al., *Mol. Ther.* 2004, 10, 232-240; Aoki, et al., *Mol. Ther.* 2010, 18, 1995-2005; Mitrpant, et al., *J. Gene. Med.* 2009, 11, 46-56.

Spinal muscular atrophy (SMA) is a class of inherited diseases that arise from a defect in a survival motor neuron gene (SMN1) mapped to chromosome 5q11.2-13.3. Overall, SMA is characterized by a loss of spinal cord and brainstem motor neurons, resulting in muscular atrophy from the loss of neural contact. The various SMAs have an incidence of about 1 in 6,000. Type I SMA, which is also known as Werdnig-Hoffman disease or severe infantile SMA, affects babies in their first year of life, and is generally fatal. Type II SMA, also known as intermediate SMA, affects children and causes muscle weakness such that the patients are never able to stand and walk, but may be able to sit, although weakness increases with age. Type III SMA patients are able to walk at some point in their development.

SMA is caused by the loss of a functional SMN1 gene, and a mutation in exon 7 of the SMN2 paralog that causes substantial skipping of this exon and production of only low levels of functional protein, such that SMN2 protein cannot compensate for the loss of SMN1. Cartegni, et al., *Am. J. Hum. Genet.* 2006, 78, 63-77. Oligonucleotide-mediated exon-inclusion methods for the treatment of SMA are being explored, including methods of compensating for the deleterious mutation in SMN2 by masking an intronic silencing sequence and/or a terminal stem-loop sequence within an SMN2 gene to yield a modified functional SMN2 protein, including an amino acid sequence encoded by exon 7, which is capable of at least partially complementing a non-functional SMN1 protein. See, e.g., WO 2010/115993 A1, the disclosure of which is incorporated herein by reference. Besides SMA, numerous other diseases can also be potentially treated by the exon inclusion approach provided by the inventive compositions, including those diseases described herein.

Thus, the present invention provides for a pharmaceutical composition comprising the inventive composition and further comprising a pharmaceutically acceptable carrier, wherein preferably said pharmaceutical composition is for use in the prevention, treatment or diagnosis of a neuromuscular or musculoskeletal disease, wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

The present invention provides further for the inventive pharmaceutical composition comprising the inventive composition and further comprising a pharmaceutically acceptable carrier, wherein preferably said pharmaceutical composition is for use in the treatment of a neuromuscular or musculoskeletal disease, wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

The present invention provides further for the inventive composition for use as a medicament in the prevention, treatment or diagnosis of a disease, wherein preferably said disease is a neuromuscular or musculoskeletal disease, and wherein further preferably said neuromuscular or said musculoskeletal disease is selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease), and again further preferably said neuromuscular or said musculoskeletal disease is selected from Duchenne muscular dystrophy, spinal muscular atrophy, Pompe disease, myotonic dystrophy type 2 (DM2 or proximal myotonic myopathy), and myotonic dystrophy type 1 (DM1 or Steinert disease).

EXAMPLES

The embodiments encompassed herein are now described with reference to the following examples. These examples are provided for the purpose of illustration only and the disclosure encompassed herein should in no way be construed as being limited to these examples, but rather should be construed to encompass any and all variations which become evident as a result of the teachings provided herein.
Material and Methods Animals: The mdx mouse (Bulfield et al. *Proc. Natl. Acad. Sci. USA,* 1984, 81, 1189-1192; Ryder-Cook et al., *EMBO J,* 1988, 7, 3017-3021) has a single base substitution within exon 23 of the dystrophin gene, which causes premature termination of the polypeptide chain (Sicinski et al., *Science,* 1989, 244, 1578-1580) so the full-length 427 kDa muscle isoform of dystrophin is not produced. However, the other isoforms produced from different promoters (in 3' of the point mutation) are unaffected. Mutants are viable and fertile. They have no apparent symptoms and are not mechanically impaired throughout their life span unless the muscle damage is not provoked by a mechanical or chemical injury (Reimann et al., *Neuromusc. Disord.,* 2000, 10, 276-282; Connolly et al., *Neuromusc. Disord.,* 2001, 11, 703-712).

At the histological level, mdx displays the classical features of dystrophic muscle characterized by numerous necrotic fibers with subsequent infiltration of scavenger cells (Coulton et al., *Neuropathol. Appl. Neurobiol.,* 1988, 14, 299-314). However, differing from DMD, an efficient unknown compensatory mechanism counteracts the degeneration thus up-keeping the regeneration process to restore unceasing mechanical damages. The number of revertant fibers is low, normally present at around 1% of total fibers, although their number increases with the age of the mice (Lu et al., *J. Cell. Biol,* 2000, 148, 985-995). According to the exon phasing, translation of a shortened-dystrophin is possible by skipping exon 23 in the course of the mRNA splicing.

Oligonucleotide synthesis: Oligonucleotides for in vivo experiments were synthesized on 260 µmol scale using Aekta Oligo Pilot 10 synthesizer and NittoPhase® UnyLinker™ 200, universal solid support. In case of inventive compositions comprising one or more lipid moieties and/or said spacer at the 3' end, the corresponding modified, and typically and preferably Fmoc-protected, phosphoroamidite was introduced in the first cycle of the synthesis. Modified synthetic cycle using typically 2.2 equivalent of phosphoramidites and 4 min coupling time was employed. In case of inventive compositions comprising said one or more lipid moiety and/or spacer at the 5' end, the corresponding modified, phosphoroamidite was used in the last cycle. Solid support was treated with 20% diethylamine in MeCN in order to remove Fmoc and cyanoethyl protecting groups.

Oligonucleotides for in vitro experiments were synthesized on 1 µmol scale using Expedite Nucleic Acids Synthesis System and High Load Glen UnySupport™, universal solid support. In case of inventive compositions comprising said lipid moiety and/or spacer at the 3' end, the corresponding modified phosphoroamidite was introduced in the first cycle of the synthesis. In case of inventive compositions comprising said biotin moiety and/or spacer at the 3' end, the corresponding biotin phosphoroamidite was introduced in the first cycle of the synthesis, followed by the C4 spacer phosphoramidite in the second cycle of the synthesis and corresponding, and typically and preferably Fmoc-protected, spacer phosphoroamidite in the third cycle of the synthesis. Modified synthetic cycle using typically 9 equivalent of phosphoramidites and 3.5 min coupling time was employed. In case of inventive compositions comprising said one or more lipid moiety and/or spacer at the 5' end, the corresponding modified, phosphoroamidite was used in the last cycle. Solid support was treated with 20% diethylamine in MeCN in order to remove Fmoc and cyanoethyl protecting groups.

The deprotection was carried out by heating solid supported oligonucleotide with saturated $NH_4OH$ at 65° C. for 3 h. Then the mixture was cooled down to ambient temperature, 4M NaOH and MeOH were added so that the final composition of the mixture was 0.4M NaOH and 60% MeOH and the treatment continued for additional 2.5 h at ambient temperature. Solid was filtered off, washed with $EtOH/H_2O$ 1:1 and the filtrate was neutralized by addition of 2M $NaH_2PO_4$. The resulting solution of crude oligonucleotide was desalted using TFF against water and lyophilized. In case of inventive composition comprising one or more —COOH function the conditions previously described (Surzhikov et al., *Nucleic Acids Res.,* 2000, 28, e29) were used.

The oligonucleotides for in vivo experiments were purified by isocratic RP HPLC (Waters x Bridge prep C18, 5 µm, 10×150 mm) using 42% MeCN in ammonium acetate buffer (pH 7) at 75° C. and flow rate of 4 mL/min. Fractions containing the product of sufficient purity (>70% FLP) were combined and partially lyophilized. About 20 equivalents of NaCl was added to the solution, which was subsequently desalted using TFF against water.

The oligonucleotides for in vitro experiments were purified by isocratic RP HPLC (Waters x Bridge prep C18, 5 µm, 4.6×150 mm) using about 30% iPrOH in ammonium bicarbonate buffer (pH 7) at 60° C. and flow rate of 1 mL/min. Fractions containing the product of sufficient purity were combined and subsequently desalted using SEC (GE Healthcare, HiPrep 26/10) with water as eluent.

Linking of the lipid moieties to the oligomeric compounds: Multiple approaches exist for said linking said one or more lipid moiety to the oligonucleotides either directly on solid support or in solution in accordance with the present invention. These approaches follow classical conjugation chemistry well known to the skilled person in the art and extensively described in the literature (Bioconjugate Techniques, Greg T. Hermanson, Pierce Biotechnology; Singh, Chem. Soc. Rev., 2010, 39, 2054-2070; H. Rosemeyer, Chem. Biodiversity, 2005, 2, 977-1062). As indicated, in case of inventive compositions comprising said one or more lipid moiety and/or spacer at the 3' end or 5' end, the corresponding modified, and typically and preferably Fmoc- or MMTr-protected, phosphoroamidites were introduced in the first cycle or last cycle of the synthesis.

Typical and preferred linking procedures for linking said one or more lipid moiety of formula (I), A-B—*, wherein said asterisk (*) represents the point of said covalent linkage to said oligomeric compound or to said spacer in accordance with the present invention, include but are not limited to
(i) Linking the 5'-end of the oligomeric compound and oligonucleotide, respectively, following the below reaction scheme, when B is preferably OP(O)(OH), OP(O)(SH), further preferably OP(O)(SH):
5'-HO-OLIGO-3'+A-O—P(O-PG)-X→5'-A-O—P(O-PG)-O-OLIGO-3'+HX
followed by oxidation of P(III) to P(V), wherein X is a suitable leaving group; and PG is a suitable protecting group;
(ii) Linking the 5'-end of the oligomeric compound and oligonucleotide, respectively, via phosphoroamidate chemistry following the below reaction scheme, when B is preferably NH—P(O)(OH):
5'-HO-OLIGO-3'→5'-H—(O-PG)(O)P—O-OLIGO-3'
5'-H—(O-PG)(O)P—O-OLIGO-3'+H₂N-A→5'-A-NH—(O-PG)(O)P—O-OLIGO-3', wherein PG is a suitable protecting group;
(iii) Linking the 5'-end of the oligomeric compound and oligonucleotide, respectively, via phosphoroamidate chemistry following the below reaction scheme, when B is preferably NH—P(S)(OH);
(iv) 5'-HO-OLIGO-3'→5'-X—P(O-PG)-O-OLIGO-3'
5'-X—P(O-PG)-O-OLIGO-3'+H₂N-A→5'-A-NH—P(O)(O-PG)-O-OLIGO-3'
followed by oxidation of P(III) to P(V) using suitable sulfur transfer reagent, and wherein PG is a suitable protecting group;
(v) Linking the 5'-end of the oligomeric compound and oligonucleotide, respectively, via carbamate chemistry following the below reaction schemes, when B is preferably NH—C(O):
5'-HO-OLIGO-3'→5'-X—C(O)—O-OLIGO-3'
5'-X—C(O)—O-OLIGO-3'+H₂N-A→5'-A-NH—C(O)—O-OLIGO-3'+HX
wherein X is a suitable leaving group; or
5'-HO-OLIGO-3'+OCN-A→5'-A-NH—C(O)—O-OLIGO-3';

The aforementioned linking procedures are also applicable for linking to the 3'-end of the oligomeric compound and oligonucleotide, respectively, typically upon the reversed, 5'→3' oligomeric compound and oligonucleotide synthesis, respectively.

By way of example: For the synthesis of preferred inventive compositions such as SY-0457, SY-0458, SY-0459 and SY-0460, the lipid moiety was conjugated via reaction of corresponding NHS-ester with amino-modified oligonucleotide either on solid support utilizing 10 equiv. of NHS-ester in DMSO in the presence of DIPEA (15 equiv.) or in the solution utilizing 3×10 equiv. of NHS-ester in 1:1 DMSO/buffer (0.1M NaHCO₃ pH 8.5) at 37° C.

By way of further example: For the synthesis of preferred inventive composition such as SY-0299, SY-0343, SY-0442 and SY-0455 comprising the palmitoyl residue as said one lipid moiety linked to the oligomeric compound of SEQ ID NO:1 (with full PO internucleosidic linkage groups) by way of either —NH—C₆alkylene-OP(O)(SH)— or —NH—C₆alkylene-OP(O)(OH)-spacer to the 5' end OH-group of said oligomeric compound, the 5'-Palmitate-CE-Phosphoramidite (Link, P/N 2199) was used as phosphoroamidite in the last cycle. The moiety attached to the 3' end of SY-0343 and SY-0299, namely the —P(O)(SH)O—CH₂CH—(CH₂OH)—(CH₂)₄NH₂ moiety was introduced in the first cycle of the synthesis via coupling of the corresponding Fmoc-protected phosphoroamidite to the OH group of the 3'end of the first nucleotide.

The specific and preferred compositions of the present invention and used in the experimental section are characterized in particular in Table 3 by further reference to their names and abbreviations, respectively, which are typically used throughout this specification.

Analysis of oligonucleotides by RP-HPLC-DAD-MS: Following parameters were used for analytical HPLC: C18 column with a particle size of 1.7 μm was used. The column temperature was set to 75° C. Mobile phase A was 400 mM hexafluoroisopropanol (HFIP) and 15 mM triethylamine+10% methanol. Mobile phase B was methanol. A gradient of 32 to 52% mobile phase B was applied. The flow rate was set to 0.25 mL/min. The oligonucleotides were detected using a UV photometer at 260 nm and a time-of-flight mass spectrometer.

Detection of multimers: Polyacrylamide-gel electrophoresis (PAGE) experiments were performed to detect self-multimers. The following chemicals were used: Tris(hydroxymethyl)aminomethane (Tris), (TCI A0321); acetic acid (Merck 1.00063); acrylamide/Bis solution, 29:1 (40%, Serva 10680.01); tetramethylethylenediamine (TEMED, Sigma-Aldrich T9281); ammonium persulfate (Sigma-Aldrich 248614); and glycerol (Sigma-Aldrich G9012). Buffer solution A was prepared by dissolving 60 g of Tris in 200 mL of water. The pH is adjusted to 7.4 with glacial acetic acid (about 25-30 mL). The solution is diluted to 500 mL with water and stored at +4° C. Buffer solution B was prepared by diluting 16 mL of buffer solution A to 800 mL with water. Ammonium persulfate 10% (w/v) was prepared by dissolving 100 mg of ammonium persulfate are dissolved in 0.9 mL of water. The preparation of gel was performed by mixing the following solutions in a glass beaker: 9.4 mL acrylamide/Bis solution; 15 mL water; 500 μL of buffer solution A; 125 μL of ammonium persulfate 10% (w/v), and 38 μL of TEMED. The test solution was 1 mg/mL in 10% glycerol, and 10 μL was applied (equal to 10 μg of oligonucleotide). The pre-migration settings were 40 min/90 V with buffer solution B. The migration settings were 90 min/90 V or 15 min/90 V plus 45-60 min/120 V with buffer solution B. 5-7 μL of 6×DNA loading dye was also migrated. Detection was performed by placing the gel on a TLC plate and examining under UV light at 254 nm. Afterwards, staining with Stains-All (Sigma-Aldrich, 1-Ethyl-2-[3-(1-ethylnaphtho[1,2-d]thiazolin-2-ylidene)-2-methylpropenyl]naphtho[1,2-d]thiazolium bromide, 3,3'-diethyl-9-methyl-4,5,4',5'-dibenzothiacarbocyanine) according to the manufacturer's protocol was performed.

Isolation of proteins interacting with oligonucleotides: Isolation of blood proteins was performed with biotinylated oligonucleotides immobilized on streptavidin beads (High Capacity Streptavidin Agarose, Pierce). Biotinylated oligonucleotides were immobilized on the beads (10 μl of beads for 20 μg of oligonucleotide) for 30 min and an excess of oligonucleotides was removed by 3 washing with phosphate buffered solution (PBS). Thus prepared beads were incubated with 5 to 50 µl of mouse or human sera for one hour and then non-bound proteins were removed by 4 consecutive washing in PBS. After the last washing the precipitated proteins were dissolved in the Laemmli sample buffer for further analysis by SDS-PAGE or directly digested with trypsin for mass spectrometry analysis on ORBI-TRAP instrument.

Commercially available human serum (SIGMA, St. Louis, MO) or serum samples from healthy human adults obtained in accordance with regulatory guidelines were used in the experiments. C57BL/6 mouse blood samples were collected from tail vein or retro-orbital plexus. All the procedures involving animals were performed according to the guidelines of the Animal Ethical Committee of our Institute.

Identification of captured proteins by mass spectrometry using OrbiTrap technology: For mass spectrometry analysis, precipitated proteins were directly digested by trypsin in a buffer containing 100 mM ammonium carbonate pH 8.0 and 500 ng of trypsin (Sequence Grade Trypsin, Promega) for 16 h at 37° C. and stored at −20° C. until use. The peptide mixture was desalted using ZipTip µ-C18 Pipette Tip (Millipore) and separated with an Easy nano-LC Proxeon system (Thermo Fisher Scientific) equipped with a reversed phase C18 column (Easy-Column Proxeon C18, L 15 cm, ID 75 µm). Eluates were monitored by a LTQ VelosOrbitrap mass spectrometer (Thermo Fisher Scientific) and tandem MS (MS/MS) data were processed with Proteome Discoverer 1.4 software (Thermo Fisher scientific) coupled to an in house Mascot search server (Matrix Science, 2.3.2 213 version) using SwissProt database as described previously (Rouillon, 2015). The relative abundance of each protein identified was estimated by label-free quantification using the Progenesis LC MS software (Nonlinear Dynamics, 4.0 version). Average Normalized Abundances (ANA) reflecting the relative quantities of proteins in Progenesis analysis, were used to compare quantities of protein bound to a vector.

Protein identification after SDS-PAGE separation: Protein identification was performed as described before (Denard, *Proteomics*, 2009, 9, 3666-3676). After separation of isolated proteins on SDS-PAGE (4 to 12% gradient, NuPAGE Novex Bis-Tris Gel 1.0 mm, Life Technologies), gels were visualized by staining with Coomassie blue (InstantBlue Protein Stain, Expedion) and bands of interest were sliced for further analysis. Gel slices were washed in 1 ml with 96% of $CH_2CHOH$ for 10 min, and then alcohol was carefully removed and replaced by 20 µl of a solution containing 100 mM ammonium carbonate pH 8.0 and 100 ng of trypsin (Promega). Samples were digested for 16 h at 37° C., then stored at −20° C. until use. The peptide mixture was desalted using ZipTip µ-C18 Pipette Tip (Millipore) and deposed on MALDI plaque with α-Cyano-4-hydroxycinnamic acid (HCCA) (5 µg) matrix in 80% acetonitrile, 0.10% formic acid.

MALDI-TOF MS analysis was performed on a MALDI TOF/TOF ABI 4800+ (AB Sciex). All spectra were acquired in a positive reflector mode. The resulting mass list was searched using in house Mascot search server (Matrix Science, 2.3.2 213 version) and SwissProt database human/mouse, one missed cleavage site and mass tolerance setting of 50 ppm taking into consideration partial oxidation of methionine.

Systemic administration of AONs: Animal procedures were performed in accordance with national and European legislation, approved by the French government (Ministère de l'Enseignement Supérieur et de la Recherche, Autorisation APAFiS #6518). Mdx (C57BL/10ScSc-Dmdmdx/J) and C57BL/10 mice were bred in our animal facility at the Platform 2Care, UFR des Sciences de la santé, Université de Versailles Saint Quentin and were maintained in a standard 12-hour light/dark cycle with free access to food and water. Mice were weaned at weeks 4-5 postnatal and 2-5 individuals were housed per cage.

Six-eight week old mdx mice were injected intravenously in the retro-orbital sinus, under general anesthesia using 1.5-2% isoflurane, once a week with different AONs (15mer or 13mer, PO or PS, conjugated or not) for a period of ranging from 4-12 weeks. An age-matched C57/BL10 (WT) group and mdx group receiving an equivalent volume of sterile saline were included as controls. One hour after the first injection, blood samples were collected from all mice to measure complement C3 and cytokines/chemokines levels. Additional blood samples were collected one week after the 6th injection (mid-treatment) and one week after the end of the treatment. Mice were then placed in metabolic cages for urine collection over a period of 24 h. Animals were sacrificed 2 weeks after the last injection. Muscles and tissues were harvested and snap-frozen in liquid nitrogen-cooled isopentane and stored at −80° C. before further analysis. Sample sizes and n values are indicated in each figure legend. Investigators were blinded for RNA and protein analysis.

Serum and urine analysis: Blood samples were collected from tail bleeds under general anesthesia. Analyses of serum creatine kinase (CK), alanine aminotransferase (ALT), aspartate aminotransferase (AST), alkaline phosphatase (ALP), bilirubin, creatinine, urea and albumin levels were performed by the pathology laboratory at Mary Lyon Centre, Medical Research Council, Harwell, Oxfordshire, UK. Cytokines and chemokines levels in serum were analyzed by multiplex assays, using the Luminex® technology. A Bio-Plex Pro Mouse Cytokine 10-Plex Immunoassay panel (Bio-Rad, Hercules, CA) was used to detect levels of IL-1β, IL-6, IL-10, IL-12p70, IL-13, IL-17, IFN-γ, MCP-1, RANTES and TNF-α according to the manufacturer's instructions. Immunoassays were read using a Bio-Plex MAGPIX Multiplex reader and results analyzed with the Bio-Plex manager 6.1 software (Bio-Rad, France).

Urine was collected using metabolic cages over 24 h, directly in refrigerated tubes (4° C.). Upon collection, urines were centrifuged at 10,000×g for 10 min and supernatant was aliquoted and frozen at −80° C. for further analysis. Urine creatinine was measured using Creatinine assay kit (R&D Systems, Inc, Minneapolis, MN) following manufacturer's instructions. Total protein in urine samples was measured as previously described (Swayze et al., *Nucleic Acids Res.*, 2007, 35, 687-700). Briefly, proteins were precipitated from urine samples by adding 40 µL $dH_2O$ and 200 µL of prechilled acetone to 10 µL of urine. Samples were then incubated at −20° C. for 30 min, then centrifuged at 14,000×g, 4° C. for 15 min. Pellets were resuspended in 40 µl dH$_2$O and protein concentration was measured using Pierce BCA assay (Thermo Scientific, Rockford, IL). Albumin from urine samples was measured using the albumin ELISA kit (Bethy Laboratories, Montgomery, TX) following manufacturer's instructions. Acute kidney injury (AKI) biomarkers levels were analyzed by multiplex assays, using the Luminex® technology. The multiplex kidney injury panels (MKI1MAG-94K, MKI2MAG-94K, Merck-Millipore) were used according to the manufacturer's instructions to measure levels of β-2-microglobulin (B2M), Renin, Kidney Injury Molecule 1 (KIM-1), interferon-gamma induced protein 10 (IP-10), Vascular endothelial growth factor (VEGF), Cystatin C, epidermal growth factor (EGF), Lipocalin-2-NGAL, Clusterin and Osteopontin (OPN). The results were read using a Bio-Plex MAGPIX Multiplex reader and analyzed with the Bio-Plex manager 6.1 software (Bio-Rad, France).

Assays for complement activation: Complement activation in mouse serum samples was measured by Microvue PanSpecific-C3 converter and SC5b-9 Plus kits (Quidel Co., San Diego CA, USA). Briefly, mouse C3 protein is converted to human SC5b9 using a C3 converter reagent (Pan specific C3 reagent kit, Microvue, Quidel then detected by SC5b9 Elisa (Quidel).

For in vitro complement activation studies, AON molecules were incubated with normal pooled human serum (1:10) (Seralab, UK) at 37° C. for 45 minutes. Determination of complement activation was evaluated using human SC5b-9 Plus kit (Quidel Co., San Diego CA, USA). 5 mg/ml Zymosan (Complement Technology, Inc, Texas, USA) was used as positive control. Complement activation was expressed as a percentage of lasting levels of C3 in samples considering levels of C3 in the PBS condition at 100% of C3 (no activation).

Coagulation assays: Mouse blood samples were collected into tubes containing of 3.2% sodium citrate. Whole blood samples were centrifuged at 2,500×g for 15 min and then plasma were immediately separated and stored at −80° C. until use. Two mg/mL of tcDNA-AONs were incubated with 50 µL of citrated plasma C for 30 min at 37° C., then the prothrombin time (PT) and the activated partial thromboplastin time (aPTT) assays were performed on a semi-automated START max coagulometer (Stago) following manufacturer's instructions.

RNA analysis: Total RNA was isolated from intervening muscle sections collected during cryosection using TRIzol reagent according to the manufacturer's instructions (ThermoFisher Scientific, USA). Aliquots of 500 ng of total RNA were used for RT-PCR analysis using the Access RT-PCR System (Promega, USA) in a 50 µL reaction using the external primers:

```
Ex 20Fo
(5'-CAGAATTCTGCCAATTGCTGAG-3' - SEQ ID NO: 38)
and

Ex 26Ro
(5'-TTCTTCAGCTTGTGTCATCC-3' - SEQ ID NO: 39).
```

The cDNA synthesis was carried out at 45° C. for 45 min, directly followed by the primary PCR of 30 cycles of 95° C. (30 s), 55° C. (1 min) and 72° C. (2 min). Two µL of these reactions were then re-amplified in nested PCRs by 22 cycles of 95° C. (30 s), 55° C. (1 min) and 72° C. (2 min) using the internal primers:

```
Ex 20Fi
(5'-CCCAGTCTACCACCCTATCAGAGC-3' - SEQ ID NO: 40)
and

Ex 26Ri
(5'-CCTGCCTTTAAGGCTTCCTT-3' - SEQ ID NO: 41).
```

PCR products were analyzed on 2% agarose gels. Exon 23 skipping was also measured by Taqman quantitative RT-PCR as previously described (Goyenvalle et al., *Hum. Mol. Genet.*, 2012, 21, 2559-2571; Straub et al., *Lancet Neurol.*, 2016, 15, 882-890).

Total RNA was also isolated from renal cortex samples as previously described (Frazier et al., *Toxicol. Pathol.*, 2014, 42, 923-935) and quantitative RT-PCR performed on kidney injury biomarkers (KIBs) genes: Interferon gamma (IFNg), Interleukin 6 (IL6), Granzyme B (Gzmb), interferon-gamma induced protein 10 (IP-10), Tumor Necrosis Factor (TNF), Chemokine ligand 2 (Ccl2), Chemokine ligand 3 (Ccl3), β-2-microglobulin (B2M), Kidney Injury Molecule 1 (KIM-1), Renin 1 (Ren1) and epidermal growth factor (EGF).

Statistical analysis: Data were analyzed by GraphPad Prism5 software (San Diego, California, USA) and shown as the means S.E.M. "n" refers to the number of mice per group. Comparisons of statistical significance were assessed by non-parametric Mann-Whitney U tests. Significant levels were set at *$P<0.05$, $P<0.01$, *$P<0.001$.

As described herein, the oligomeric compound comprised by the inventive compositions is in preferred embodiments an antisense oligonucleotide (AON) designed in order to be complementary of a specific mRNA or pre-mRNA. This preferred class of compounds of the present invention can be used for the treatment of numerous diseases. The illustrative disease provided below do not limit the invention, and the inventive compositions provided can be used for the treatment of any disease treatable by the administration of an AON.

Example 1

Inventive Compositions for the Treatment of Duchenne Muscular Dystrophy

Evaluation of Efficacy

Adult mdx mice were treated weekly over 4 weeks with intravenous injections of different 13-mer AONs targeting the donor splice site of exon 23 of the dystrophin pre-mRNA (M23D: +2-11), namely with either SY-0308, SY-0210 and the inventive SY-0299, SY-0343, SY-0442 and SY-0455. SY-0308 (also named "tcDNA-PO M23D" interchangeably herein) corresponds to p-CCTCGGCTTACCT-OH of SEQ ID NO:1, with all nucleotides being tc-DNAs and all internucleosidic linkage groups being phosphorodiester linkage groups, and p being a phosphate moiety at the 5' end. SY-0210 (also named "tcDNA-PS M23D" interchangeably herein) corresponds to p-CCTCGGCTTACCT-OH of SEQ ID NO:1, with all nucleotides being tc-DNAs and all internucleosidic linkage groups being phosphorothioate linkage groups, and p being a phosphate moiety at the 5' end. The inventive composition SY-0343 is herein interchangeably referred to as "Palm-2PS-tcDNA-PO M23D" which is depicted in the following:

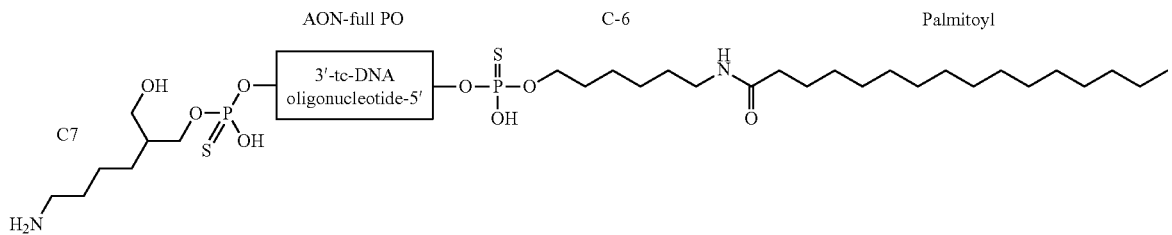

The inventive composition SY-0442 is herein interchangeably referred to as "Palm-1PS-tcDNA-PO M23D" which is depicted in the following:

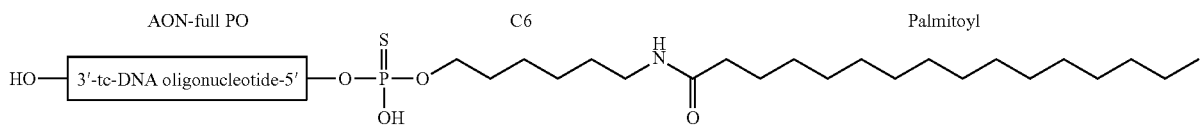

The inventive composition SY-0299 is herein interchangeably referred to as "Palm-2PO-tcDNA-PO M23D" which is depicted in the following:

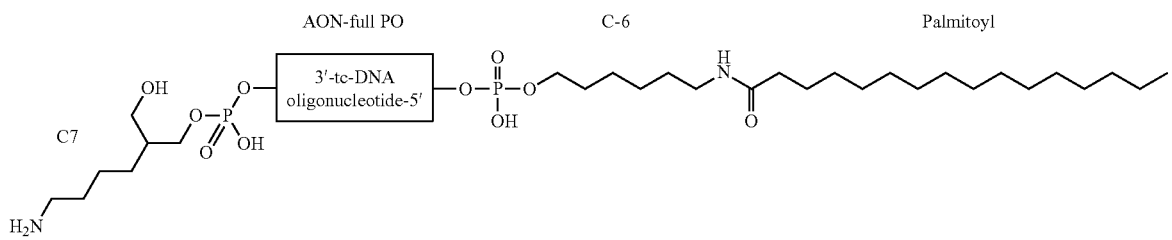

The inventive composition SY-0455 is herein interchangeably referred to as "Palm-1PO-tcDNA/2OMe-PO M23D" which is depicted in the following:

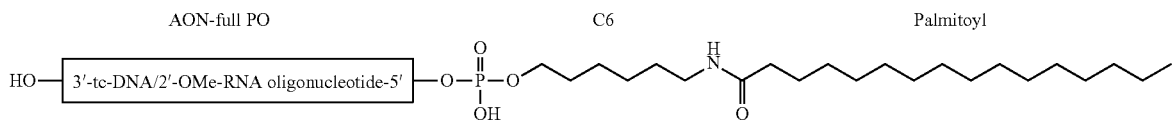

Figure 5:
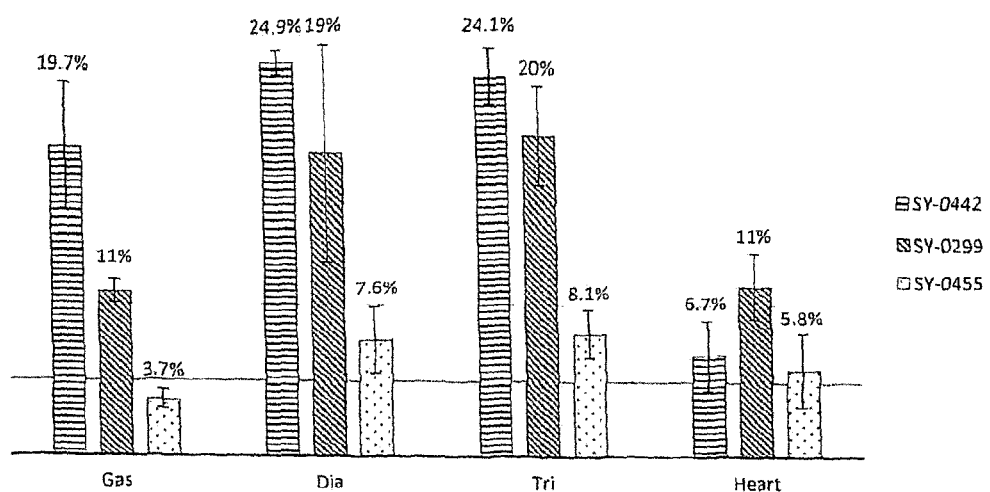
FIG. 5: Levels of restored dystrophin quantified by Western blot using licor Odyssey system in gastrocnemius (Gas), diaphragm (Dia), triceps (Tri), after 4 weeks of treatment with a dosage of 200 mg/kg/wk of SY-0299, SY-0455, and SY-0442.
Figure 6A:
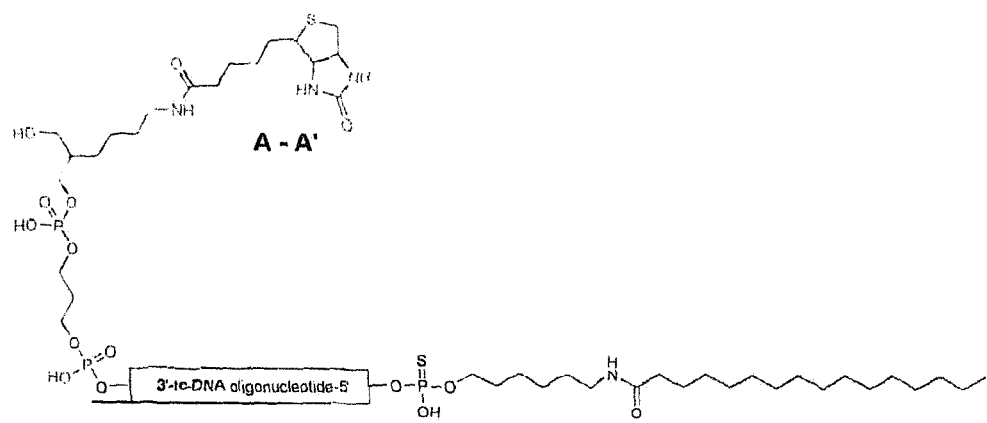
FIG. 6: Biotinylated tcDNA oligonucleotides (M23D) used for co-precipitation of potentially interacting proteins from mouse and human sera. A: SY-0446; A': SY-0448 analog to SY-0446, except that the third nucleotide of the tcDNA sequence has been changed into a 2'OMe-U. B: SY-0445. C: SY-0443 analog to SY-0445, except that two PS are present at both ends of the tcDNA oligonucleotide. D: SY-0451. For AONs without palmitoyl residues (SY-0440 and SY-0427), the biotin moiety was attached at the 5' end of the oligonucleotide through a C3 linker (not shown). Characterization and definition of the inventive compositions are described in Table 3.
Figure 6B:
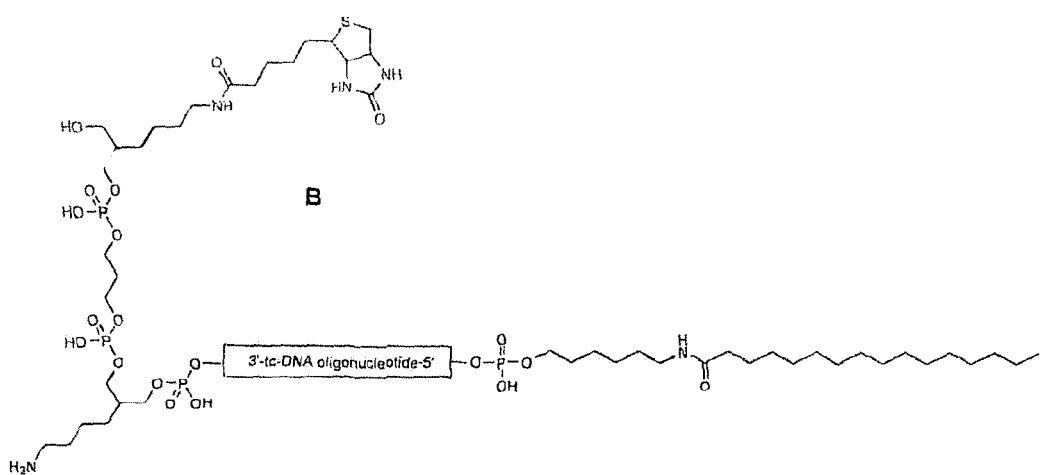
Figure 6C:
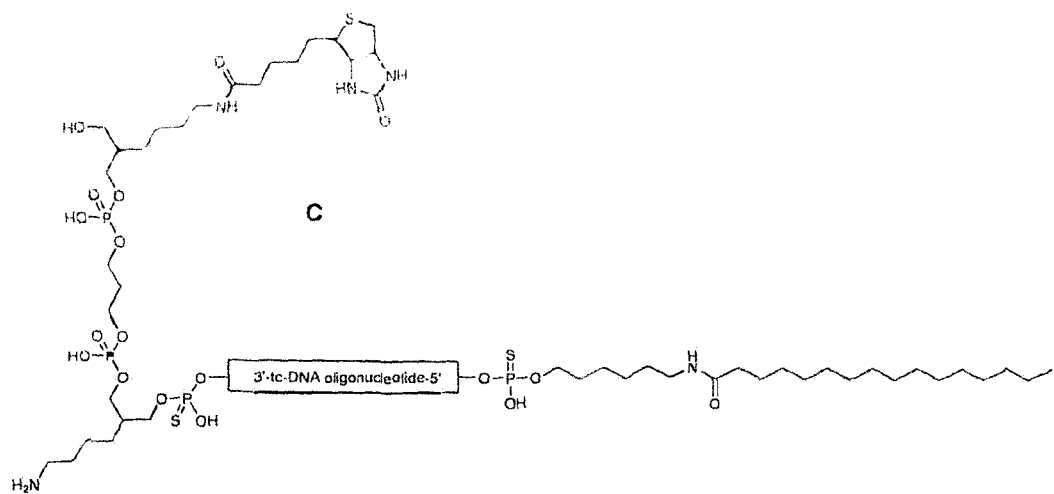
Figure 6D:
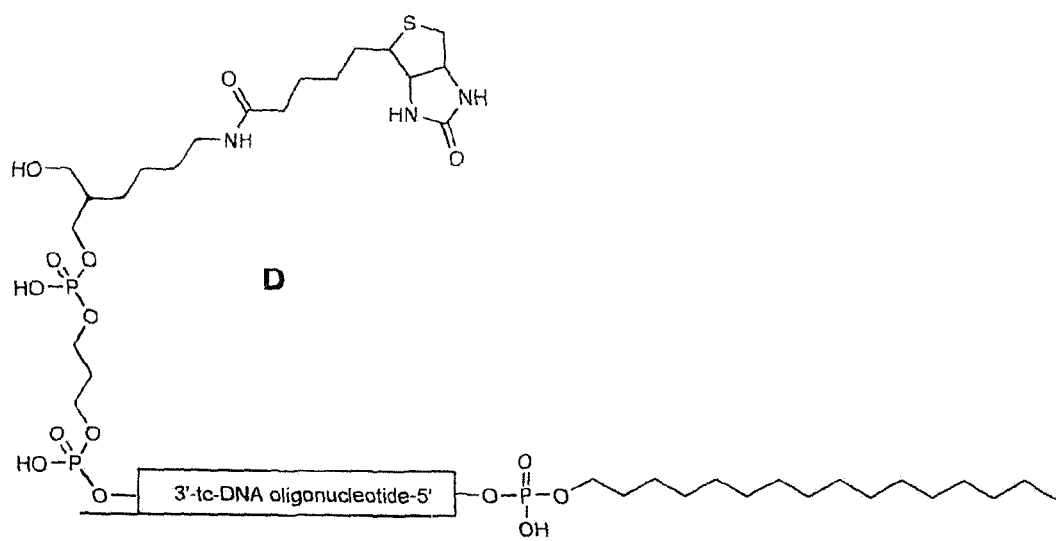

SY-0308, SY-0210, SY-0299, SY-0442 and SY-0455 were used at the dose of 200 mg/kg/week of body weight, while SY-0343 was used at the dose of 178 mg/kg/week. Two weeks after the last injection, muscles were harvested and RNA samples were analyzed by quantitative RT-PCR to determine skipping levels of exon 23 of the dystrophin gene (FIG. 1) and levels of restored dystrophin was quantified by Western blot using licor Odyssey system (FIG. 5). FIG. 1 shows that the levels of skipping were always consistently higher for palmitoyl conjugated-AON than for tcDNA-PO M23D. The levels of exon 23 skipping were also higher in most of the tissues of mice treated with palmitoyl conjugated-AON's compared to those treated with tcDNA-PS M23D AON, with the most pronounced difference in the heart, cortex and cerebellum. The percentage of exon 23-skipped dystrophin mRNA exceeded the 15% value for several skeletal muscles and the heart. For the heart, fold changes between each of SY-0299, SY-0343, SY-0442 and SY-0455 to SY-0308 or to SY-0210 were 4.4 to 9.2 and 4.0 to 8.5, respectively. Importantly, skipping was clearly detected in the cortex and the cerebellum soon after 4 weeks of treatment with the palmitoyl conjugated-AON but not yet with the two other compounds.

Thus, palmitoyl conjugated-tcDNA AONs with internucleosidic linkage groups being PO are more efficient than their naked tcDNA equivalent AONs with or without PS bonds.

This example shows that systemic delivery of the inventive compositions comprising the antisense oligomers linked with said 5'-palmitoyl-C6-amino lipid moiety and spacer and having a full PO backbone (Palmitoyl conjugated PO M23D) allowed greater rescue of dystrophin, compared to equivalent sequences made of tcDNA with either PO or PS backbones.

Evaluation of Toxicity

No marked clinical signs were observed during the course of the experiments with the three types of AONs targeting the (M23D: +2-11) region of the dystrophin in the mouse. However, acute deleterious effects have been observed with other sequences of interest, for example, (H51: +67+81-AAGATGGCATTTCTA—SEQ ID NO: 19) targeting exon 51 of the human dystrophin, herein named SYN51. Thus, SY-0206, also named "tcDNA-PS SYN51" interchangeably herein, and corresponding to p-AAGATGGCATTTCT-OH of SEQ ID NO:19, with all nucleotides being tc-DNAs and all internucleosidic linkage groups being phosphorothioate linkage groups, and p being a phosphate moiety at the 5' end, threatening further clinical developments. Historically, the PO internucleosidic linkage group was substituted by the PS internucleosidic linkage group to stabilize oligomers and prevent their degradation. Even though tcDNA oligonucleotides are extremely stable, and, thus, modification and substitution of the PO by the PS modification was not required a priori, such a modification, nevertheless, as shown in FIG. 1, profoundly increased tcDNA-PS biodistribution after systemic delivery allowing a better widespread skipping efficacy compared to tcDNA-PO. This phenomenon was likely due to increased interactions of PS residues with serum proteins.

One of the major acute effects of toxic tcDNA-PS AONs was that they caused blood clotting, thrombosis and complement activation.

Here, we used two complementary blood clotting tests, Prothrombin time (PT) and partial thromboplastin time (aPTT), to check for potential bleeding problems induced by different tcDNA AONs, namely SY-0308 (tcDNA-PO M23D), SY-0210 (tcDNA-PS M23D), SY-0343 (Palm-2PS-tcDNA-PO M23D), SY-0442 (Palm-1PS-tcDNA-PO M23D), SY-0455 (Palm-1PO-tcDNA/2OMe-PO M23D), SY-0206 (tcDNA-PS SYN51) and SY-0252. SY-0252 also named "tcDNA-PO SYN51" interchangeably herein, corresponds to p-AGATGGCATTTCT-OH of SEQ ID NO:19, with all nucleotides being tc-DNAs and all internucleosidic linkage groups being phosphorodiester linkage groups, and p being a phosphate moiety at the 5' end. SYN51 is known as a sequence to be highly toxic in the mouse in the presence of PS bonds.

FIG. 2 shows that PT and aPTT profiles were very similar in mouse and human plasma. In both cases, tcDNAs with PO bonds (tcDNA-PO M23D as well as for tcDNA-PO SYN51 and palmitoyl conjugated-AON) did not trigger significant changes in prothrombin time (PT), while tcDNA with PS bonds increased PT, particularly the tcDNA-PS SYN51, which regularly triggered acute toxicity in the mouse after intravenous injection. In addition, tcDNA-PS AONs also strongly increased aPTT as well as the tcDNA-PO harboring the SYN51 sequence, particularly with human plasma (FIG. 2D). In view of the clinical signs triggered by the different AONs, it emerged that the PT test mirrored the amplitude of the acute adverse effects, at least in the mouse. All tcDNA-PO AONs were safe in the mouse and did not increase PT. On the other hand, the tcDNA-PS M23D only triggered a small increase of PT and was never noticed toxic while the tcDNA-PS SYN51 produced a strong increase of PT and was highly toxic.

Figure 8A:
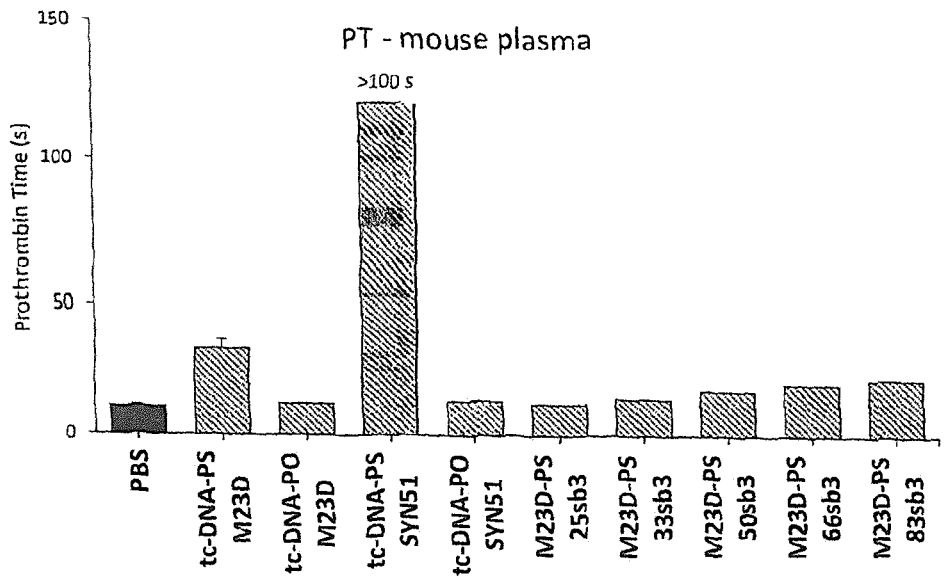
FIG. 8: The Prothrombin Time and the Partial Thromboplastin of following sequences bearing variable content of Sulphur in internucleosidic linkages: tcDNA-PO M23D (SY-0308, SEQ ID NO: 1) or tcDNA-PS M23D (SY-0210, SEQ ID NO: 23) or tcDNA-PS SYN51 (SEQ ID NO:19 with all nucleotides being tc-DNAs and all internucleosidic linkage groups being PS linkage groups) or tcDNA-PO SYN51 (SEQ ID NO: 19 with all nucleotides being tc-DNAs and all internucleosidic linkage groups being PO linkage groups), M23D-PS 25sb3 corresponds to (p-CCTCGGCTTA*C*C*T—SEQ ID NO:42); M23D-PS 33sb3 corresponds to (p-CCTCGGCTT*A*C*C*T—SEQ ID NO:43); M23D-PS 50sb3 corresponds to (p-CCTCGGC*T*T*A*C*C*T—SEQ ID NO:44); M23D-PS 66sb3 corresponds to (p-CCTCG*G*C*T*T*A*C*C*T—SEQ ID NO:45) and M23D-PS 83sb3 corresponds to (p-CCT*C*G*G*C*T*T*A*C*C*T—SEQ ID NO:46), where "*" between two nucleosides indicates phosphorothioate internucleosidic linkages and p represents a terminal phosphate group.
Figure 8B:
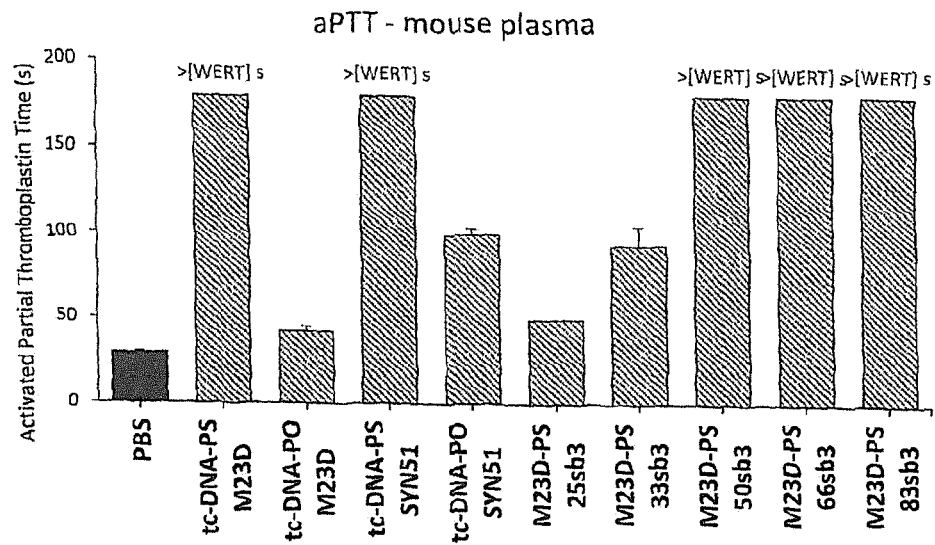

FIG. 8 shows that the PT and aPTT decreases proportionally with reduction of PS linkages in the backbone of an oligonucleotide. Here we used tc-DNA M23D sequence with variable amount of internucleosidic PS linkages, thus M23D-PS 25sb3 corresponds to (p-CCTCGGCTTA*C*C*T—SEQ ID NO:42); M23D-PS 33sb3 corresponds to (p-CCTCGG CTT*A*C*C*T—SEQ ID NO:43); M23D-PS 50sb3 corresponds to (p-CCTCGGC*T*T*A*C*C*T—SEQ ID NO:44); M23D-PS 66sb3 corresponds to (p-CCTCG*G*C*T*T*A*C*C*T—SEQ ID NO:45) and M23D-PS 83sb3 corresponds to (p-CCT*C*G*G*C*T*T*A*C*C*T—SEQ ID NO:46), where "*" between two nucleosides indicates phosphorothioate internucleosidic linkages and p represents a terminal phosphate group. As demonstrated previously, the aPTT test is more sensitive to PS content than the PT, and reaches its maximal measured time at six internucleosidic PS (compound M23D-PS 50sb3). Lower number of PS linkages induces only very limited increase in PT and aPTT.

Complement activation was also tested in the mouse after systemic injections of AONs at the high dose of 200 mg/kg.

Figure 3:
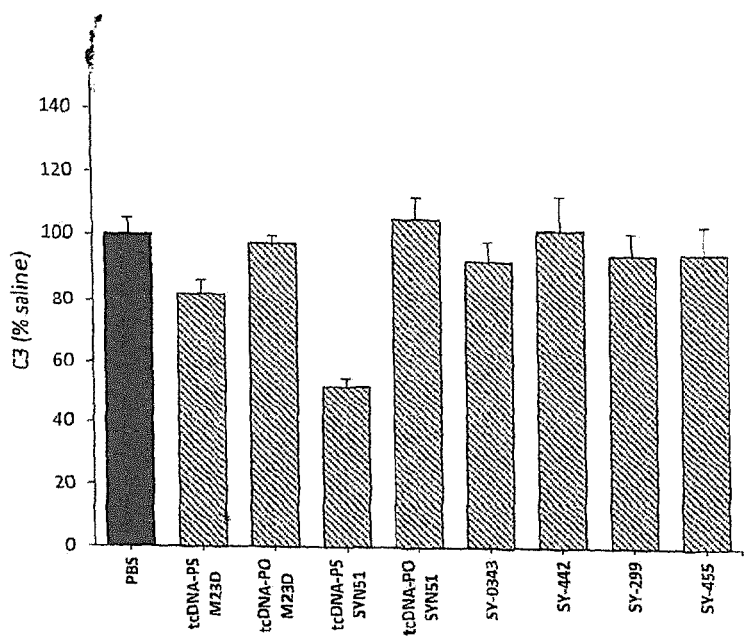
FIG. 3: One hour after the AON injection, blood samples were collected from all mice to measure complement C3. Complement activation in serum samples was determined by Microvue PanSpecific-C3 converter and SC5b-9 Plus kits (Quidel Co., San Diego CA, USA): Mouse C3 protein was converted to human SC5b9 using a C3 converter reagent (Pan specific C3 reagent kit, Microvue, Quidel) then detected by SC5b9 Elisa (Quidel). Complement activation was expressed as a percentage of lasting levels of C3 in samples considering levels of C3 in the PBS condition at 100% of C3 (no activation).
Figure 4A:
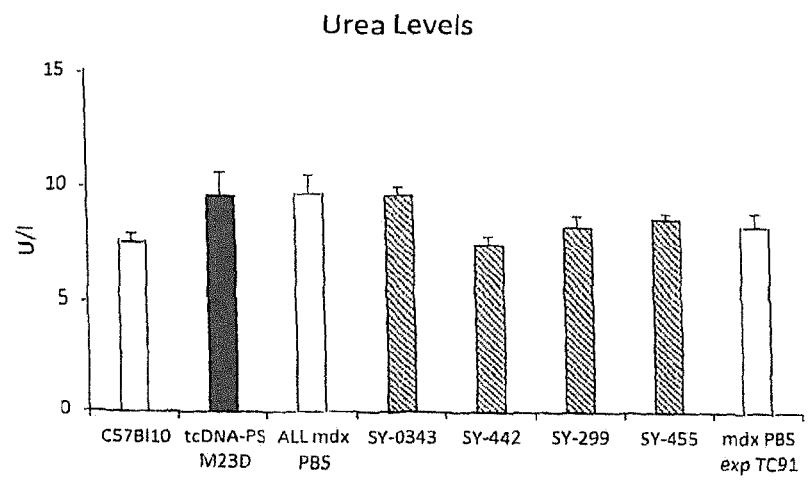
FIG. 4: Serum biochemistry analysis at the end of four week treatment. No significant changes in Serum albumin, creatinine and urea suggesting lack of kidney toxicity. Only slight elevation of ALP for most palmitoyl conjugated PO M23D have been observed.
Figure 4B:
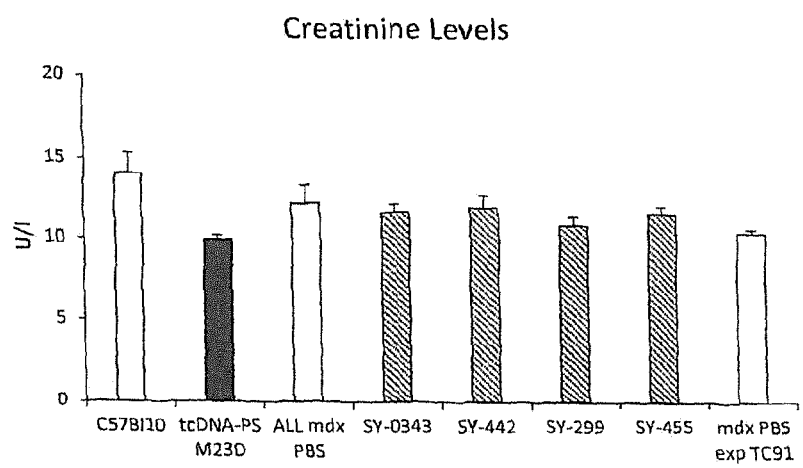
Figure 4C:
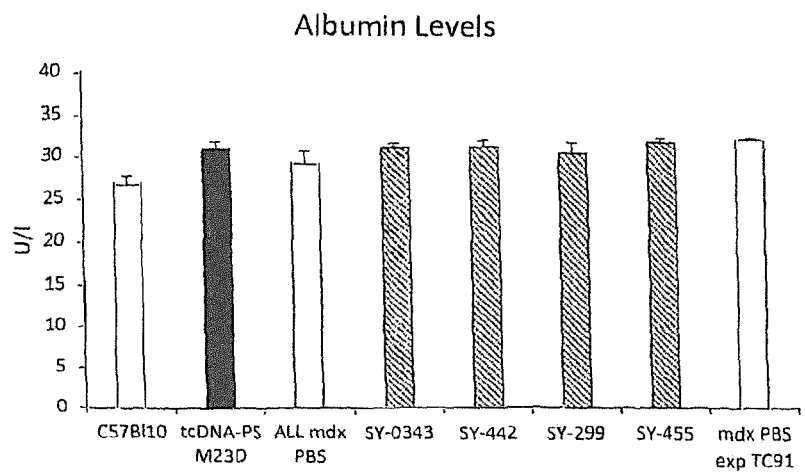
Figure 4D:
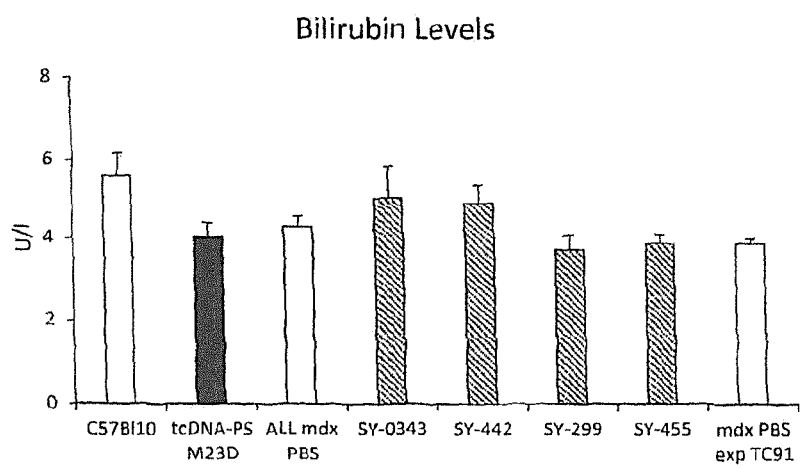
Figure 4E:
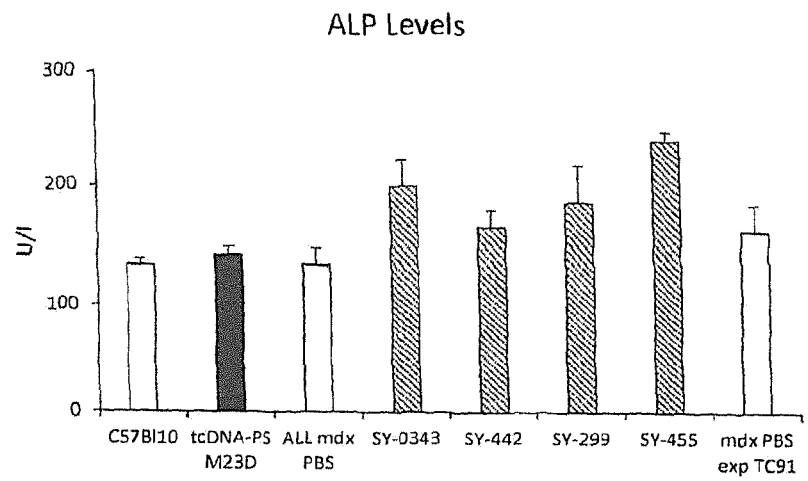
Figure 4F:
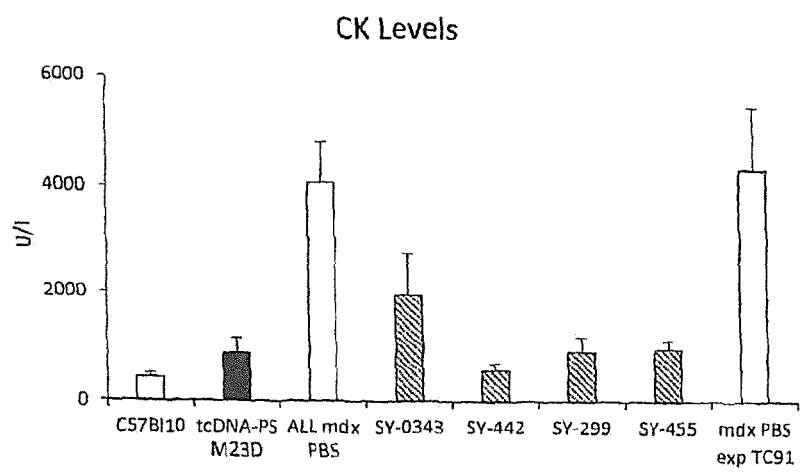
Figure 4G:
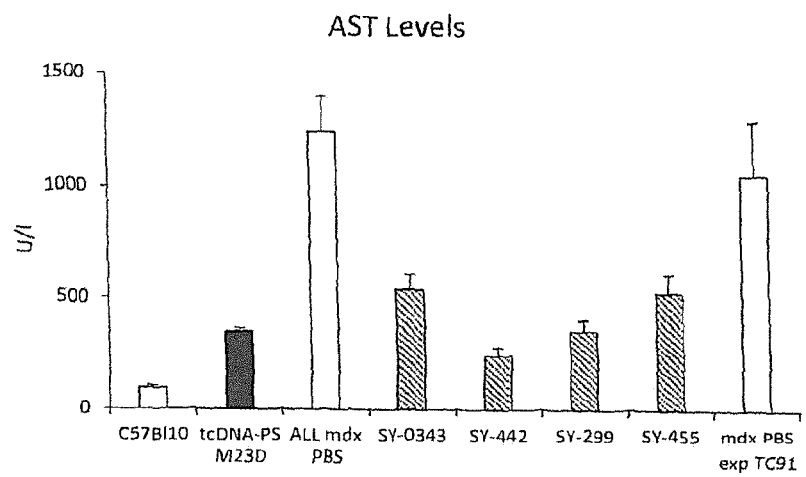
Figure 4H:
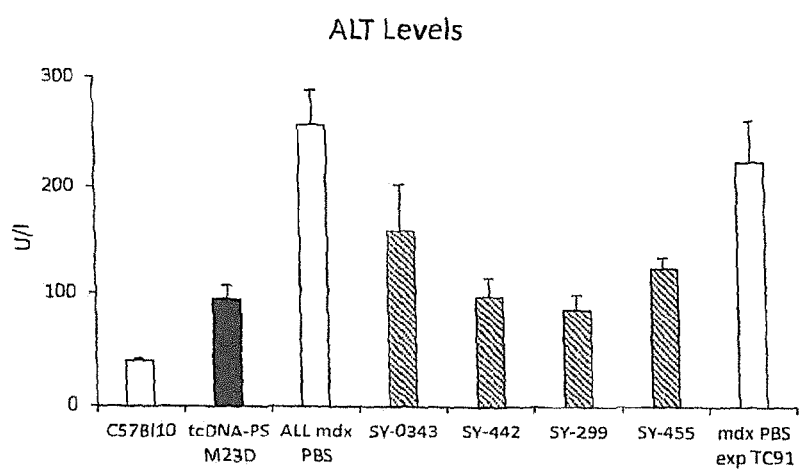

FIG. 3 shows that safe AONs comprising phosphorodiester linkage groups as internucleosidic linkage groups, specifically tcDNA-PO M23D, tc-DNA-PS M23D, tcDNA-PO SYN51 and the inventive palmitoyl conjugated-AON (SY-0299, SY-0343, SY-0442 and SY-0455) did not significantly activate the complement cascade. Only the toxic tcDNA-PS SYN51 clearly activated the cleavage of C3 (50%). Note that the tcDNA-PS M23D, which was regarded as safe, still activated a bit the C3 consumption.

Serum have been collected at the end of the 4 week treatment with compounds SY-0299, SY-0343, SY-0442 and SY-0455 and serum biochemistry was evaluated (FIG. 4). No significant changes in Serum albumin, creatinine and urea suggesting lack of kidney toxicity. Only slight elevation of ALP (FIG. 4E) for most palmitoyl conjugated PO M23D have been observed.

Thus, and as indicated, systemic delivery of the inventive compositions comprising the antisense oligomers linked with said 5'-palmitoyl-C6-amino lipid moiety and spacer and having a full PO backbone (Palmitoyl conjugated PO M23D, SY-0343) allowed greater rescue of dystrophin, compared to equivalent sequences made of tcDNA with either PO or PS backbones. Furthermore, said inventive compositions (SY-0299, SY-0343, SY-0442 and SY-0455) and AON, respectively, does not trigger deleterious outcomes in the blood compartment after systemic delivery. Moreover, the lack of sulfur in the phosphate backbone of the AON significantly reduced the non-specific binding of serum proteins and thus the risks of complement activation and/or coagulation adverse effects. The inventive compositions comprising at least one lipid moiety, such as the palmitoyl conjugated-tcDNA AONs with internucleosidic linkage groups being PO, conferred new properties onto PO-tcDNA containing molecules, which are believed to now bind preferentially serum proteins such as albumin and lipoproteins, which are natural carriers for molecules of low water solubility including fatty acids. Furthermore and summarizing the results presented above point out that tcDNA AONs that modify the coagulation properties also systemically activate the complement cascade in vivo. A significant increase of the PTT value (>180 s) is a sign of a potential risk, which becomes real when the PT value is also drastically increased (>100 s). Finally, tcDNA-PO and the inventive compositions Palm-tcDNA-PO are much safer than their related tcDNA-PS.

Example 2

Co-Precipitation Experiments and Proteomics

Oligonucleotides of interest were synthesized as biotinylated conjugates for subsequent co-precipitation of potentially interacting serum proteins by using streptavidin-beads. The biotinylated derivatives used in this study are SY-0440, SY-0427, SY-0446, SY-0448, SY-0445, SY-0443, and SY-0451, which are defined and characterized in Table 3 and shown in FIG. 6.

Biotinylated oligonucleotides, immobilized on streptavidin-beads, were incubated in the presence of serum for 1 h. Beads were collected by low speed centrifugation, washed and then solubilised in the appropriate buffer for further protein analysis by SDS-PAGE, Orbitrap LC-MS/MS and SDS-PAGE/MALDI-TOF.

Figure 7:
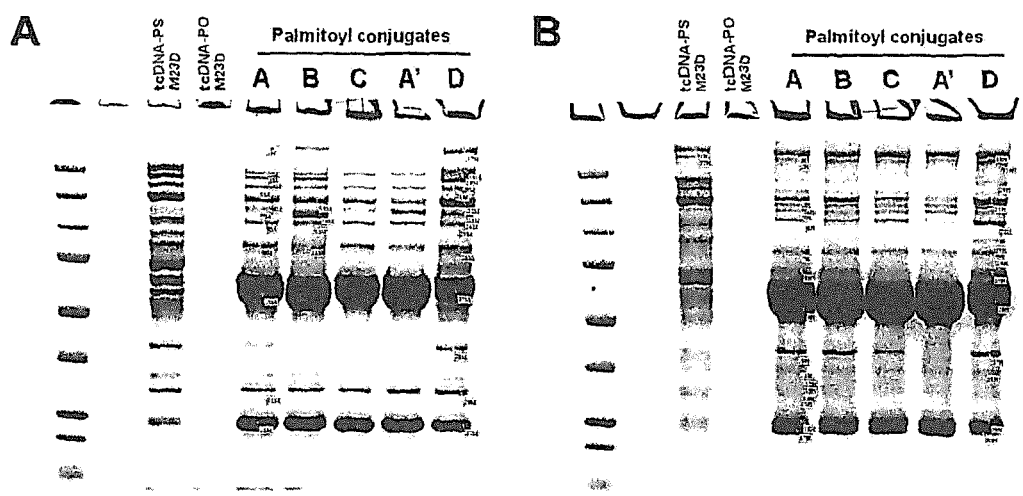
FIG. 7: SDS-PAGE analysis of protein recovery from mouse (FIG. A) and human (FIG. B) sera using the oligonucleotides listed and depicted in FIG. 6. Twenty μg of immobilized-AOs were incubated in 50 μL of 10 times diluted serum.

FIG. 7 exemplifies SDS-PAGE analysis of protein recovery from mouse and human sera for the oligonucleotides used in this study. It appears that SY-0440, i.e. the tcDNA M23D with full-PS retained far more serum proteins than its tcDNA-PO equivalent, SY-0427. This result is consistent with previous studies (not shown) using various sequences (M23D, SYN51, and Poly T) and backbone chemistries (DNA, tcDNA, 2'OMe-PS and PMO) demonstrating that oligomers lacking PS bonds did not significantly bind serum proteins suggesting that protein absorption preferentially occurred at the level of the thiophosphate backbone and did not involve consensus sequence motifs.

In general terms, we found that tcDNA-PS oligonucleotides bound many proteins related to the complement pathways and coagulation. Orbitrap analysis revealed that tcDNA-PS oligonucleotides retained mannose-binding proteins (MBL) that are instrumental in innate immunity via the lectin pathway. MBLs are bound to MASPs (MBL-associated serine protease—MASP-1; -2; -3), which also form complexes with ficolins. When MBL binds to its target (for example, mannose on the surface), the MASP protein functions to cleave the blood protein C4 into C4a and C4b. The C4b fragments can then bind to the surface, and initiate the formation of a C3-convertase. MBL/MASP-1 complex also has thrombin-like activity (thrombin clots fibrin to initiate blood clots). All these proteins were found in tcDNA-PS samples, but not in complexes with oligonucleotides lacking PS internucleotide linkages.

As shown in FIG. 7, the inventive tcDNA-palmitoyl conjugates displayed comparable patterns of protein recovery, which were very different of those obtained with naked tcDNA-PS and tcDNA-PO. In view of the fact that tcDNA-POs were consistently not significantly binding serum proteins, it was likely that resulting patterns for A, B, C, A' and D molecules were contributed by large by their palmitoyl and alkylphosphate moiety. SDS-PAGE MALDI-ToF NmS analysis of the main proteins recovered from mouse and human sera showed that predominant proteins were albumin and lipoprotein components of the LDL (low-density lipoproteins) and HDL (high density lipoproteins) complexes, all involved in the transport of lipids (Table 4 and Table 5).

TABLE 4

Proteins recovered from mouse serum using the different biotinylated palmitoyl-tcDNA compositions (FIG. 7A).

| Number | Score | Name | Abundance |
|---|---|---|---|
| 1-17 | 370 | Apolipoprotein B-100 | |
| 2-18-19 | 697 | Fibronectin | |
| 3 | 386 | Apolipoprotein B-100 | |
| 4 | 355 | Inter-alpha-trypsin inhibitor heavy chain H2 | |
| 5 | 18 | Tumor necrosis factor receptor superfamily member 26 | |
| 6-13-22 | 42 | Thrombospondin-1 | Variable |
| 7-14-23 | 580 | Serum albumin | |
| 8-15-25 | 498 | Phosphatidylinositol-glycan-specific phospholipase D | |
| 9-26 | 676 | Antithrombin-III | |
| 10-27 | 1020 | Serum albumin | Very high |
| 11-29 | 40 | Apolipoprotein E | High |
| 12-30 | 701 | Apolipoprotein A-I | Very high |
| 16 | 28 | Prothrombin | |
| 20 | 404 | Inter-alpha-trypsin inhibitor heavy chain H1 | |
| 21 | 491 | Murinoglobulin-1 | |
| 24 | 476 | Inter alpha-trypsin inhibitor, heavy chain 4 | |
| 28 | 581 | Complement C3 | Variable |

TABLE 5

Proteins recovered from human serum using the different biotinylated palmitoyl-tcDNA compositions (FIG. 7B).

| Number | Score | Name | Abundance |
|---|---|---|---|
| 1-18-31 | 549 | Apolipoprotein B-100 | Medium |
| 2-19-32 | 831 | Apolipoprotein B-100 | |
| 3-21 | 258 | Complement factor H | Variable |
| 4 | 309 | Serum albumin | |
| 5 | 480 | Serum albumin | |
| 6-22 | 786 | Complement C3 | Variable |
| 7-24 | 762 | Antithrombin-III | |
| 8-25 | 464 | Complement C3 | Variable |
| 9-26 | 825 | Serum albumin | Very high |
| 10-27 | 456 | Complement C3 | Variable |
| 11-28 | 345 | Complement C3 | |
| 12 | 614 | Apolipoprotein E | |
| 13 | 597 | Apolipoprotein E | |
| 14 | 156 | Serum albumin | |
| 15 | 160 | Keratin, type II cytoskeletal 2 epidermal | |
| 16-29 | 647 | Apolipoprotein A-I | Very high |
| 17-30 | 730 | Apolipoprotein A-I | Very high |
| 20 | 383 | Inter-alpha-trypsin inhibitor heavy chain H1 | |
| 23 | 423 | Keratin, type I cytoskeletal 16 | Medium |

Apparently, the C7 moiety at the 3' end of the tcDNA sequence did not significantly contribute to the binding of serum proteins (compare A (SY-0446) to B (SY-0445)) although B retained more dimeric forms of albumin in the mouse. Comparison of B and C (SY-0443) shows that the presence of a thiophosphate at both ends of the tcDNA sequence did not enhance protein binding; quite the reverse, there is a slight decrease for some proteins in human serum (factor H and a fragment of Complement C3). The A' (SY-0448) molecule was similar to A, except in A' the third nucleotide of the sequence was replaced by a 2'OMe-U. A/A' profiles were almost identical in the mouse condition, but showed a few differences in human serum; particularly, A' retained less factor H and Complement C3, suggestive of a possibly better safety profile. Finally, the D molecule (SY-0451), lacking both C7 and C6 retained slightly less albumin and HDL components compared to A and A', hence leaving room to further proteins as shown by the increase in intensity of previously marginal bands.

The C7 motif was initially introduced to allow the grafting of a ligand for further tissue specific targeting. Although our study showed that the C7 moiety had no effect on the retention of serum proteins, it still may be advantageous to maintain it at the 3' end of the AON to enlarge the size of the compound and thus improve the steric hindrance at the level of its pre-mRNA target. On the other side of the compound, it appears that spacing the palmitoyl moiety from the 5' end of the tcDNA sequence with C6 increases preferential binding of albumin and lipoprotein complexes involved in fatty acid transport.

Example 3

Stability of Inventive Compositions in Human Serum

The stability of preferred inventive compositions in human serum was studied on oligonucleotides SY-0343, SY-0442, SY-0299, SY-0450, SY-0455 and SY-0357. The inventive compositions are defined and characterized in Table 3.

A mixture (total volume 80 μL) composed of human serum 40 μL, oligonucleotide stock solution, 20 μL of PBS (2×) and milliQ water was prepared in 0.2 mL PCR vial, so that the final concentration of the oligonucleotide was 2 μM and incubated at 37° C. Aliquots were withdrawn after 4, 24, and 120 h. The mixture was digested in the PCR vial with proteinase K (80 μL of mixture, 100 μL of proteinase K buffer 2× (200 mM Tris-HCl, pH 8.5, 400 mM NaCl, 10 mM EDTA, 0.4% SDS), 20 μL proteinase K (20 mg/mL in 100 mM Tris-HCl pH 8.5, 10 mM $CaCl_2$) at 55° C. for 2 h. The mixture was then cooled to room temperature, centrifuged (13400 rpm, 10 min) and the supernatant was collected. An aliquot of 50 μL was then taken for SPE and diluted with 50 μL of the 0.2 M TEAB buffer. After 30 min, 50 μL of the Condi-solution (15 mM $Et_3N$, 100 mM HFIP) was added. The SPE columns (Oasis HLB 1 cc (10 mg) Extraction Cartridges, Waters 186000383) were conditioned by successive passing of 1 mL of MeOH and 2×500 μL of the Condi-solution. The test solution from above was quantitatively applied on the SPE column, the column was washed successively by passing of 2×250 μL of Condi-solution and 300 μL of TEAB (0.2 M) solution. The oligonucleotide is washed out by application of 2×200 μL of Elution-solution (Condi-solution/MeOH 4:6) and 150 μL of MeOH and eluates are collected. The eluate was lyophilised in a speedvac to dryness and afterwards diluted with 100 μL of milliQ water. The mixture was then analyzed by HPLC-DAD-MS (Waters Acquity OST C18, 100×2.1 mm, 1.7 μm, Mobile phase A: 400 mM HFIP, 15 mM TEA+10% methanol, Mobile phase B: Methanol, flow 0.2 mL/min, 70° C.).

As described in Table 6 and Table 7, the main degradation product after the incubation in human serum was for all tested sequences the parent oligonucleotide as depicted in the following:

No other degradation products were detected in significant amounts. Especially, no cleavage between tc- and 2'-OMe nucleosides (sequence SY-0455) and no cleavage of the C7-amino group at the 3'-end (sequences SY-0343, SY-0299, SY-0357) were observed after 120 h. The sequences with PO linkage between oligonucleotide and spacer/lipid moiety were considerably less stable in human serum as compared to their PS counterparts. After 24 h, a substantial amount of the spacer/lipid moiety was cleaved and almost no original oligonucleotide was present after 120 h in sequences linked via PO, whereas only about 1 and 8% of spacer/lipid moiety was cleaved in case of fatty acid connected via PS linker after 24 and 120 h, respectively.

TABLE 6

Stability of inventive TcDNA-palmitoyl compositions in human serum ($1^{st}$ experiment)

| $1^{st}$ experiment | Original product left [%] | | | Ratio oligo without linker [%] | | |
|---|---|---|---|---|---|---|
| Time [h] | 4 | 24 | 120 | 4 | 24 | 120 |
| SY-0343 | 99 | 105 | 87 | n.d. | n.d. | 7 |
| SY-0442 | 102 | 100 | 77 | n.d. | n.d. | 9 |
| SY-0299 | 99 | 63 | 0 | n.d. | n.d. | 100 |
| SY-0455 | 87 | 0 | 0 | n.d. | n.d. | 100 |
| SY-0357 | 65 | 33 | 0 | n.d. | n.d. | 100 |

TABLE 7

Stability of inventive TcDNA-palmitoyl compositions in human serum ($2^{nd}$ experiment)

| $2^{nd}$ experiment | Original product left [%] | | | Ratio oligo without linker [%] | | |
|---|---|---|---|---|---|---|
| Time [h] | 4 | 24 | 120 | 4 | 24 | 120 |
| SY-0343* | 63 | 75 | 46 | <1 | 1 | 8 |
| SY-0442 | 84 | 93 | 81 | <1 | 1 | 8 |
| SY-0299 | 96 | 62 | 15 | 8 | 41 | 68 |
| SY-0450 | 102 | 72 | 32 | 7 | 33 | 72 |
| SY-0455 | 94 | 34 | 4 | 17 | 66 | 95 |
| SY-0357 | 53 | 0 | 0 | 39 | 100 | 100 |

*difficult to integrate due serum signals

Example 4

Identification of Multimers

Polyacrylamide-gel electrophoresis (PAGE) experiments were performed to detect self-multimers. The following chemicals were used: tris(hydroxymethyl)aminomethane (Tris), (TCI A0321); acetic acid (Merck 1.00063); acrylamide/Bis solution, 29:1 (40%, Serva 10680.01); tetramethylethylenediamine; TEMED, Sigma-Aldrich T9281); ammonium persulfate (Sigma-Aldrich 248614); and glycerol (Sigma-Aldrich G9012). Buffer solution A was prepared by dissolving 60 g of Tris in 200 mL of water. The pH is

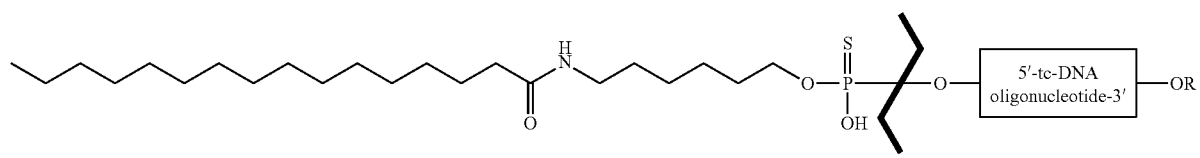

adjusted to 7.4 with glacial acetic acid (about 25-30 mL). The solution is diluted to 500 mL with water and stored at +4° C. Buffer solution B was prepared by diluting 16 mL of buffer solution A to 800 mL with water. Ammonium persulfate 10% (w/v) was prepared by dissolving 100 mg of ammonium persulfate are dissolved in 0.9 mL of water. The preparation of gel was performed by mixing the following solutions in a glass beaker: 9.4 mL acrylamide/bis solution; 15 mL water; 500 µL of buffer solution A; 125 µL of ammonium persulfate 10% (w/v), and 38 µL of TEMED. The test solution was 2 mg/mL in 50% glycerol, and 10 µL was applied (equal to 10 µg of oligonucleotide). The pre-migration settings were 40 min/90 V with buffer solution B. The migration settings were 90 min/90 V or 15 min/90 V plus 45-60 min/120 V with buffer solution B. 5-7 µL of 6×DNA loading dye was also migrated. Detection was performed by placing the gel on a TLC plate and examining under UV light at 254 nm. Afterwards, staining with Stains-All (Sigma-Aldrich, 1-Ethyl-2-[3-(1-ethylnaphtho[1,2-d]thiazolin-2-ylidene)-2-methylpropenyl]naphtho[1,2-d]thiazolium bromide, 3,3'-diethyl-9-methyl-4,5,4',5'-dibenzothiacarbocyanine) according to the manufacturer's protocol was performed.

Figure 9:
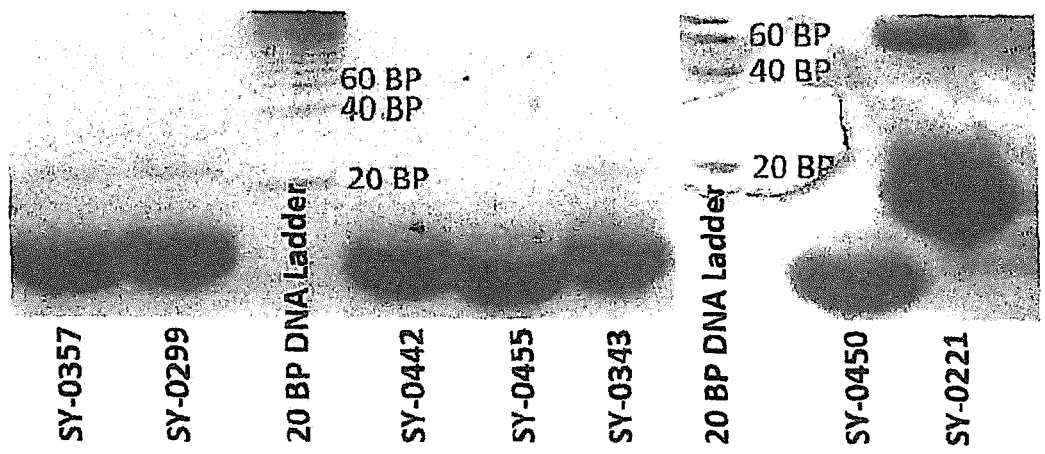
FIG. 9: non-denaturing PAGE of oligonucleotides SY-0357, SY-0299, SY-0442, SY-0455, SY-0343 and SY-0450. The oligonucleotide SY-0221 (CTT TCA TAA TGC TGG—SEQ ID NO:47) with full PS backbone that was toxic in mouse is used to demonstrate the migration of multimer band on the gel (visualization with StainsAll).

As noted previously, it was observed that tc-DNA oligonucleotides with acute toxicity show an additional band in polyacrylamide gel electrophoresis experiments migrating at the level of 40-60 BP. It was proposed that this rather sharp band is a multimer of the oligonucleotide (e.g., duplex, trimer, or larger aggregate). The results of gel electrophoresis experiments are shown in FIG. 9 with no apparent appearance of the multimer band for any of oligonucleotides studied. For illustration of multimer band, the oligonucleotide SY-0221, which showed toxicity in vivo is also shown.

Example 5

Exon 23 Skipping Studies Performed with Mouse M23D Surrogate Sequence

SY0442 and SY0450 were selected for further investigation on efficacy of exon 23 skipping. SY0210 (Full PS) and SY0308 (Full PO) were used as controls for some of the experiments detailed herein. The objective of these experiments is to test the efficacy and tcDNA content in tissues and to determine the potential toxicity of the test compounds.

Mdx23 mice were injected with compound at 50 mg/kg/wk or 200 mg/kg/wk for 4 weeks. Group 1 was analyzed 72 hours after the last injection while group 2 was analyzed 2 weeks after the last injection. The in vitro and mouse model studies discussed in Examples 1 and 2 were performed and the results were consistent with those Examples.

Figures 10A, 10B:
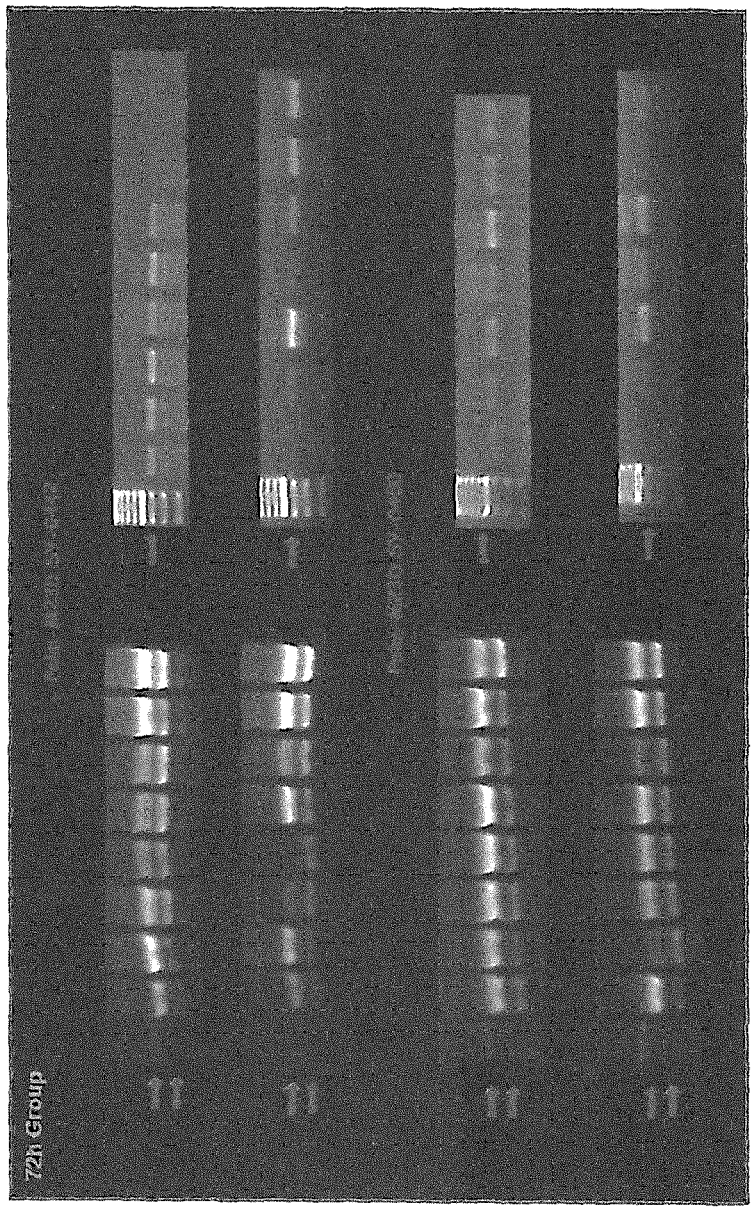
FIG. 10: Exon 23 skipping detected by nesting RT-PCR in various tissues from mice treated with 200 mg/kg for 72 hours of SY442 (FIG. 10A) or SY450 (FIG. 10B) and for 2 weeks with SY442 (FIG. 10C) or SY450 (FIG. 10D). The left panels represent RT-PCR between exons 20 and 26 showing the unskipped product at 901 bp and the skipped product at 688 bp. The right panels represent specific RT-PCR between exons 20 and junction 22-24 showing exclusively the skipped product at 401 bp. The specific PCR shown in the right panels was used only where the skipping levels were too low to be detected by classical RT-PCR.
Figures 10C, 10D:
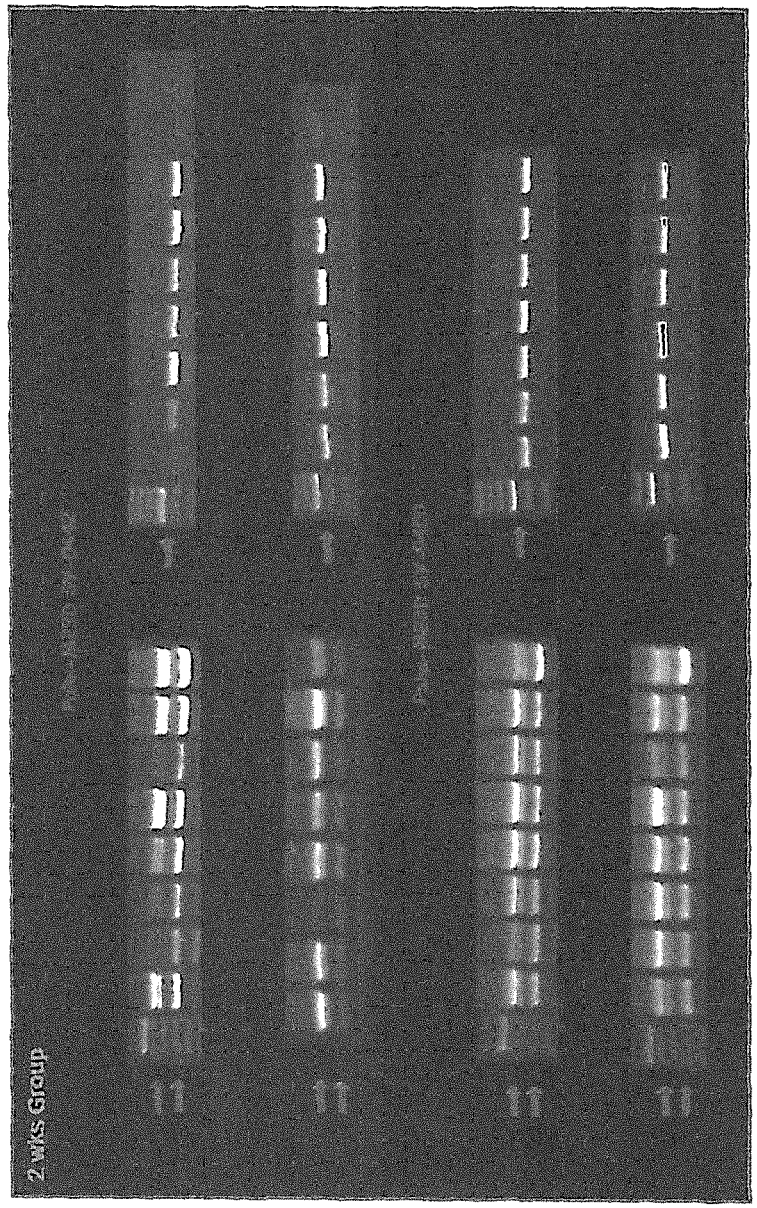
Figures 11A, 11B, 11C:
FIG. 11: Exon 23 skipping detected by nesting RT-PCR in various tissues from mice treated with 50 mg/kg for 72 hours of SY442 (FIG. 11A) or SY450 (FIG. 11B) with SY0210 as a control (FIG. 11C) and for 2 weeks with SY442 (FIG. 11D) or SY450 (FIG. 11E) with SY0210 as a control (FIG. 11F). The left panels represent RT-PCR between exons 20 and 26 showing the unskipped product at 901 bp and the skipped product at 688 bp. The right panels represent specific RT-PCR between exons 20 and junction 22-24 showing exclusively the skipped product at 401 bp. The specific PCR shown in the right panels was used only where the skipping levels were too low to be detected by classical RT-PCR.
Figures 11D, 11E, 11F:
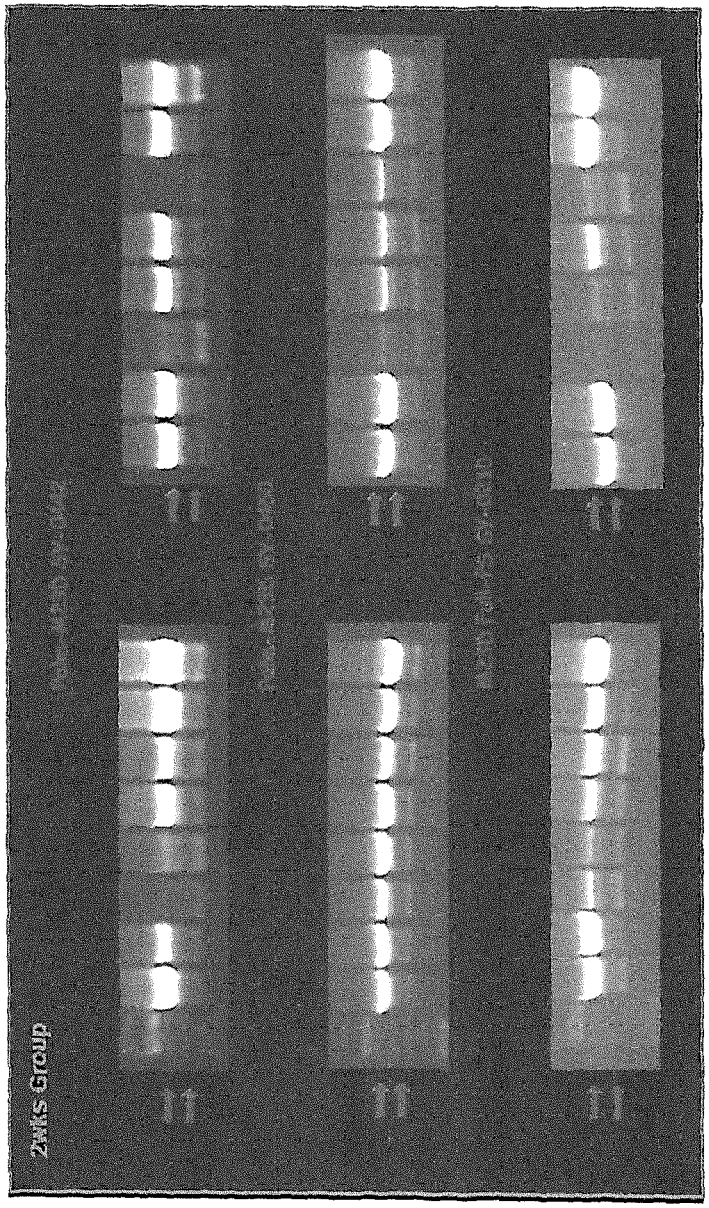

Exon 23 skipping levels were evaluated using nested RT-PCR. Total RNA was extracted from certain tissues in the mouse model and reverse transcribed using the SSIII cDNA Synthesis Kit. RT-PCR was performed between exons 20 and 26 and a specific RT-PCR was also performed detecting exclusively the skipped product. FIGS. 10A-D demonstrate the results of the RT-PCR for 200 mg/kg/wk at 72 hours (FIGS. 10A and 10B) and at 2 weeks (FIGS. 10C and 10D). A significant band can be observed corresponding to the exon 23 skipped product in all muscles treated with the compounds. Skipping levels appear particularly high in the heart in all cases. Using the specific nested PCR, exon 23 skipping was also detected in CNS, smooth muscle of the GI tract, and the retina. Similar results were obtained for the 50 mg/kg/wk cohorts (FIG. 11).

Figure 12:
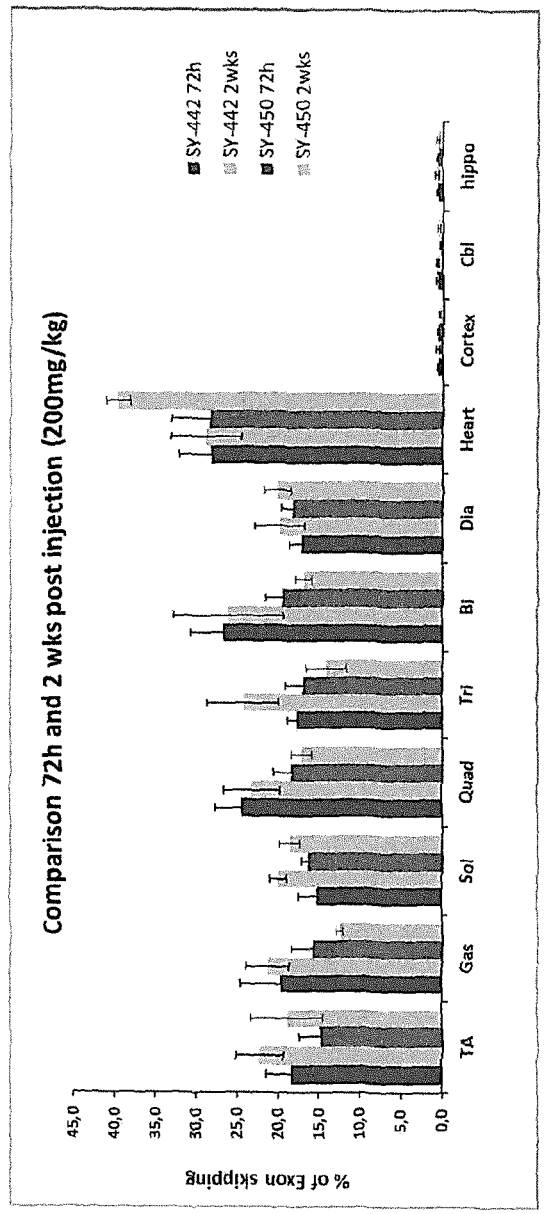
FIG. 12: Exon 23 skipping quantification by taqman qPCR in tissues from mice treated with 200 mg/kg of tcDNA at 72 hours and 2 weeks post injection.
Figure 13:
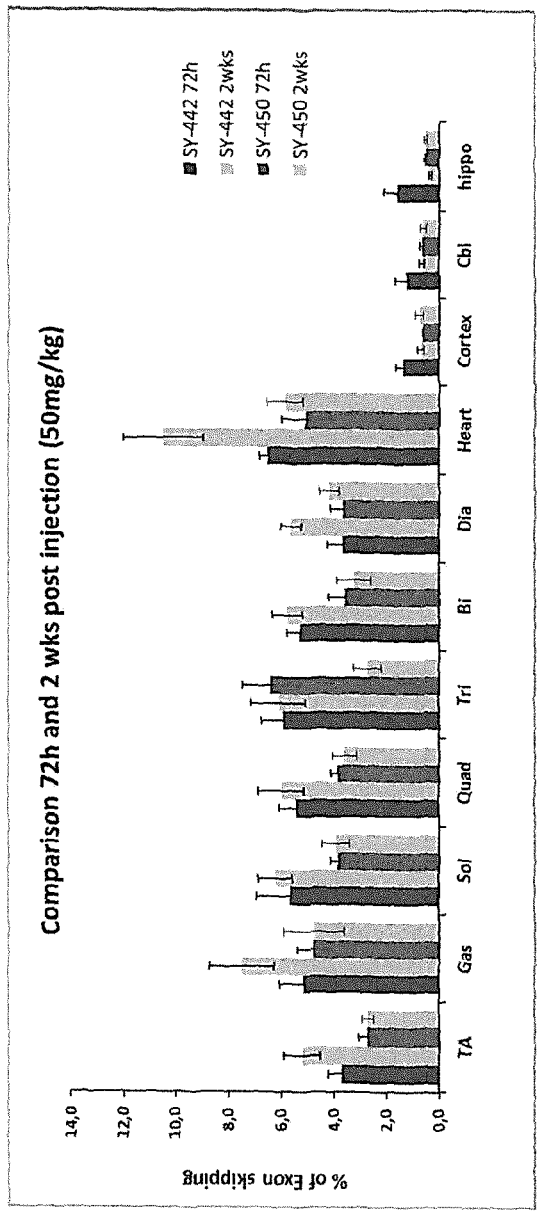
FIG. 13: Exon 23 skipping quantification by taqman qPCR in tissues from mice treated with 50 mg/kg of tcDNA at 72 hours and 2 weeks post injection.

Exon 23 skipping was further more precisely quantified using a more sensitive taqman qPCR protocol. FIGS. 12A and 12B demonstrate the similar results across the 200 mg/kg (FIG. 12A) and the 50 mg/kg (FIG. 12B) cohorts. The ratios calculated between the 72 hour and 2 week cohorts were close to 1 in most cases for each of SY0442 and SY0450 at each dose:

| | TA | Gas | Soleus | Quad | Tri | Bi | Dia | Heart |
|---|---|---|---|---|---|---|---|---|
| SY0442, 200 mg, 72 hr/2 wk | 0.82 | 0.93 | 0.76 | 1.06 | 0.73 | 1.09 | 0.87 | 0.98 |
| SY0442, 50 mg, 72 hr/2 wk | 0.71 | 0.69 | 0.91 | 0.91 | 0.98 | 0.91 | 0.65 | 0.62 |
| SY0450, 200 mg, 72 hr/2 wk | 0.79 | 1.27 | 0.88 | 1.07 | 1.20 | 1.17 | 0.90 | 0.72 |
| SY0450, 50 mg, 72 hr/2 wk | 1.00 | 1.00 | 0.98 | 1.07 | 2.36 | 1.11 | 0.87 | 0.87 |

Ratios of exon skipping were also calculated between SY0442 and SY0450, which demonstrated that SY0442 generally had a slightly higher overall level of skipping than SY0450:

| | TA | Gas | Soleus | Quad | Tri | Bi | Dia | Heart |
|---|---|---|---|---|---|---|---|---|
| SY0442/ SY0450, 200 mg | 1.20 | 1.44 | 1.05 | 1.34 | 1.35 | 1.45 | 0.95 | 0.84 |
| SY0442/ SY0450, 50 mg | 1.63 | 1.32 | 1.52 | 1.53 | 1.32 | 1.62 | 1.19 | 1.55 |

Figure 14:
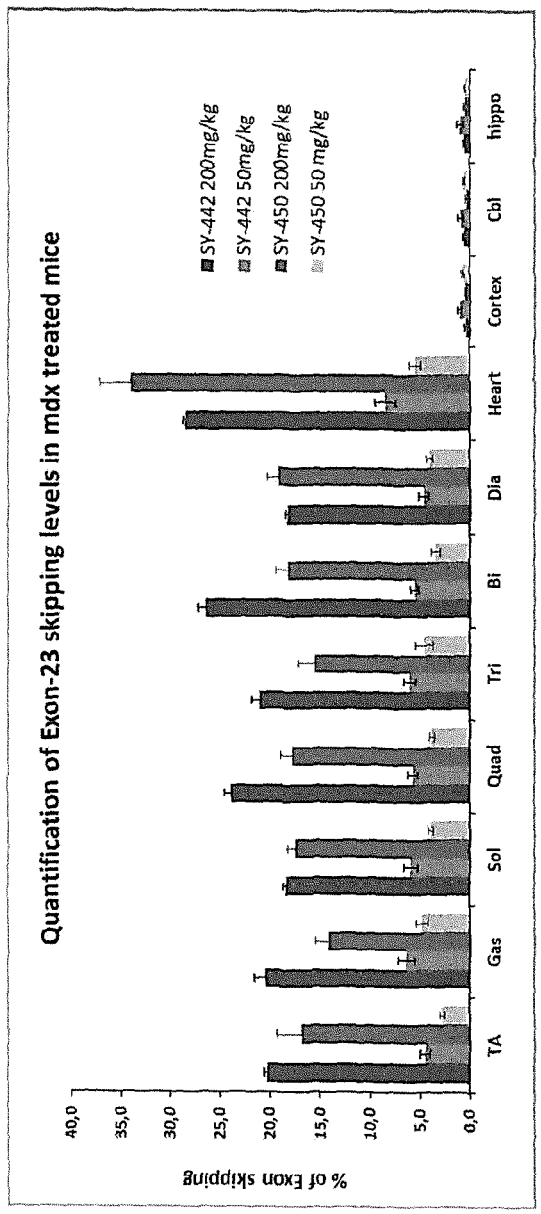
FIG. 14: Pooled data comparing SY0442 and SY0450 efficacy at 72 hours and 2 weeks post injection. A dose effect can be observed between 50 mg/kg and 200 mg/kg (approximately 4-fold).
Figure 15:
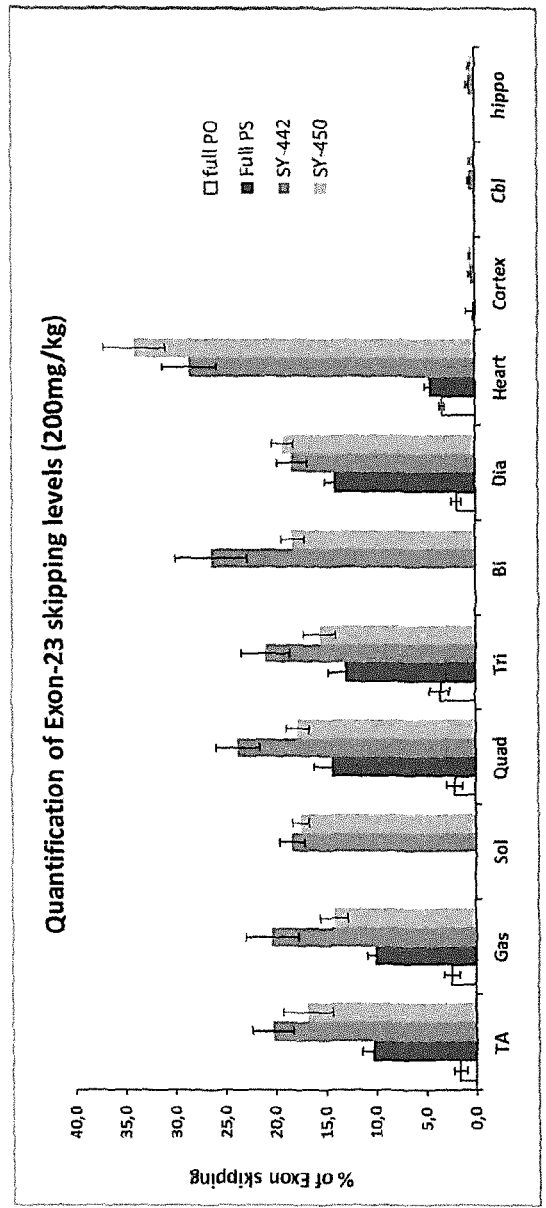
FIG. 15: Quantification of exon 23 skipping at 200 mg/kg as compared with Full PO and Full PS compounds.
Figure 16:
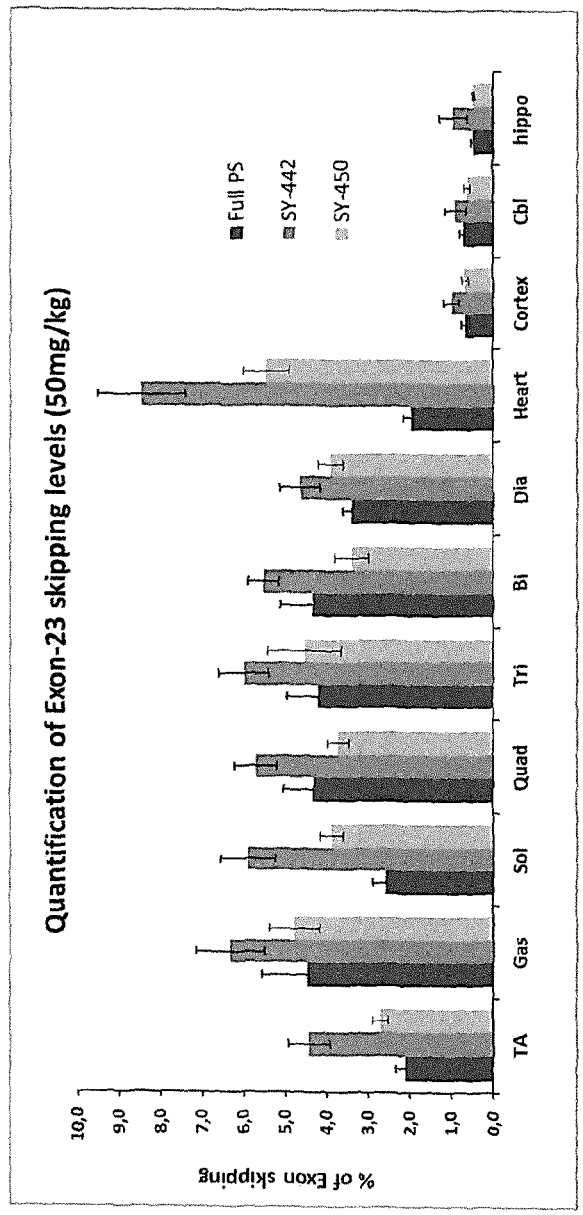
FIG. 16: Quantification of exon 23 skipping at 50 mg/kg as compared with Full PO and Full PS compounds.

Data was further manipulated in FIG. 14 to show pooled data comparing SY0442 and SY0450 efficacy at 72 hours and 2 weeks postinjection. A dose effect can be observed between 50 mg/kg and 200 mg/kg (approximately 4-fold). Quantification of exon 23 skipping at 200 mg/kg (FIG. 15) and at 50 mg/kg (FIG. 16) as compared with Full PO and Full PS compounds was also measured.

In order to identify the most potent compound, the ratio of efficacy/quantity of compound found in tissues was calculated for 200 mg/kg:

| | TA | Gas | Soleus | Quad | Tri | Bi | Dia | Heart |
|---|---|---|---|---|---|---|---|---|
| SY0442, 200 mg/kg, 72 hr | 0.45 | 0.27 | 0.63 | 0.43 | 0.32 | 0.68 | 0.41 | 0.43 |
| SY0450, 200 mg/kg, 72 hr | 0.61 | 0.47 | 0.76 | 0.79 | 0.68 | 0.35 | 0.70 | 0.88 |
| SY0442, 200 mg/kg, 2 wk | 1.53 | 0.87 | 0.77 | 1.40 | 1.06 | 0.64 | 1.25 | 0.93 |
| SY0450, 200 mg/kg, 2 wk | 3.32 | 0.73 | 2.65 | 2.98 | 1.28 | 1.12 | 1.89 | 3.11 |

| | TA | Gas | Soleus | Quad | Tri | Bi | Dia | Heart |
|---|---|---|---|---|---|---|---|---|
| SY0442, 50 mg/kg, 72 hr | 0.78 | 0.94 | 0.51 | 0.91 | 0.85 | 0.51 | 0.41 | 0.54 |

|  | TA | Gas | Soleus | Quad | Tri | Bi | Dia | Heart |
|---|---|---|---|---|---|---|---|---|
| SY0450, 50 mg/kg, 72 hr | 1.56 | 1.91 | 1.65 | 1.93 | 1.70 | 0.90 | 1.46 | 1.56 |
| SY0442, 50 mg/kg, 2 wk | 3.47 | 2.00 | 1.55 | 2.39 | 2.21 | 1.28 | 2.50 | 1.40 |
| SY0450, 50 mg/kg, 2 wk | * | * | * | * | * | * | * | * |

* Because of low detection or below threshold of the quantity in the tissues, SY0450 at 2 weeks, accurate calculations could not be obtained.

Overall, the ratio data indicates more SY0442 in tissues than SY0450 at both doses, while efficacy for SY0442 is only slightly higher. Based on this data collected in this set of experiments, SY0450 appears to be a more efficacious and safe compound as compared with SY0450; however, at lower dose treatments, the SY0442 may be preferable due to the rapid cleavage of SY0450.

SEQUENCE LISTING

```
<160> NUMBER OF SEQ ID NOS: 47

<210> SEQ ID NO 1
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: modified_base
<222> LOCATION: (1)..(2)
<223> OTHER INFORMATION: m5c
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (11)..(12)
<223> OTHER INFORMATION: m5c

<400> SEQUENCE: 1
cctcggctta cct                                                        13

<210> SEQ ID NO 2
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (5)..(5)
<223> OTHER INFORMATION: m5c
```

-continued

```
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (12)..(13)
<223> OTHER INFORMATION: m5c

<400> SEQUENCE: 2
acctcggctt acc                                                          13

<210> SEQ ID NO 3
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(2)
<223> OTHER INFORMATION: deoxyribonucleoside with tricyclic sugar
<220> FEATURE:
<221> NAME/KEY: modified_base
<222> LOCATION: (1)..(2)
<223> OTHER INFORMATION: m5c
<220> FEATURE:
<221> NAME/KEY: misc_feature
<222> LOCATION: (3)..(3)
<223> OTHER INFORMATION: 2'-modified ribonucleoside, preferably
     2'-O-methyl ribonucleoside
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (4)..(13)
<223> OTHER INFORMATION: deoxyribonucleoside with tricyclic sugar
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (11)..(12)
<223> OTHER INFORMATION: m5c

<400> SEQUENCE: 3
ccucggctta cct                                                          13

<210> SEQ ID NO 4
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (5)..(5)
<223> OTHER INFORMATION: 2'-modified ribonucleoside, preferably
     2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
```

```
<221> NAME/KEY: modified_base
<222> LOCATION: (13)..(13)
<223> OTHER INFORMATION: m5c

<400> SEQUENCE: 4
aagauggcat ttcta                                                    15

<210> SEQ ID NO 5
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(7)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (4)..(5)
<223> OTHER INFORMATION: m5c
<220> FEATURE:
<221> NAME/KEY: misc_feature
<222> LOCATION: (8)..(8)
<223> OTHER INFORMATION: 2'-modified ribonucleoside, preferably
      2'-O-methyl ribonucleoside
<220> FEATURE:
<221> NAME/KEY: misc_feature
<222> LOCATION: (9)..(15)
<223> OTHER INFORMATION: deoxyribonucleoside with tricyclic sugar
<220> FEATURE:
<221> NAME/KEY: modified_base
<222> LOCATION: (13)..(14)
<223> OTHER INFORMATION: m5c

<400> SEQUENCE: 5
catcctggag ttcct                                                    15

<210> SEQ ID NO 6
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: deoxyribonucleoside with tricyclic sugar
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (6)..(7)
<223> OTHER INFORMATION: m5c
<220> FEATURE:
<221> NAME/KEY: misc_feature
<222> LOCATION: (10)..(10)
<223> OTHER INFORMATION: 2'-modified ribonucleoside, preferably
      2'-O-methyl ribonucleoside
<220> FEATURE:
<221> NAME/KEY: misc_feature
<222> LOCATION: (11)..(15)
<223> OTHER INFORMATION: deoxyribonucleoside with tricyclic sugar
<220> FEATURE:
<221> NAME/KEY: modified_base
<222> LOCATION: (15)..(15)
<223> OTHER INFORMATION: m5c

<400> SEQUENCE: 6
```
gccatcctgg agttc                                                          15

<210> SEQ ID NO 7
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: modified_base
<222> LOCATION: (1)..(2)
<223> OTHER INFORMATION: m5c
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(9)
<223> OTHER INFORMATION: m5c
<220> FEATURE:
<221> NAME/KEY: modified_base
<222> LOCATION: (14)..(15)
<223> OTHER INFORMATION: m5c

<400> SEQUENCE: 7
ccgctgccca atgcc                                                          15

<210> SEQ ID NO 8
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: modified_base
<222> LOCATION: (2)..(2)
<223> OTHER INFORMATION: m5c
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(10)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 8
acttcatccc actga                                                          15

<210> SEQ ID NO 9
<211> LENGTH: 15
<212> TYPE: DNA
<213> ORGANISM: Artificial Sequence
<220> FEATURE:
<223> OTHER INFORMATION: Synthetic

```
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (12)..(12)
<223> OTHER INFORMATION: m5c

<400> SEQUENCE: 9
atttcattca actgt                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (9)..(10)
<223> OTHER INFORMATION: m5c

<400> SEQUENCE: 10
ctggagttcc tgtaa                                                    15

<210> SEQ ID NO 11
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(3)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (4)..(4)
<223> OTHER INFORMATION: 2'-modified ribonucleoside, preferably
     2'-O-methyl ribonucleoside
<220> FEATURE:
<221> NAME/KEY: misc_feature
<222> LOCATION: (5)..(15)
<223> OTHER INFORMATION: deoxyribonucleoside with tricyclic sugar
<220> FEATURE:
<221> NAME/KEY: modified_base
<222> LOCATION: (9)..(10)
<223> OTHER INFORMATION: m5c

<400> SEQUENCE: 11
ctggagttcc tgtaa                                                    15
```

```
<210> SEQ ID NO 12
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: deoxyribonucleoside with tricyclic sugar
<220> FEATURE:
<221> NAME/KEY: modified_base
<222> LOCATION: (2)..(3)
<223> OTHER INFORMATION: m5c
<220> FEATURE:
<221> NAME/KEY: misc_feature
<222> LOCATION: (6)..(6)
<223> OTHER INFORMATION: 2'-modified ribonucleoside, preferably
      2'-O-methyl ribonucleoside
<220> FEATURE:
<221> NAME/KEY: misc_feature
<222> LOCATION: (7)..(15)
<223> OTHER INFORMATION: deoxyribonucleoside with tricyclic sugar
<220> FEATURE:
<221> NAME/KEY: modified_base
<222> LOCATION: (11)..(12)
<223> OTHER INFORMATION: m5c

<400> SEQUENCE: 12
tcctggagtt cctgt                                                    15

<210> SEQ ID NO 13
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(10)
<223> OTHER INFORMATION: deoxyribonucleoside with tricyclic sugar
<220> FEATURE:
<221> NAME/KEY: modified_base
<222> LOCATION: (6)..(6)
<223> OTHER INFORMATION: m5c
<220> FEATURE:
<221> NAME/KEY: misc_feature
<222> LOCATION: (11)..(11)
<223> OTHER INFORMATION: 2'-modified ribonucleoside, preferably
      2'-O-methyl ribonucleoside
<220> FEATURE:
<221> NAME/KEY: misc_feature
<222> LOCATION: (12)..(15)
<223> OTHER INFORMATION: deoxyribonucleoside with tricyclic sugar
<220> FEATURE:
<221> NAME/KEY: modified_base
<222> LOCATION: (12)..(12)
<223> OTHER INFORMATION: m5c
<220> FEATURE:
<221> NAME/KEY: modified_base
<222> LOCATION: (15)..(15)
<223> OTHER INFORMATION: m5c

<400> SEQUENCE: 13
gtgttcttgt acttc                                                    15

<210> SEQ ID NO 14
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
```

```
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (12)..(12)
<223> OTHER INFORMATION: m5c

<400> SEQUENCE: 14
ctgaaggtgt tcttg                                                      15

<210> SEQ ID NO 15
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(8)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (3)..(4)
<223> OTHER INFORMATION: m5c
<220> FEATURE:
<221> NAME/KEY: misc_feature
<222> LOCATION: (9)..(9)
<223> OTHER INFORMATION: 2'-modified ribonucleoside, preferably
      2'-O-methyl ribonucleoside
<220> FEATURE:
<221> NAME/KEY: misc_feature
<222> LOCATION: (10)..(15)
<223> OTHER INFORMATION: deoxyribonucleoside with tricyclic sugar

<400> SEQUENCE: 15
ctccggttct gaagg                                                      15

<210> SEQ ID NO 16
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: deoxyribonucleoside with tricyclic sugar
<220> FEATURE:
<221> NAME/KEY: modified_base
<222> LOCATION: (7)..(8)
<223> OTHER INFORMATION: m5c
<220> FEATURE:
<221> NAME/KEY: misc_feature
<222> LOCATION: (10)..(10)
<223> OTHER INFORMATION: 2'-modified ribonucleoside, preferably
      2'-O-methyl ribonucleoside
<220> FEATURE:
<221> NAME/KEY: misc_feature
<222> LOCATION: (11)..(15)
```

```
<223> OTHER INFORMATION: deoxyribonucleoside with tricyclic sugar
<220> FEATURE:
<221> NAME/KEY: modified_base
<222> LOCATION: (14)..(14)
<223> OTHER INFORMATION: m5c

<400> SEQUENCE: 16
ttgaatcctu taaca                                                         15

<210> SEQ ID NO 17
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (6)..(6)
<223> OTHER INFORMATION: 2'-modified ribonucleoside, preferably
      2'-O-methyl ribonucleoside
<220> FEATURE:
<221> NAME/KEY: misc_feature
<222> LOCATION: (7)..(15)
<223> OTHER INFORMATION: deoxyribonucleoside with tricyclic sugar
<220> FEATURE:
<221> NAME/KEY: modified_base
<222> LOCATION: (12)..(12)
<223> OTHER INFORMATION: m5c

<400> SEQUENCE: 17
ctttcataat gctgg                                                         15

<210> SEQ ID NO 18
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(9)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (5)..(5)
<223> OTHER INFORMATION: m5c
<220> FEATURE:
<221> NAME/KEY: misc_feature
<222> LOCATION: (10)..(10)
<223> OTHER INFORMATION: 2'-modified ribonucleoside, preferably
      2'-O-methyl ribonucleoside
<220> FEATURE:
<221> NAME/KEY: misc_feature
<222> LOCATION: (11)..(15)
<223> OTHER INFORMATION: deoxyribonucleoside with tricyclic sugar
<220> FEATURE:
<221> NAME/KEY: modified_base
<222> LOCATION: (12)..(12)
<223> OTHER INFORMATION: m5c
```

```
<400> SEQUENCE: 18
ctttcataau gctgg                                                  15

<210> SEQ ID NO 19
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 19
aagatggcat ttcta                                                  15

<210> SEQ ID NO 20
<211> LENGTH: 18
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(5)
<223> OTHER INFORMATION: deoxyribonucleoside with tricyclic sugar
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (4)..(4)
<223> OTHER INFORMATION: m5c
<220> FEATURE:
<221> NAME/KEY: misc_feature
<222> LOCATION: (6)..(6)
<223> OTHER INFORMATION: 2'-modified ribonucleoside, preferably
      2'-O-methyl ribonucleoside
<220> FEATURE:
<221> NAME/KEY: misc_feature
<222> LOCATION: (7)..(18)
<223> OTHER INFORMATION: deoxyribonucleoside with tricyclic sugar
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (10)..(10)
<223> OTHER INFORMATION: m5c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (16)..(16)
<223> OTHER INFORMATION: m5c

<400> SEQUENCE: 20
cagcagcagc agcagcag                                               18
```

```
<210> SEQ ID NO 21
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: modified_base
<222> LOCATION: (2)..(3)
<223> OTHER INFORMATION: m5c
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(14)
<223> OTHER INFORMATION: m5c

<400> SEQUENCE: 21
gcctggacag ctcct                                              15

<210> SEQ ID NO 22
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 22
aagatggcat ttcta                                              15

<210> SEQ ID NO 23
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (1)..(12)
<223> OTHER INFORMATION: phosphorothioate internucleoside linkage group
      between the 3' end of this nucleoside and the 5' end of the next
      nucleoside
<220> FEATURE:
<221> NAME/KEY: modified_base
<222> LOCATION: (1)..(2)
```

```
<223> OTHER INFORMATION: m5c
<220> FEATURE:
<221> NAME/KEY: modified_base
<222> LOCATION: (4)..(4)
<223> OTHER INFORMATION: m5c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (11)..(12)
<223> OTHER INFORMATION: m5c

<400> SEQUENCE: 23
cctcggctta cct                                                          13

<210> SEQ ID NO 24
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 24
aagauggcat ttcta                                                        15

<210> SEQ ID NO 25
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(2)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
```

```
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 25
aagauggcat ttcta                                                       15

<210> SEQ ID NO 26
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(3)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 26
aagauggcat ttcta                                                       15

<210> SEQ ID NO 27
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(4)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
```

```
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 27
aagauggcat ttcta                                                      15

<210> SEQ ID NO 28
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(5)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 28
aagauggcat ttcta                                                      15

<210> SEQ ID NO 29
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(6)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
```

```
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 29
aagauggcat ttcta                                                          15

<210> SEQ ID NO 30
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: deoxyribonucleoside with tricyclic sugar
<220> FEATURE:
<221> NAME/KEY: misc_feature
<222> LOCATION: (1)..(7)
<223> OTHER INFORMATION: a phosphorothioate internucleoside linkage
      group between the 3' end of this nucleoside and the 5' end of the
      next nucleoside
<220> FEATURE:
<221> NAME/KEY: misc_feature
<222> LOCATION: (5)..(5)
<223> OTHER INFORMATION: 2'-modified ribonucleoside, preferably
      2'-O-methyl ribonucleoside
<220> FEATURE:
<221> NAME/KEY: misc_feature
<222> LOCATION: (6)..(15)
<223> OTHER INFORMATION: deoxyribonucleoside with tricyclic sugar
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 30
aagauggcat ttcta                                                          15

<210> SEQ ID NO 31
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c
```

<400> SEQUENCE: 31
aagatggcat ttcta                                                    15

<210> SEQ ID NO 32
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(2)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 32
aagatggcat ttcta                                                    15

<210> SEQ ID NO 33
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(3)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 33
aagatggcat ttcta                                                    15

<210> SEQ ID NO 34
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(4)

```
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 34
aagatggcat ttcta                                                     15

<210> SEQ ID NO 35
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(5)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 35
aagatggcat ttcta                                                     15

<210> SEQ ID NO 36
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(6)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 36
aagatggcat ttcta                                                     15

<210> SEQ ID NO 37
<211> LENGTH: 15
```

```
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar
<220> FEATURE:
<221> NAME/KEY: misc_feature
<222> LOCATION: (1)..(7)
<223> OTHER INFORMATION: a phosphorothioate internucleoside linkage
      group between the 3' end of this nucleoside and the 5' end of the
      next nucleoside
<220> FEATURE:
<221> NAME/KEY: modified_base
<222> LOCATION: (8)..(8)
<223> OTHER INFORMATION: m5c
<220> FEATURE:
<221> NAME/KEY: modified_base
<222> LOCATION: (13)..(13)
<223> OTHER INFORMATION: m5c

<400> SEQUENCE: 37
aagatggcat ttcta                                                    15

<210> SEQ ID NO 38
<211> LENGTH: 22
<212> TYPE: DNA
<213> ORGANISM: Artificial Sequence
<220> FEATURE:
<223> OTHER INFORMATION: Synthetic

<400> SEQUENCE: 38
cagaattctg ccaattgctg ag                                            22

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ttcttcagct tgtgtcatcc                                               20

<210> SEQ ID NO 40
<211> LENGTH: 24
<212> TYPE: DNA
<213> ORGANISM: Artificial Sequence
<220> FEATURE:
<223> OTHER INFORMATION: Synthetic

<400> SEQUENCE: 40
cccagtctac caccctatca gagc                                          24

<210> SEQ ID NO 41
<211> LENGTH: 20
<212> TYPE: DNA
<213> ORGANISM: Artificial Sequence
<220> FEATURE:
<223> OTHER INFORMATION: Synthetic

<400> SEQUENCE: 41
cctgccttta aggcttcctt                                               20

<210> SEQ ID NO 42
<211> LENGTH: 13
<212> TYPE: DNA
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: terminal phosphate group
<220> FEATURE:
<221> NAME/KEY: misc_feature
<222> LOCATION: (10)..(12)
<223> OTHER INFORMATION: phosphorothioate internucleoside linkage group
      between the 3' end of this nucleoside and the 5' end of the next
      nucleoside

<400> SEQUENCE: 42
cctcggctta cct                                                          13

<210> SEQ ID NO 43
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: terminal phosphate group
<220> FEATURE:
<221> NAME/KEY: misc_feature
<222> LOCATION: (9)..(12)
<223> OTHER INFORMATION: phosphorothioate internucleoside linkage group
      between the 3' end of this nucleoside and the 5' end of the next
      nucleoside

<400> SEQUENCE: 43
cctcggctta cct                                                          13

<210> SEQ ID NO 44
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: terminal phosphate group
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (7)..(12)
<223> OTHER INFORMATION: phosphorothioate internucleoside linkage group
      between the 3' end of this nucleoside and the 5' end of the next
      nucleoside

<400> SEQUENCE: 44
cctcggctta cct                                                          13

<210> SEQ ID NO 45
<211> LENGTH: 13
<212> TYPE: DNA
<213> ORGANISM: Artificial Sequence
```

```
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: terminal phosphate group
<220> FEATURE:
<221> NAME/KEY: misc_feature
<222> LOCATION: (5)..(12)
<223> OTHER INFORMATION: phosphorothioate internucleoside linkage group
      between the 3' end of this nucleoside and the 5' end of the next
      nucleoside

<400> SEQUENCE: 45
cctcggctta cct                                                         13

<210> SEQ ID NO 46
<211> LENGTH: 13
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(13)
<223> OTHER INFORMATION: deoxyribonucleoside with tricyclic sugar
<220> FEATURE:
<221> NAME/KEY: misc_feature
<222> LOCATION: (1)..(1)
<223> OTHER INFORMATION: terminal phosphate group
<220> FEATURE:
<221> NAME/KEY: misc_feature
<222> LOCATION: (3)..(12)
<223> OTHER INFORMATION: phosphorothioate internucleoside linkage group
      between the 3' end of this nucleoside and the 5' end of the next
      nucleoside

<400> SEQUENCE: 46
cctcggctta cct                                                         13

<210> SEQ ID NO 47
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(15)
<223> OTHER INFORMATION: deoxyribonucleoside with tricyclic sugar

<400> SEQUENCE: 47
ctttcataat gctgg                                                       15
```

The invention claimed is:
1. A composition comprising:
   a. an oligomeric compound comprising one or more tricyclo-deoxyribonucleic acid (tc-DNA) nucleosides, wherein the oligomeric compound comprises from 5 to 40 monomer subunits; and
   b. a lipid moiety of formula $C_{3-32}$alkyl-C(O)—*,
   wherein the lipid moiety is covalently linked to the oligomeric compound at the 5' terminus or at the 3' terminus of the oligomeric compound either directly or via a spacer;
   wherein at least one tc-DNA nucleoside is of Formula (1):

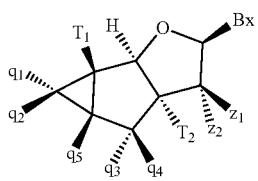

Formula (1)

wherein in Formula (1):
Bx is a nucleobase;
one of $T_1$ and $T_2$ is an internucleosidic linkage group, and the other of $T_1$ and $T_2$ is $OR_1$, $OR_2$, a 5' terminal group, a 3' terminal group or a internucleosidic linkage group, wherein $R_1$ is H or a hydroxyl protecting group, and $R_2$ is a phosphorus moiety;
$q_1$, $q_2$, $q_3$, $q_4$ and $q_5$ are each independently selected from the group consisting of hydrogen (H), halogen, $C_{1-6}$alkyl, $C_{2-6}$alkenyl, $C_{2-6}$alkynyl, substituted $C_{1-6}$alkyl, substituted $C_{2-6}$alkenyl, substituted $C_{2-6}$alkynyl, and —$(CH_2)_n$—C(O)—$R_6'$, wherein n is 0 to 6 and wherein $R_6'$ is selected from the group consisting of OH, $NH_2$, O—$C_{1-32}$alkyl and NH—$C_{1-32}$alkyl;
z1 and z2 are each independently selected from the group consisting of H, halogen, $C_{1-6}$alkyl, $C_{1-6}$alkoxyl, O—$C_{2-6}$alkenyl, O—$C_{2-6}$alkynyl, substituted $C_{1-6}$alkyl, substituted $C_{1-6}$alkoxy, substituted O—$C_{2-6}$alkenyl, and substituted O—$C_{2-6}$alkynyl;
or a pharmaceutically acceptable salt thereof, and
wherein the oligomeric compound is at least 50% complementary to a splice donor and/or acceptor site within a dystrophin pre-mRNA sequence.

2. The composition of claim 1, wherein the spacer comprises any one of formulas (a)-(g):
   a. #-NH—$C_{2-12}$alkylene-§,
   b. #-NH—$C_{2-12}$alkylene-OP(OH)-§,
   c. #-NH—$C_{2-12}$alkylene-OP(O)(SH)-§,
   d. #-NH—$C_{2-12}$alkylene-OP(O)(OH)-§,
   e. #-NH—$C_{2-12}$alkylene-NH—C(O)-§,
   f. #-NH—$C_{2-12}$alkylene-NH—P(O)(OH)-§,
   g. #-NH—$C_{2-12}$alkylene-NH—P(O)(SH)-§,
   wherein one or more —$CH_2$-moieties in $C_{2-12}$ alkylene are optionally replaced independently by —O—, —S—, —NH—, —C(O)—, —C(O)O—, an aryl, a heteroaryl, a cycloalkyl, a heterocycloalkyl, —OP(OH)O—, —OP(O)(SH)O—, —OP(O)(OH)O—, —NHP(O)(OH)O—, —NHP(O)(SH)O—, or —(O—$CH_2$—$CH_2$)$_k$— with k being an integer of 1 to 8, and wherein one or more —$CH_2$-moieties in $C_{2-12}$ alkylene are independently of each other optionally substituted with one or more —COOH, —$NH_2$, —OP(O)(OH)$_2$ or —OH, and wherein the (#) symbol represents the point of covalent linkage to a lipid moiety and the (§) symbol represents the point of covalent linkage to the oligomeric compound.

3. The composition of claim 1, wherein the oligomeric compound comprises one or more nucleosides other than tc-DNA nucleosides.

4. The composition of claim 1, wherein the oligomeric compound comprises from 5 to 40 monomer subunits, wherein the monomer subunits are nucleosides, and wherein one or more nucleosides are one or more tricyclo-deoxyribonucleic acid (tc-DNA) nucleosides, and wherein the monomer subunits are linked by a plurality of internucleosidic linkage groups.

5. The composition of claim 4, wherein the plurality of internucleosidic linkage groups are independently selected from a phosphorothioate linkage group and a phosphorodiester linkage group, wherein no more than 6 of the plurality of internucleosidic linkage groups are phosphorothioate linkage groups.

6. The composition of claim 4, wherein all of the plurality of internucleosidic linkage groups are phosphorodiester linkage groups.

7. The composition of claim 1, wherein the oligomeric compound comprises 5, 6, 7, 8, 9, or 10 nucleotides complementary base pairing from a sequence selected from SEQ ID NOs:1-37 and splice donor and/or acceptor site within a dystrophin pre-mRNA sequence.

8. A pharmaceutical composition comprising a composition according to claim 1 and further comprising a pharmaceutically acceptable carrier, wherein the pharmaceutical composition is for use in the prevention, treatment or diagnosis of a neuromuscular or musculoskeletal disease.

9. The composition of claim 1 for use as a medicament in the prevention, treatment or diagnosis of a disease, wherein the disease is a neuromuscular or musculoskeletal disease selected from Duchenne muscular dystrophy, familial dysautonomia, spinal muscular atrophy, ataxia telangiectasia, congenital disorder of glycosylation, fronto-temporal dementia, Parkinsonism linked to chromosome 17, Niemann-Pick disease type C, neurofibromatosis type 1, neurofibromatosis type 2, megalencephalic leukoencephalopathy with subcortical cysts type 1, Pelizaeus-Merzbacher disease, Pompe disease, myotonic dystrophy type 2 (DM2 or proximal myotonic myopathy), and myotonic dystrophy type 1 (DM1 or Steinert disease).

10. The composition of claim 1, wherein the $C_{3-32}$ alkyl is unbranched and has an uneven number of carbon atoms.

11. The composition of claim 5, wherein no more than 3 of the plurality of internucleosidic linkage groups are phosphorothioate linkage groups.

12. The composition of claim 1, wherein the oligomeric compound is at least 60%, at least 70%, at least 80%, or at least 90% complementary to a splice donor and/or acceptor site within a dystrophin pre-mRNA sequence.

* * * * *